United States Patent [19]

Hoover et al.

[11] Patent Number: 5,442,044

[45] Date of Patent: Aug. 15, 1995

[54] ORALLY ACTIVE RENIN INHIBITORS

[75] Inventors: Dennis J. Hoover, Stonington; Bruce A. Lefker, Gales Ferry; Robert L. Rosati, Stonington, all of Conn.

[73] Assignee: Pfizer Inc., New York, N.Y.

[21] Appl. No.: 28,038

[22] Filed: Mar. 8, 1993

Related U.S. Application Data

[63] Continuation of Ser. No. 638,238, Jan. 4, 1991, abandoned.

[51] Int. Cl.$^6$ .................. C07K 5/06; H61K 38/05
[52] U.S. Cl. ...................... 530/331; 514/18; 514/19
[58] Field of Search ............ 514/19, 18; 530/331

[56] References Cited

U.S. PATENT DOCUMENTS

| | | | |
|---|---|---|---|
| 4,713,445 | 12/1987 | Szelke et al. | 530/330 |
| 4,814,342 | 3/1989 | Hoover et al. | 514/385 |
| 4,845,079 | 7/1989 | Luly et al. | 514/18 |
| 4,935,405 | 6/1990 | Hoover et al. | 514/19 |
| 4,994,477 | 2/1991 | Kempf et al. | 514/359 |
| 5,032,577 | 7/1991 | Fung et al. | 514/18 |
| 5,049,548 | 9/1991 | Greenlee et al. | 514/18 |
| 5,091,575 | 2/1992 | Luly et al. | 560/115 |
| 5,179,102 | 1/1993 | Hanson et al. | 514/300 |
| 5,214,129 | 5/1993 | Luly et al. | 530/331 |

FOREIGN PATENT DOCUMENTS

| | | | |
|---|---|---|---|
| 0311012 | of 0000 | European Pat. Off. | A61K 37/02 |
| 0337334 | 10/1989 | European Pat. Off. | C07K 5/02 |
| 0339483 | 11/1989 | European Pat. Off. | C07K 5/02 |
| 0364804 | 4/1990 | European Pat. Off. | C07D 211/30 |
| 0456185 | 11/1991 | European Pat. Off. | C07K 5/06 |
| 3812328 | 10/1989 | Germany | C07K 7/02 |

OTHER PUBLICATIONS

European Patent Office, Partial European Search Report, for EP Application 91300191.3 (corresponding to the U.S.S.N. 07/467,068), Apr. 28, 1992.
Burger, "Medicinal Chemistry," Second Edition pp. 565–571, 578–581, 600–601 (1960).
Denkewalter et al., "Progress in Drug Research," vol. 10 pp. 510–512 (1966).
Bolis et al., "Renin Inhibitors. Dipeptide Analogs . . . " J. Med. Chem. (1987) 30 1729–1737.
Haber et al., "Renin Inhibitors: A Search for Principles of Design," J. Card. Pharm., 10 (Suppl. 7): 554–558, (1987).
Plattner et al. "Renin Inhibitors, Dipeptide Analogs," J. Med. Chem. (1988) 31 2277–2288.

Primary Examiner—Jill Warden
Assistant Examiner—Carol A. Salata
Attorney, Agent, or Firm—Peter C. Richardson; Paul H. Ginsburg; Seymour G. Bekelnitzky

[57] ABSTRACT

This invention relates to compounds of the formula

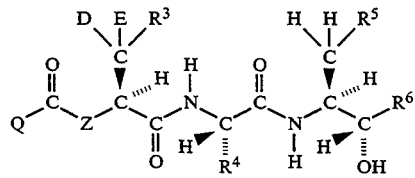

wherein Q, Z, D, E, $R^3$, $R^4$, $R^5$ and $R^6$ are defined as below, and the pharmaceutically acceptable salts thereof are disclosed. The compounds are useful as antihypertensive agents.

7 Claims, No Drawings

ORALLY ACTIVE RENIN INHIBITORS

This is a continuation of application Ser. No. 07/638,238, filed on Jan. 4, 1991, now abandoned.

BACKGROUND OF THE INVENTION

This invention relates to novel polypeptides. The compounds are useful as antihypertensive agents.

The proteolytic enzyme renin is known to be active in vivo in cleaving the naturally-occurring plasma glycoprotein angiotensinogen, in the case of human angiotensinogen at the bond between the leucine (10th) and valine (11th) amino acid residues at the N-terminal end of the angiotensinogen. The circulating N-terminal decapeptide known as angiotensin I that is formed by the above cleaving action of renin is subsequently broken down by the body to an octapeptide known as angiotensin II. Angiotensin II is known to be a potent pressor substance, i.e. a substance that is capable of inducing a significant increase in blood pressure and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known including antirenin antibodies, pepstatin and naturally-occurring phospholipid compounds.

European Patent Application Publication Number 0 266 950 of Pfizer Inc. refers to nor-statine and nor-cyclostatine polypeptides which are renin inhibitors.

European Patent Application Publication Number 0 314 239 of Merck & Co., Inc. refers to tripeptide renin inhibitors with N-terminal ureido or sulfamido groups.

European Patent Application Publication Number 0 229 667 of Abbott Laboratories claims:

"A renin inhibiting compound of the formula

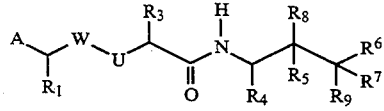

wherein A is hydrogen, lower alkyl, arylalkyl, $OR_{10}$ or $SR_{10}$ wherein $R_{10}$ is hydrogen, loweralkyl or aminoalkyl, $NR_{11}R_{12}$ wherein $R_{11}$ and $R_{12}$ are independently selected from hydrogen, loweralkyl, aminoalkyl, cyanoalkyl and hydroxyalkyl; or wherein A is

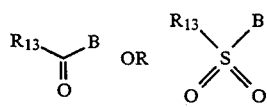

wherein B is NH, alkylamino, S, O, $CH_2$ or CHOH and $R_{13}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, aminoalkyl, N-protected aminoalkyl, alkylaminoalkyl, (N-protected)(alkyl)aminoalkyl, dialkylaminoalkyl, (heterocyclic)alkyl, or an unsubstituted heterocyclic or a monosubstituted heterocyclic wherein the substituent is hydroxy, oxo, amino, alkylamino, dialkylamino or loweralkyl, provided that when the heterocyclic is unsaturated the substituent cannot be oxo;

W is C=O or CHOH;

U is $CH_2$ or $NR_2$, provided that when W is CHOH, U is $CH_2$;

$R_1$ is loweralkyl, cycloalkylmethyl, benzyl, 4-methoxybenzyl, halobenzyl, (1-naphthyl)methyl, (2-naphthyl)methyl, (4-imidazolyl)methyl, $\alpha,\alpha$-dimethylbenzyl, 1-benzyloxyethyl, phenethyl, phenoxy, thiophenoxy or anilino; provided if $R_1$ is phenoxy, thiophenoxy or anilino, B is $CH_2$ or CHOH or A is hydrogen; $R_2$ is hydrogen or loweralkyl; $R_3$ is loweralkyl, loweralkenyl, (alkoxy)alkoxyalkyl, (thioalkoxy)alkyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or loweralkyl; $R_8$ and $R_9$ are independently selected from OH and $NH_2$; and $R_6$ is hydrogen, loweralkyl, vinyl or arylalkyl; provided that when $R_5$ and $R_7$ are both hydrogen and $R_8$ and $R_9$ are OH, the carbon bearing $R_5$ is of the "R" configuration and the carbon bearing $R_6$ is of the "S" configuration or pharmaceutically acceptable salts or esters thereof."

It will be seen that the claims of the European application cover certain compounds of the present invention. However, the European application merely encompasses certain compounds of the present invention within a broadly claimed genus and neither exemplifies any of the compounds of the present invention nor teaches one skilled in the art that such compounds should be made or how to make them.

SUMMARY OF THE INVENTION

The present invention relates to compounds of the formula

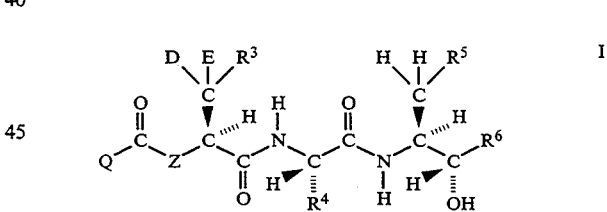

wherein Q is

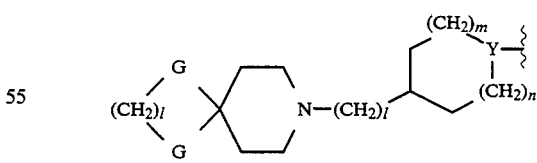

OR

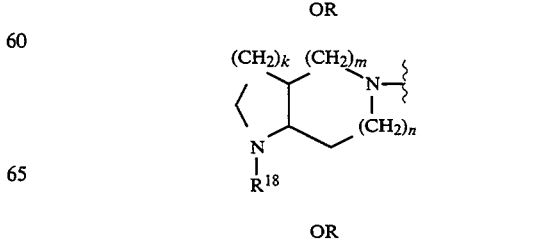

OR

-continued

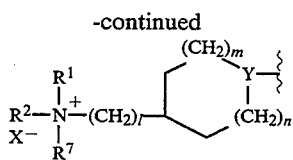

OR

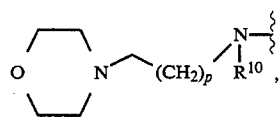

with the proviso that $R^7$ may be absent and that when $R^7$ is absent the nitrogen does not carry a positive charge and $X^-$ is absent;

$X^-$ represents a pharmaceutically acceptable anion or shared anion;

l is 0, 1, 2 or 3;

k is 1, 2 or 3;

m and n are independently 0, 1 or 2;

each i is independently 2, 3 or 4;

each G is independently oxygen or sulfur;

Y is CH or N;

$R^1$ and $R^2$ are independently selected from hydrogen, $C_1$ to $C_8$ alkyl, amino-$C_1$ to $C_8$ alkyl, hydroxy-$C_1$ to $C_8$ alkyl, $C_1$ to $C_6$ alkoxy-$C_2$ to $C_8$ alkyl, $C_1$ to $C_6$ alkylamino-$C_2$ to $C_8$ alkyl, phenyl, naphthyl, pyridyl, imidazolyl, thiazolyl, di($C_1$ to $C_8$ alkyl)amino-$C_2$ to $C_8$ alkyl, or $C_1$ to $C_8$ alkoxycarbonyl-$C_1$ to $C_8$ alkyl; or $R^1$ and $R^2$ taken together with the nitrogen atom to which they are attached form a 4 to 8 membered ring containing 0, 1 or 2 atoms selected from the group consisting of oxygen, nitrogen and sulfur, the remaining atoms in the ring being carbon, said ring optionally containing one, two, or three double bonds, and said ring optionally containing one or two substituents selected from hydroxy and $C_1$ to $C_6$ alkyl, each hydroxy substituent, when present, being attached to a carbon in the ring and each $C_1$ to $C_6$ alkyl substituent, when present, being attached to a carbon or nitrogen in the ring;

$R^7$ is $C_1$ to $C_8$ alkyl, phenyl-$C_1$ to $C_8$ alkyl, phenyl-$C_1$ to $C_8$ alkyl-$C_1$ to $C_8$ alkylamino;

p is 1 or 2;

$R^{10}$ is hydrogen, $C_1$ to $C_8$ alkyl or phenyl-$C_1$ to $C_8$ alkyl;

Z is $CH_2$, O or $NR^{13}$ wherein $R^{13}$ is hydrogen or $C_1$ to $C_5$ alkyl;

D and E are independently selected from hydrogen and $C_1$ to $C_3$ alkyl, or D and E taken together with the carbon to which they are attached form a cyclopropyl, cyclobutyl or cyclopentyl ring;

$R^3$ is phenyl, substituted phenyl, $C_5$ to $C_7$ cycloalkyl, $C_5$ to $C_7$ cycloalkylmethyl, 1-naphthyl, 2-naphthyl, substituted $C_5$ to $C_7$ cycloalkyl, phenylmethyl, substituted phenylmethyl, 2-thienyl, substituted 2-thienyl, 3-thienyl or substituted 3-thienyl, said substituted phenyl, substituted $C_5$ to $C_7$ cycloalkyl, substituted phenylmethyl, substituted 2-thienyl or substituted 3-thienyl being substituted with one or two groups selected from the group consisting of $C_1$ to $C_5$ alkoxy, $C_l$ to $C_5$ alkyl, halogen and hydroxy;

$R^4$ is $C_1$ to $C_8$ alkyl, $C_1$ to $C_8$ substituted alkyl wherein the alkyl moiety is substituted with hydroxy or one to seven fluorine atoms; $HCF_2S$-$C_1$ to $C_5$ alkyl, 4-imidazolylmethyl, 4-thiazolylmethyl, $C_2$ to $C_8$ alkenylmethyl, $C_1$ to $C_8$ alkyl-O-$C_1$ to $C_8$ alkyl, or $C_1$ to $C_8$ alkyl-S-$C_1$ to $C_8$ alkyl;

$R^5$ is 2-thienyl $C_4$ to $C_7$ cuycloalkyl, 3-thienyl, $C_5$ to $C_7$ cycloalkenyl, 1,4-cyclohexadienyl, $C_1$ to $C_8$ alkyl, substituted $C_1$ to $C_8$ alkyl, $C_1$–$C_8$ alkoxy, phenyl or substituted phenyl, wherein said substituted $C_1$ to $C_8$ alkyl and said substituted phenyl are substituted with one or two substituents selected from the group consisting of $C_1$ to $C_5$ alkoxy, $C_1$ to $C_5$ alkyl, halogen, hydroxy and oxo, or said substituted $C_1$ to $C_8$ alkyl is substituted with one to seven fluorine atoms;

$R^6$ is CO—$C_1$ to $C_8$ alkyl, COO—$C_1$ to $C_{10}$ alkyl, $COCH_2$-phenyl, $COOCH_2$—$C_1$ to $C_8$ substituted alkyl wherein the alkyl moiety is perfluorinated or substituted with 1 to 7 fluorine atoms; $C_1$ to $C_8$ alkyl-thiomethyl, 2-imidazolyl, 2-thiazolyl, 2-oxazolyl, wherein said 2-imidazolyl, 2-thiazolyl and 2-oxazolyl may optionally be substituted at one or two carbon atoms of the ring with one or two substituents independently selected from hydrogen, $C_1$ to $C_8$ alkyl, $C_2$ to $C_5$ alkenyl, halogen or $C_1$ to $C_5$ alkoxy carbonyl, and wherein said imidazolyl may additionally be substituted on one of the ring nitrogens with a substituent selected from $C_1$ to $C_5$ alkyl; phenyl, $C_5$ to $C_7$ cycloalkyl, $CONR^{16}R^{17}$ wherein $R^{16}$ and $R^{17}$ are independently selected from the group of radicals set forth in the definition of $R^1$ and $R^2$ above, except that $R^{16}$ and $R^{17}$ cannot, taken together with the nitrogen atom to which they are attached, form a ring, or $CONHR^8$ wherein $R^8$ is $C_1$ to $C_8$ alkyl or $C_1$ to $C_8$ alkyl substituted with 1 to 3 halogen atoms or with a 4-morpholino, thiazolyl, pyridyl or imidazolyl group, or substituted with a group selected from the group of radicals set forth in the definition of Q above;

or $R^6$ is a group of the formula

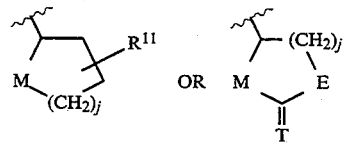

wherein j is 1 or 2; $R^{11}$ is hydrogen, $C_1$ to $C_6$ alkyl or $CH_2OH$; M is O, S, $NR^{12}$ wherein $R^{12}$ is hydrogen or $C_1$ to $C_6$ alkyl; T is O or S; E is O, S, $C=CH_2$, $NR^{14}$ wherein $R^{14}$ is hydrogen or $C_1$ to $C_6$ alkyl, or $CHR^{15}$ wherein $R^{15}$ is $C_1$ to $C_6$ alkyl;

or $R^6$ is a group of the formula

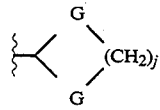

wherein each G is independently oxygen or sulfur and i is as defined above;

or $R^6$ is a group of the formula

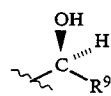

wherein $R^9$ is $C_1$ to $C_{13}$ alkyl, $C_2$ to $C_8$ alkenyl, phenyl-$C_1$ to $C_8$ alkyl, or substituted $C_1$ to $C_8$ alkyl wherein the alkyl is perfluorinated or is substituted with hydroxy or 1 to 7 fluorine atoms;

and $R^{18}$ is selected from the group of radicals set forth in the definition of $R^1$ and $R^2$ above, except that $R^{18}$ can not be a member of a ring;

and the pharmaceutically acceptable salts thereof.

It should be noted that for greater clarity, hydrogens have been omitted from the structures used in the definition of Q and that carbons are represented therein as points or dots. This has also been done for other groups that are described below. It will be clear from the foregoing that the group Q includes groups that may be represented as follows:

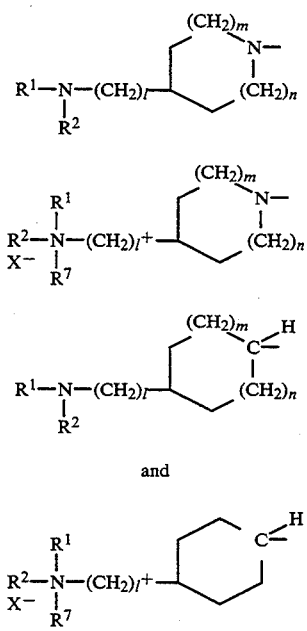

and $X^-$ is generally monovalent (e.g., $Cl^-$). However, $X^-$ may also be a shared divalent anion (e.g., $SO_4^-$). Suitable pharmaceutically acceptable anions ($X^-$) include compounds of the formula $-OCOR^{10}$ wherein $R^{10}$ is $C_1$ to $C_{12}$ alkyl (e.g., acetate), citrate, phosphate, fluoride, chloride, bromide, iodide, $-OSO_2-C_1$ to $C_{12}$ alkyl, and $-OSO_2$-phenyl-$C_1$ to $C_{12}$ alkyl. Typical pharmaceutically acceptable anions include the acetate; benzenesulfonate; benzoate; bicarbonate; bitartrate; bromide; calcium edetate; camsylate; carbonate; chloride; citrate; dihydrochloride; edetate; edisylate; estolate; esylate; fumarate; gluceptate; gluconate; glutamate; glycollylarsnilate; hexylresorcinate; hydroxynaphthoate; iodide; isothionate; lactate; lactobionate; malate; maleate; mandelate; mesylate; methylbromide; methylnitrate; methylsulfate; mucate; napsylate; nitrate; pamoate (embonate); pantothenate; phosphate; polygalacturonate; salicylate; stearate; subacetate; succinate; sulfate; tannate; tartrate; and teoclate.

Unless indicated otherwise, the alkyl, alkoxy, and alkenyl moieties referred to herein may comprise linear, branched and cyclic moieties or combinations thereof and the term "halogen" includes fluorine, chlorine, bromine and iodine. It will be understood, however that a group comprising only 1 or 2 atoms cannot by cyclic. Examples of alkyl groups are methyl, ethyl, propyl, cyclopropyl, isopropyl, butyl, t-butyl, cyclobutyl, pentyl, isopentyl, cyclopentyl, hexyl, cyclohexyl, etc.

One embodiment of the present invention relates to compounds of the formula I wherein $R^7$ is present or absent, with the proviso that when $R^6$ is

and Y is N, $R^1$ and $R^2$ are not linear or branched $C_1$ to $C_8$ alkyl. In another embodiment, $R^1$ and $R^2$ are neither linear nor branched nor cyclic $C_1$ to $C_8$ alkyl.

Preferred embodiments of the present invention relate to compounds of the formula I and the pharmaceutically acceptable salts thereof wherein one of the following eight limitations is applied:

1. 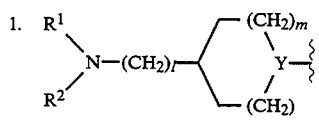

wherein $R^1$, $R^2$, l, m, n and Y are as defined above.
2. Y is N.
3. $R^3$ is $C_5$ to $C_7$ cycloalkyl (more preferably, cyclohexyl), phenyl, 2-thienyl, benzyl, 3-thienyl, 1-naphthyl, or methoxyphenyl (more preferably, p-methoxyphenyl).
4. $R^4$ is $C_1$ to $C_8$ alkyl (more preferably, $C_1$ to $C_5$ alkyl), $C_1$ to $C_8$ alkenyl-methyl, $C_1$ to $C_8$ alkoxy-$C_1$ to $C_3$ alkyl (more preferably, $C_1$ to $C_5$ alkoxy-$C_1$ to $C_3$ alkyl), $C_1$ to $C_8$ alkylthio-$C_1$ to $C_3$ alkyl (more preferably, $C_1$ to $C_5$ alkylthio-$C_1$ to $C_3$ alkyl), 4-imidazolylmethyl or 4-thiazolylmethyl (the $C_1$ to $C_3$ alkyl groups being more preferably methyl).
5. $R^5$ is $C_1$ to $C_8$ alkyl, phenyl or $C_5$ to $C_7$ cycloalkyl (more preferably, cyclohexyl, isopropyl or phenyl).
6. Z is $CH_2$, NH or O.
7. $R^6$ is $-COO-C_1$ to $C_8$ alkyl or

wherein $R^9$ is $C_1$ to $C_6$ alkyl or $C_2$ to $C_5$ alkenyl.
8. $R^1$ and R are independently selected from hydrogen, $C_1$ to $C_8$ alkyl and di($C_1$ to $C_3$ alkyl)amino-$C_2$ to $C_4$ alkyl, or $R^1$ and R taken together with the nitrogen to which they are attached form a ring which is morpholine, 4-methylpiperazine, pyrrolidine or piperidine. (More preferably, $R^1$ and $R^2$ are independently methyl, ethyl or hydrogen or $R^1$ and $R^2$ taken together with the nitrogen to which they are attached form a pyrrolidine, piperidine or methylpiperazine ring).

Particularly preferred embodiments of the present invention relate to compounds wherein two or three or all of limitations 1 to 8 are applied.

Other embodiments of this invention relate to the foregoing preferred, more preferred and particularly preferred embodiments wherein $R^1$ and $R^2$ are neither linear nor branched nor cyclic $C_1$ to $C_8$ alkyl.

Another embodiment of the present invention relates to compounds of the formula A-V-W wherein A is

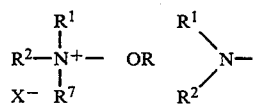

wherein $R^1$, $R^2$, $R^7$ and X are as defined above, and wherein $R^1$, $R^2$, and $R^7$ are preferably independently selected from $C_1$ to $C_8$ alkyl, with the proviso that $R^7$ may be absent and that when $R^7$ is absent, the nitrogen to which it is attached does not carry a positive charge and $X^-$ is also absent, and A is preferably $-NR^1R^2$, N-[3-(dimethylamino)propyl]-N-methylamino, pyrrolidino, piperidino, N-methyl-1,4-piperazino, methylamino or dimethylamino;

V is

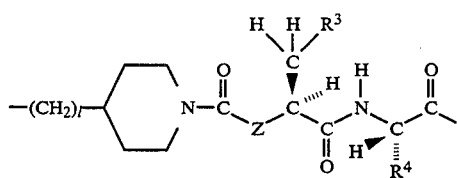

wherein Z is $CH_2$, O or $NR^{13}$ wherein $R^{13}$ is hydrogen or $C_1$ to $C_3$ alkyl, and $R^4$ is as defined above and is preferably $-CH_2SCH_3$;

and W is

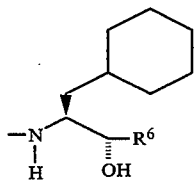

wherein $R^6$ is 2-oxazolyl, or

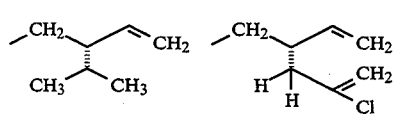

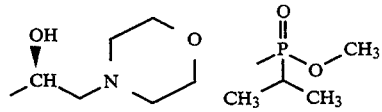

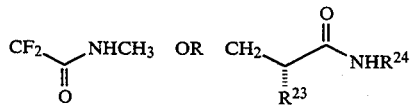

wherein $R^{23}$ is selected from $C_1$ to $C_8$ alkyl, phenyl $C_1$ to $C_8$ alkyl and $C_2$ to $C_8$ alkenyl, and $R^{224}$ is selected from $C_1$ to $C_5$ alkyl, pyridyl-$C_1$ to $C_5$ alkyl and morpholino-$C_1$ to $C_5$ alkyl;

or W is

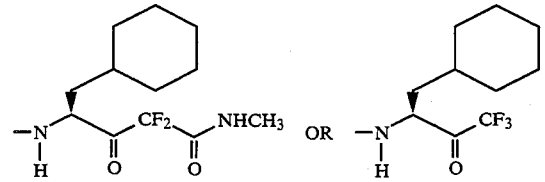

A preferred embodiment of the present invention relates to compounds of the formula

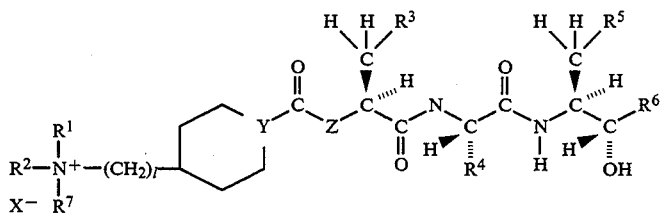

wherein $R^1$, $R^2$, $R^3$, $R^4$, $R^5$, $R^6$, $R^7$, $X^-$ and Z are as defined above for formula I, with the proviso that $R^7$ may be absent and that when $R^7$ is absent, the nitrogen from which $R^7$ is deleted does not carry a positive charge and $X^-$ is also absent. More preferably, $R^1$ and $R^2$ are independently selected from hydrogen, $C_1$ to $C_8$ alkyl, piperidino, pyrrolidino, N-($C_1$ to $C_4$ alkyl)-1, 4-piperazino, and

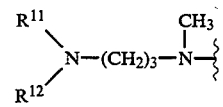

wherein $R^{11}$ and $R^{12}$ are independently selected from $C_1$ to $C_4$ alkyl; $R^7$ is $C_1$ to $C_8$ alkyl or phenyl-$C_1$ to $C_8$ alkyl; $R^3$ is phenyl, methoxyphenyl (e.g., p-methoxyphenyl), cyclohexyl or cyclohexylmethyl; $R^4$ is $C_1$ to $C_8$ alkyl, $C_1$ to $C_3$ alkylthiomethyl, $C_1$ to $C_3$ alkoxymethyl, 4-imidazolylmethyl, $CH_3-CH=CH-CH_2-$ or $CH_2-CH=CH_2-$; $R^5$ is cyclohexyl, phenyl or isopropyl; and $R^6$ is $CO-CH_2$-isopropyl, $-COO-C_1$ to $C_8$ alkyl,

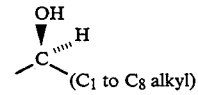

or $CONR^1R^2$ wherein $R^1$ and Rare each independently hydrogen or $C_1$ to $C_6$ alkyl.

Specific preferred compounds of the present invention include those compounds of formula I wherein Q is

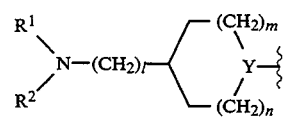

and:

a) D is hydrogen, E is hydrogen, $R^7$ is methyl, $R^1$ is methyl, $R^2$ is methyl, m and n are 1 is O, Z is NH, Y is N, $R^3$ is phenyl, $R^4$ is methylthiomethyl, $R^5$ is cyclohexyl X is iodide and $R^6$ is COO-isopropyl; or b) D is hydrogen, E is hydrogen, $R^7$ is methyl, $R^1$ is methyl, $R^2$ is methyl, m and n are 1 is O, Z is $CH_2$, Y is N, $R^3$ is phenyl, $R^4$ is methylthiomethyl, $R^5$ is cyclohexyl, X is iodide and $R^6$ is COO-isopropyl; or c) D is hydrogen, E is hydrogen, $R^7$ is absent, $R^1$ is ethyl, $R^2$ is methyl, m and n are 1 is O, Z is $CH_2$, Y is N, $R^3$ is phenyl, $R^4$ is methylthiomethyl, $R^5$ is cyclohexyl, and $R^6$ is COO-isopropyl; or d) D is hydrogen, E is hydrogen, $R^7$ is absent, $R^1$ is methyl, $R^2$ is methyl, m and n are 1 is O, Z is $CH_2$, Y is N, $R^3$ is phenyl, $R^4$ is methylthiomethyl, $R^5$ is cyclohexyl and $R^6$ is COO-(t-2,t-4-dimethylcyclopent-r-1-yl); or e) D is hydrogen, E is hydrogen, $R^7$ is absent, $R^1$ is methyl, $R^2$ is methyl, m and n are 1 is O, Z is $CH_2$, Y is N, $R^3$ is phenyl, $R^4$ is methylthiomethyl, $R^5$ is cyclohexyl and $R^6$ is COO-(t-2,t-5-dimethylcyclopent-r-1yl); or f) D is hydrogen, E is hydrogen, $R^7$ is absent, $R^1$ is methyl, $R^2$ is methyl, m and n are 1, is O, Z is NH, Y is CH, $R^3$ is phenyl, $R^4$ is methylthiomethyl, $R^5$ is cyclohexyl, and $R^6$ is COO-isopropyl; or g) D is hydrogen, E is hydrogen, $R^7$ is absent, $R^1$ is methyl, $R^2$ is methyl, m and n are 1, is O, Z is NH, Y is N, $R^3$ is cyclohexyl, $R^4$ is methylthiomethyl, $R_5$ is cyclohexyl, and $R^6$ is COO-isopropyl; or h) D is hydrogen, E is hydrogen, $R^7$ is absent $R^1$ is methyl, $R^2$ is methyl, m and n are 1, is O, Z is NH, Y is N, $R^3$ is phenyl, $R^4$ is methylthiomethyl, $R^5$ is cyclohexyl, and $R^6$ is COO-isopropyl; or i) D is hydrogen, E is hydrogen, $R^7$ is absent, $R^1$ and $R^2$ taken together form a 4-methylpiperazine ring, m and n are 1, is O, Z is NH, Y is N, $R^3$ is phenyl, $R^4$ is methylthiomethyl, $R^5$ is cyclohexyl, and $R^6$ is COO-isopropyl; or j) D is hydrogen, E is hydrogen, $R^7$ is absent, $R^1$ and $R^2$ taken together form a pyrrolidine ring, m and n are 1, is O, Z is NH, Y is N, $R^3$ is phenyl, $R^4$ is methylthiomethyl, $R^5$ is cyclohexyl, and $R^6$ is COO-isopropyl; or k) D is hydrogen, E is hydrogen, $R^7$ is absent, $R^1$ is methyl, $R^2$ is methyl, m and n are 1, 1 is 0, Z is $CH_2$, Y is N, $R^3$ is phenyl, $R^4$ is methylthiomethyl, $R^5$ is cyclohexyl, and $R^6$ is COO-isopropyl; or l) D is hydrogen, E is hydrogen, $R^7$ is absent, $R^1$ is methyl, $R^2$ is methyl, m and n are 1, 1 is 0, Z is $CH_2$, Y is N, $R^3$ is phenyl, $R^4$ is methylthiomethyl, $R^5$ is cyclohexyl, and $R^6$ is COO- (3-pentyl); or m) D is hydrogen, E is hydrogen, $R^7$ is absent, $R^1$ is methyl, $R^2$ is methyl, m and n are 1, is O, Z is NH, Y is N, $R^3$ is phenyl, $R^4$ is methylthiomethyl, $R^5$ is cyclohexyl, and $R^6$ is COO-(3-pentyl); or n) D is hydrogen, E is hydrogen, $R^7$ is absent, $R^1$ is methyl, $R^2$ is methyl, m and n are 1, is O, Z is NH, Y is N, $R^3$ is phenyl, $R^4$ is methylthiomethyl, $R^5$ is cyclohexyl, and $R^6$ is COO-(2,2-dimethylcyclopentyl); or o) D is hydrogen, E is hydrogen, $R^7$ is absent, $R^1$ is methyl, $R^{22}$ is methyl, m and n are 1, is O, Z is NH, Y is N, $R^3$ is phenyl, $R^4$ is methylthiomethyl, $R^5$ is cyclohexyl, and $R^6$ is COO-(t-2,t-4-dimethylcyclopent-r-1-yl); or p) D is hydrogen, E is hydrogen, $R^7$ is absent, $R^1$ is ethyl, $R^2$ is ethyl, m and n are 1, is O, Z is $CH_2$, Y is N, $R^3$ is phenyl, $R^4$ is methylthiomethyl, $R^5$ is cyclohexyl, and $R^6$ is COO-isopropyl; or q) D is hydrogen, E is hydrogen, $R^7$ is absent, $R^1$ is methyl, $R^2$ is methyl, m and n are 1, is O, Z is $CH_2$, Y is N, $R^3$ is 2-thienyl, $R^4$ is methylthiomethyl, $R^5$ is cyclohexyl, and $R^6$ is COO-isopropyl; or r) D is hydrogen, E is hydrogen, $R^7$ is absent, $R^1$ is hydrogen, $R^2$ is methyl, m and n are 1, is O, Z is $CH_2$, Y is N, $R^3$ is phenyl, $R^4$ is methylthiomethyl, $R^5$ is cyclohexyl, and $R^6$ is COO-isopropyl; or s) D is hydrogen, E is hydrogen, $R^7$ is absent, $R^1$ is methyl, $R^2$ is methyl, m and n are 1, is O, Z is $CH_2$, Y is N, $R^3$ is phenyl, $R^4$ is methylthiomethyl, $R^5$ is cyclohexyl, and $R^6$ is COO-(2,2-dimethylcyclopentyl).

Other preferred compounds of the present invention include those of formula I wherein Q is

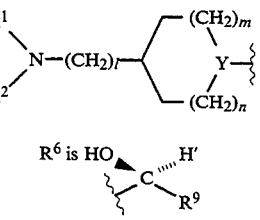

and:

a) D is hydrogen, E is hydrogen, $R^7$ is absent, $R^1$ and $R^2$ taken together form a piperidine ring, m and n are 1, is O, Z is NH, Y is N, $R^3$ is phenyl, $R^4$ is methylthiomethyl, $R^5$ is cyclohexyl, and $R^9$ is isobutyl; or b) D is hydrogen, E is hydrogen, $R^7$ is absent, $R^1$ and $R^2$ taken together form a piperidine ring, m and n are 1, is O, Z is $CH_2$, Y is N, $R^3$ is phenyl, $R^4$ is methylthiomethyl, $R^5$ is cyclohexyl, and $R^9$ is isobutyl; or c) D is hydrogen, E is hydrogen, $R^7$ is absent, $R^1$ is methyl, $R^2$ is methyl, m and n are 1, is O, Z is $CH_2$, Y is N, $R^3$ is 2-thienyl, $R^4$ is methylthiomethyl, $R^5$ is cyclohexyl, and $R^9$ is isobutyl; or d) D is hydrogen, E is hydrogen, $R^7$ is absent, $R^1$ is hydrogen, $R^2$ is methyl, m and n are 1, is O, Z is $CH_2$, Y is N, $R^3$ is 3-thienyl, $R^4$ is methylthiomethyl, $R^5$ is cyclohexyl, and $R^9$ is isobutyl; or e) D is hydrogen, E is hydrogen, $R^7$ is absent, $R^1$ is methyl, $R^2$ is methyl, m and n are 1, is 1, Z is $CH_2$, Y is N, $R^3$ is phenyl, $R^4$ is methylthiomethyl, $R^5$ is cyclohexyl, and $R^9$ is isobutyl; or f) D is hydrogen, E is hydrogen, $R^7$ is absent, $R^1$ is hydrogen, $R^2$ is methyl, m and n are 1, is 1, Z is $CH_2$, Y is N, $R^3$ is phenyl, $R^4$ is methylthiomethyl, $R^5$ is cyclohexyl, and $R^9$ is isobutyl; or g) D is hydrogen, E is hydrogen, $R^7$ is absent, $R^1$ is methyl, $R^2$ is methyl, m and n are 1, is O, Z is $CH_2$, Y is N, $R^3$ is phenyl, $R^4$ is methylthiomethyl, $R^5$ is cyclohexyl, and $R^9$ is 4-pentenyl; or h) D is hydrogen, E is hydrogen, $R^7$ is absent, $R^1$ is methyl, $R^2$ is methyl, m and n are 1, is O, Z is $CH_2$, Y is N, $R^3$ is phenyl, $R^4$ is methylthiomethyl, $R^5$ is cyclohexyl, and $R^9$ is 3-butenyl; or i) D is hydrogen, E is hydrogen, $R^7$ is absent, $R^1$ is methyl, $R^2$ is methyl, m and n are 1, is O, Z is $CH_2$, Y is N, $R^3$ is phenyl, $R^4$ is methylthiomethyl, $R^5$ is cyclohexyl, and $R^9$ is cyclopentylmethyl; or j) D is hydrogen E is hydrogen, $R^7$ is absent, $R^1$ is methyl, $R^2$ is methyl, m and n are 1, is O, Z is NH, Y is N, $R^3$ is phenyl, $R^4$ is methylthiomethyl, $R^5$ is cyclohexyl, and $R^9$ is isobutyl; or k) D is hydrogen, E is hydrogen, $R^7$ is absent, $R^1$ is methyl, $R^2$ is methyl, m and n are 1, l is 0, Z is O, Y is N, $R^3$ is phenyl, $R^4$ is methylthiomethyl, $R^5$ is cyclohexyl, and $R^9$ is isobutyl; or l) D is hydrogen, E is hydrogen, $R^7$ is absent, $R^1$ is methyl, $R^2$ is methyl, m and n are 1, l is 0, Z is $CH_2$, Y is N, $R^3$ is phenyl, $R^4$ is methylthiomethyl, $R^5$ is cyclohexyl, and $R^9$ is isobutyl; or m) D is hydrogen, E is hydrogen, $R^7$ is absent, $R^1$ is methyl, $R^2$ is methyl, m and n are 1, l is 0, Z is NH, Y is N, $R^3$ is p-methoxyphenyl, $R^4$ is methylthiomethyl, $R^5$ is cyclohexyl, and $R^9$ is isobutyl; or Specific compounds of the formula I also include the following:

4-dimethylaminopiperidine-1-carbonyl-(1-naphthyl-alanine) -SMeCys norCSta isopropyl ester;

4-dimethylaminopiperidine-l-carbonyl-(2-thienyl-alanine) -SMeCys norCSta isopropyl ester;

4-dimethylaminopiperidine-l-carbonyl-(3-thienyl-alanine) -SMeCys norCSta isopropyl ester; and 4-dimethylaminopiperidine-l-carbonyl-Phe-SMeCys norCSta cyclopentyl ester.

The present invention also includes a method for treating hypertension, congestive heart failure or glaucoma in a mammal which comprises treating said mammal with an antihypertensive, anti-congestive heart failure or anti-glaucoma effective amount of a compound of the formula I or a pharmaceutically acceptable salt thereof, and a pharmaceutical composition comprising an antihypertensive anti-congestive heart failure or anti-glaucoma effective amount of a compound of the formula I or a pharmaceutically acceptable salt thereof and a pharmaceutically acceptable carrier. Preferred compositions comprise the foregoing preferred compounds.

The pharmaceutically acceptable salts of the present invention are those which are non-toxic at the dosages administered. Since compounds of the invention may contain basic groups, acid addition salts are possible. Pharmaceutically acceptable acid addition salts include, for example, the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts.

In the interest of brevity, the commonly accepted abbreviated names of the individual amino acids have been employed where possible. For example, the amino acid phenylalanine is abbreviated as Phe, histidine as His, lysine as Lys, norcyclostatine as norCSta, S-methylcysteine as SMeCys, O-methyltyrosine as OMe-Tyr, norvaline as Nva, and norleucine as Nle, etc. The amino protecting group t-butoxycarbonyl is abbreviated as Boc, benzyloxycarbonyl as CBZ and N-t-butoxycarbonyl on the imidazole of histidine as imBoc.

NorCyclostatine is of the formula

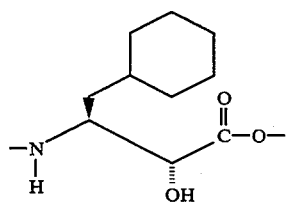

All the natural amino acids contained in the structures of the compounds of the present invention are of the L configuration, the naturally occurring configuration, unless otherwise noted.

The present invention also relates to compounds of the formulae

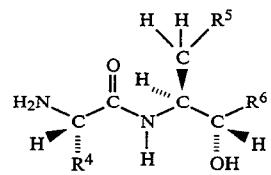

X

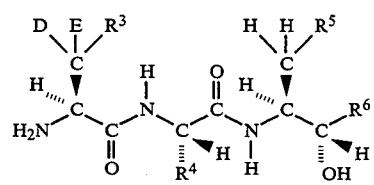

XI

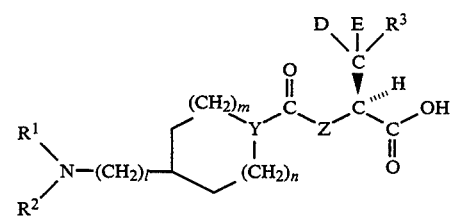

IV

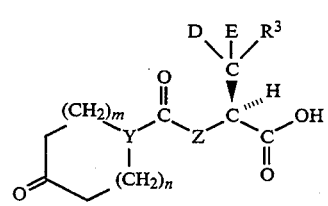

XIII

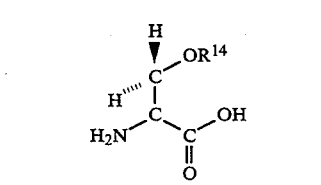

XIV

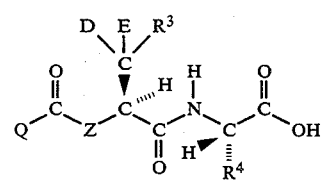

XV and

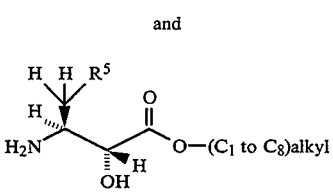

XV-A wherein $R^{14}$ is selected from $C_1$ to $C_5$ alkyl optionally substituted 1 to 6 fluorine atoms; l is 0, 1, 2 or 3; and Y, Z, D, E, m, n, $R^3$, $R^4$, $R^5$ and $R^6$ are as defined for formula I; as well as the N- and O-protected derivatives and salts of the compounds of the formulae X, XI, IV, XIII, XIV and XV and O-activated derivatives of the compounds of the formula XV. Preferred nitrogen protecting groups include tertbutoxycarbony i(BOC), carbobenzyloxy (CBZ), 7-fluorenylmethyleneoxy (FMOC) and other conventional amine protecting groups. Preferred O-protected derivatives are the corresponding t-butyl, benzyl, methyl, ethyl, and allyl esters. Preferred O-activated derivatives are the corresponding N-hydroxysuccinimide, N-hydroxybenzotriazole and pentachlorophenyl esters. Preferred salts include dicyclohexylammonium salts. These compounds are useful as intermediates for preparing the compounds of the formula I.

The present invention also relates to compounds of the formula

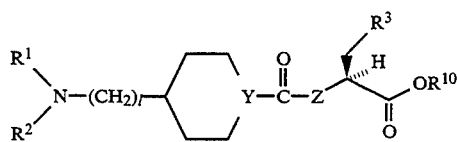

wherein $R^1$ and $R^2$ are independently selected from hydrogen, $C_1$ to $C_8$ alkyl and di($C_1$ to $C_3$ alkyl)amino-$C_2$ to $C_4$ alkyl, or $R^1$ and $R^2$ taken together with the nitrogen to which they are attached form a ring which is morpholine, 4-methylpiperazine, pyrrolidine, or piperidine; l is 0, 1, 2 or 3; Y is N or CH; Z is NH, O or $CH_2$; $R^3$ is phenyl, p-methoxyphenyl, benzyl, 1-napthyl, cyclohexyl, 2-thienyl or 3-thienyl; and $R^{10}$ is hydrogen, $C_1$ to $C_3$ alkyl or benzyl. These compounds are intermediates for preparing compounds of the formula I.

Specific intermediates that are useful in preparing compounds of the formula I are the following (structures indicated in parentheses):

t-butoxycarbonyl-OMeSer dicyclohexylammonium salt (XIV);
OMeSer-norCSta isopropyl ester hydrochloride (X);
nVal-norCSta isopropyl ester hydrochloride (X);
4-piperidone-1-carbonyl-hexahydroPhe (XIII);
4-piperidone-1-carbonyl-OMeTyr benzyl ester (XIII);
4-piperidone-1-carbonyl-OMeTyr (XIII);
OEtSer-norCSta isopropyl ester hydrochloride (X);
4-piperidone-1-carbonyl-Phe N-hydroxysuccinimide ester (XIII);
4-piperidone-1-carbonyl-Phe-S-MeCYs and its dicyclohexylamine salt (XV);
Nle-norCSta isopropyl ester hydrochloride (X);
His-norCSta isopropyl ester dihydrochloride (X);
Boc L-allyglycine-norCSta isopropyl ester (X);
L-allylglycine-norCSta isopropyl ester hydrochloride (X);
1-benzyl 4-(4-piperidone)-2 (R)-benzylsuccinate (XIII);
4-piperidone-1-carbonyl-3-L-phenyllactic acid (XIII);
Boc-Ser-norCSta isopropyl ester (X);
4-dimethylaminomethylpiperidine-1-carbonyl-L-phenyllactic acid (III);
4-dimethylaminopiperidine-1-carbonyl-cyclohexylalanine
4-(4-(BOC-N-methylamino)piperidine)-2(R)-benzylsuccinate (III);
4-dimethylaminopiperidine-1-carbonyl-OMeTyr (III);
4-(4-dimethylaminopiperidine)-2 (R)-benzylsuccinate (III);
4-dimethylaminopiperidine-1-carbonyl-Phe (III);
4-(4-dimethylaminomethylpiperidine)-2 (R)-benzylsuccinate (III);
Boc-SMeCys-2(S)-amino-1-cyclohexyl-(3(R), 4(S))-dihydroxy-6-methylheptane (X); and
SMeCys-2(S)-amino-1-cyclohexyl-(3(R), 4(S))-dihydroxy-6-methylheptane hydrochloride (X).

The present invention also relates to compounds of the formula

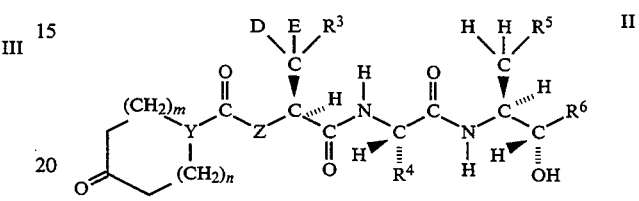

wherein m and n are independently 0 or 1; Y is CH or N; Z is O, $CH_2$, NH or $NCH_3$; D and E are independently selected from hydrogen and $C_1$ to $C_3$ alkyl, or D and E taken together with the carbon to which they are attached form a cyclopropyl, cyclobutyl or cyclopentyl ring; $R^3$ is phenyl, cyclohexyl, 1-naphthyl, 2-thienyl, 3-thienyl, benzyl, or p-methoxybenzyl; $R^4$ is $C_1$ to $C_3$ alkylthiomethyl, 4-imidazolylmethyl, $C_1$ to $C_5$ alkenylmethyl, $C_1$ to $C_3$ alkoxy-methyl or $C_2$ to $C_4$ alkyl; $R^5$ is cyclohexyl; $R^6$ is COO-$C_1$ to $C_5$ alkyl or $CONR^1R^2$ wherein $R^1$ and $R^2$ are independently selected from hydrogen and $C_1$ to $C_5$ alkyl, with the proviso that when Y is N and Z is NH or $NHCH_3$, then $R^4$ is $C_1$ to $C_5$ alkenyl-methyl; and the pharmaceutically acceptable salts thereof. These compounds are useful as intermediates for preparing the compounds of the formula I but are also active as renin inhibitors. These compounds are only about one-third as active as the compounds of the formula I. They may be used in pharmaceutical formulations and methods of treating hypertension (including treatment together with antihypertensive agents other than compounds of the formula II) as described herein provided that the dosage ranges are adjusted to take this lesser activity into account. Such pharmaceutical formulations and methods of treating hypertension are also considered to be embodiments of the present invention. Specific examples of such compounds of the formula II are the following:

4-piperidone-1-carbonyl-Phe-L-allylglycine-norCSta isopropyl ester;
4-(4-piperidone)-2(R)-benzylsuccinoyl-SMeCys-norCSta isopropyl ester; and
1-cyclohexanone-4-carbonyl-Phe-SMeCys-norCSta isopropyl ester.

DETAILED DESCRIPTION OF THE INVENTION

The following reaction schemes illustrate the preparation of the compounds of the formula I. In the reaction schemes and discussion that follow, except where otherwise indicated, $R^1$, $R^2$, $R^4$, $R^5$, $R^6$, E, D, Y, Z, m, n and Q are defined as for formula I above.

Scheme I
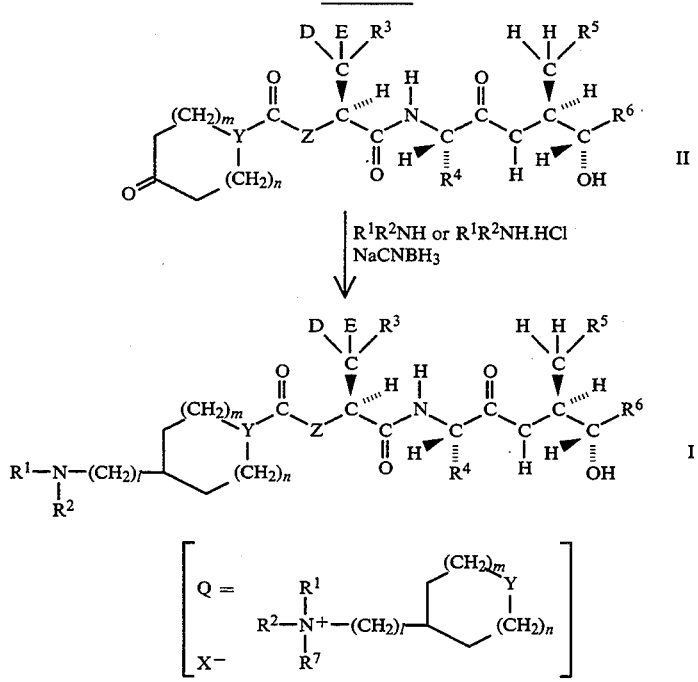
Scheme 2
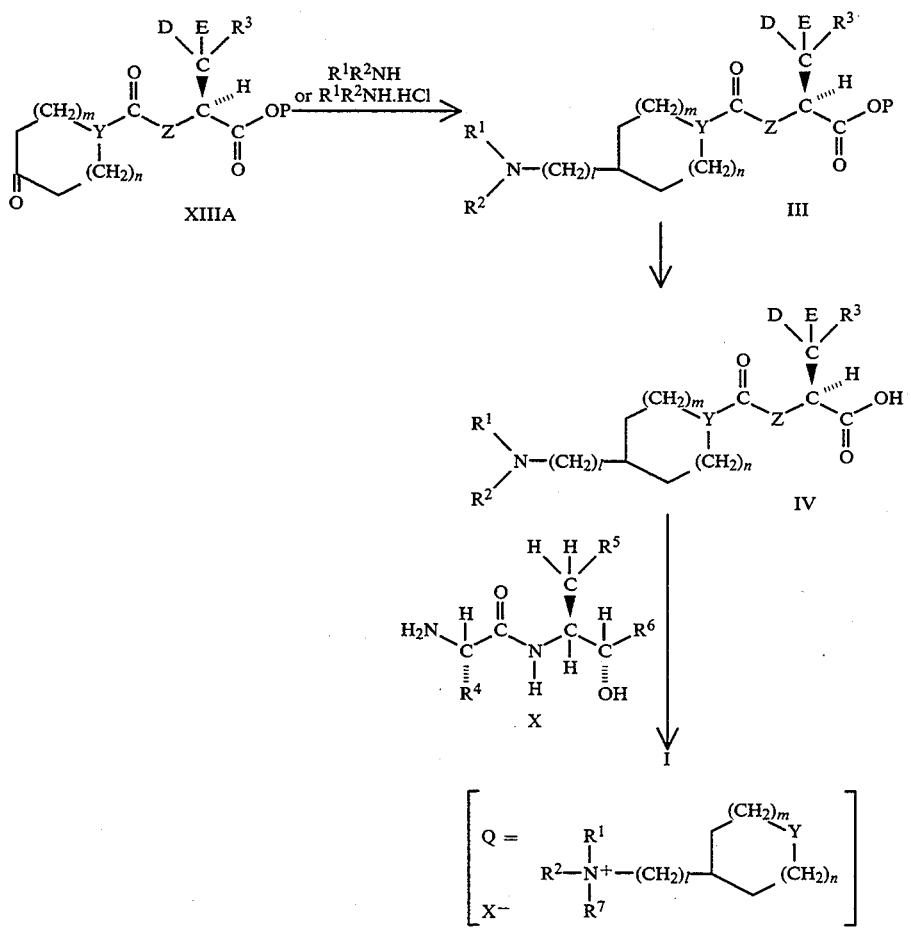

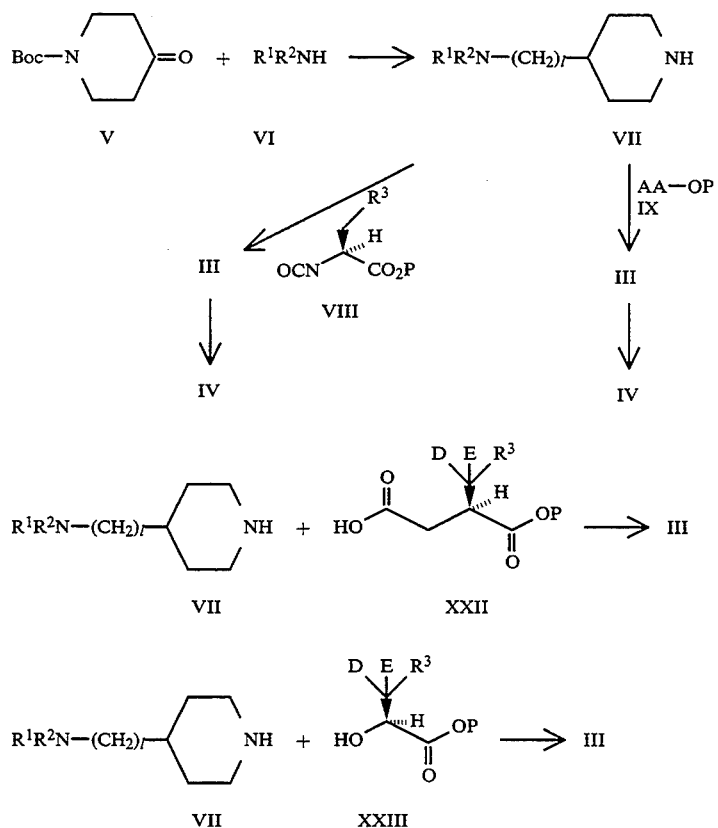
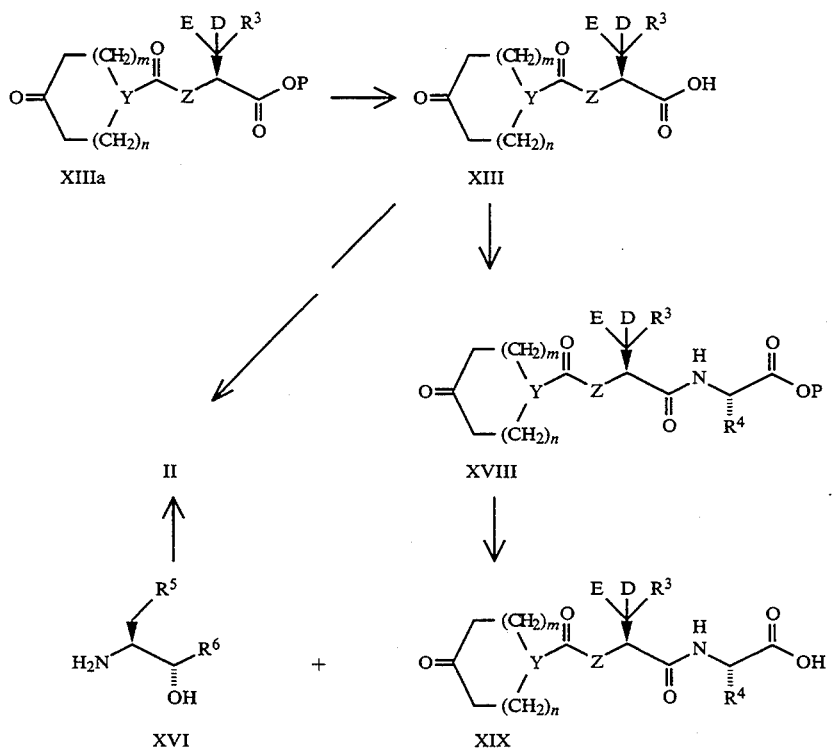

Scheme 5

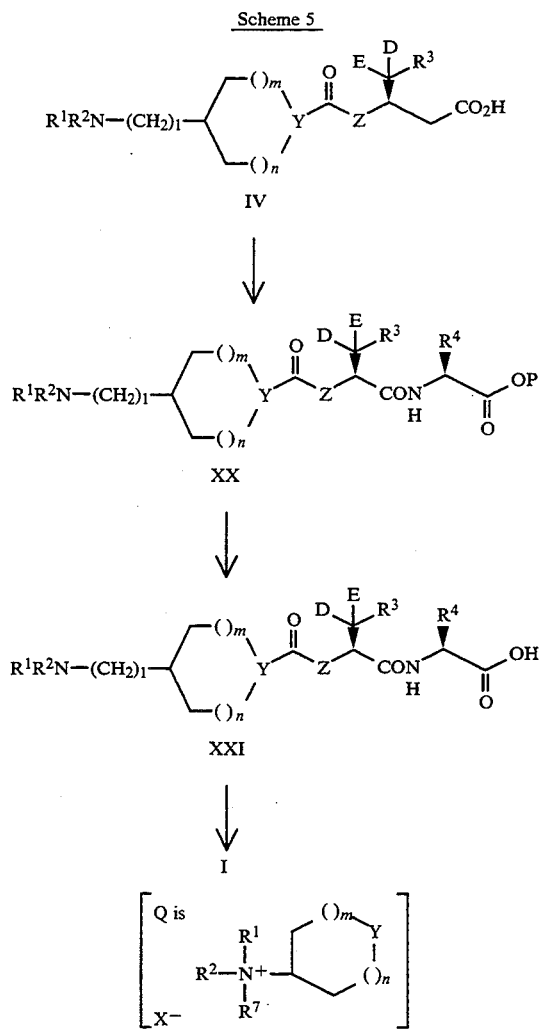

As shown in Scheme 1, a compound of the formula II, wherein l, m, n, Y, Z, D, E, $R^3$, $R^4$, $R^5$ and $R^6$ are as defined for formula I, is reacted with an amine of the formula $R^1R_2NH$ or its hydrochloride, wherein $R^1$ and $R^2$ are as defined above, in the presence of a suitable reducing agent to prepare a compound of the formula I wherein Q is

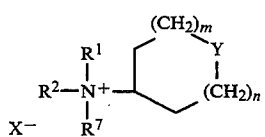

(hereinafter referred to as "a radical of formula J"). Suitable reducing agents include alkali metal borohydrides and cyanoborohydrides. The preferred reducing agent is $NaCNBH_3$. Sodium borohydride and sodium triacetoxyborohydride may be used. The reducing agent may also be hydrogen in combination with a suitable noble metal catalyst such as platinum or palladium. The preferred catalysts are palladium based catalysts such as palladium on carbon and palladium hydroxide on carbon. Hydrogen pressures from 1-1000 p.s.i. may be employed; pressures from 10 to 70 p.s.i. are preferred. When the amine hydrochloride is used rather than the amine, it is preferable to add 1-2 equivalents of base (e.g. triethylamine or sodium acetate).

The foregoing reaction is conducted in an inert solvent, preferably a polar protic solvent. Suitable solvents include acetonitrile, dimethylformamide, dioxane, tetrahydrofuran, dimethoxyethane and water. Preferred solvents are low molecular weight alcohols such as methanol, ethanol and isopropyl alcohol. The reaction mixture should be buffered between about pH 2.5 and about 7.5, preferably about 4.0 to about 6.5, preferably with sodium acetate and acetic acid. NaOH or HCl can be used to adjust the initial pH. The temperature of the foregoing reaction is generally about −78° C. to about 100° C., preferably ambient temperature (i.e., about 20°-25° C.).

Reductive amination of compounds of the formula II may also be accomplished by hydrogenation (see, for example, Emerson, Org. Reactions, 4, 134 (1948)). For a general review of reductive amination see R. F. Borch, Aldrichimica Acta, 8, 3-10 (1975).

As shown in Scheme 2, compounds of the formula I wherein Q is a radical of formula J can be prepared in three steps beginning with a compound of the formula XIIIA, which is reductively aminated with an amine of the formula $R^1R^2NH$ or its hydrochloride in the presence of a suitable reducing agent to give a compound of the formula III. Suitable and preferred reducing agents, solvents and reaction conditions are as described above with respect to Scheme I. The compounds of the formulae XIIIA and III have their carboxyl groups protected with protecting groups P. Suitable protecting groups are those commonly used for carboxyl group protection in peptide synthesis. Examples of such groups are benzyl ester and t-butyl groups. The compound of the formula III is deprotected using conventional methods to provide the compound of the formula IV. For example:

(a) If the carboxyl group of the compound of the formula III is protected by a benzyl ester, the latter may be removed by hydrogenation with a noble metal catalyst such as palladium on carbon in the presence of hydrogen. The hydrogenation is generally conducted at a temperature of about 0° to about 100° C., preferably about 20° to about 50° C.

(b) If the protecting group is a t-butyl group, such group may be removed by acidolysis. Acidolysis may be conducted with HCl in dioxane or with neat trifluoroacetic acid at a temperature of about −30° to about 70° C., preferably about −5° to about 35° C.

(c) If the protecting group is an alkyl ester, the group may be removed by basic hydrolysis. Basic hydrolysis may be conducted with a suitable base (e.g., sodium hydroxide) at a temperature of about −30° to about 120° C., preferably about 0° to about 80 C. The solvents used for removal of the protecting group should be inert solvents. Suitable and preferred solvents are as described for Scheme I. The compound of the formula IV is then coupled with a compound of the formula X by conventional peptide coupling reactions (e.g., Procedure C described below) to give the compound of the formula I. Such coupling reactions are generally conducted at a temperature of about −30° to about 80° C., preferably about 0° to about 25° C. Examples of suitable coupling reagents are dicyclohexylcarbodiimide/hydroxybenzotriazole (HBT), N-3-dimethylaminopropyl-N′-ethylcarbodiimide/HBT, 2-ethoxy-1-ethoxycarbonyl-1,2-dihydroquinoline (EEDQ), carbonyl diimidazole (CDI)/HBT, and diethylphosphorylcyanide. The solvent should be an inert solvent. Suitable and preferred solvents are as described for Scheme I.

For a discussion of other conditions used for coupling peptides see Houben-Weyl, Vol. XV, part II, E. Wunsch, Ed., George Theime Verlag, 1974, Stuttgart.

Scheme 4 illustrates a method of preparing compounds of the formula II. Referring to scheme 4, a compound of the formula XIIIa, wherein P is a protecting group and is defined as above, is deprotected by the method described above for the deprotection of compounds of the formula III, to give the corresponding compound of formula XIII. This compound is then converted to a compound having the formula XVIII by coupling it to an amino acid derivative of the formula

wherein P is defined as above. This reaction may be carried out using the conventional peptide coupling conditions outlined above. (See the discussion above relating to the reaction: IV+X→I).

The compound of formula XVIII so formed is then deprotected in the manner described above to produce the corresponding compound of formula XIX, which is then coupled with a compound of the formula XVI to yield the desired product of formula II. This coupling reaction may be carried as described above for the coupling of compounds of the formula IV with those of the formula X.

Alternatively, compounds of the formula II may be formed by coupling a compound of the formula XIII to a compound of the formula X, using the conventional coupling conditions described above.

Compounds of the formula I, wherein Q is a radical of the formula J, may also be prepared as illustrated in scheme 5. Referring to scheme 5, a compound of the formula IV is coupled to a protected amino acid of formula XVII', wherein P is defined as above, by the conventional coupling procedure described above. If $R^4$ is $CH_2SCH_3$, P is preferably t-butyl. The product of this reaction is a compound of the formula XX, wherein P is defined as above, which is then deprotected as described above to yield a compound having formula XXI. If $R^4$ is $CH_2SCH_3$ and P is benzyl, the deprotection is preferably carried out using palladium black in a formic acid solvent at a temperature from about 10° C. to about 50° C.

The compound of formula XXI so formed is then coupled, via the conventional coupling procedure described above, with a compound of the formula XVI to yield the desired compound of formula I. Diethylphosphoryl cyanide is a preferred coupling agent when $R^1$ and $R^2$ are both methyl, l is 0, Y is N, m and n are both 1, Z is $CH_2$, D and E are hydrogen, $R^3$ is phenyl and $R^4$ is $CH_2SCH_3$.

As shown in Scheme 3, a compound of the formula III may be prepared by reacting a compound of the formula VII with a compound of the formula IX, wherein AA is an appropriate alpha amino acid and P is defined as above, in the presence of carbonyldiimidazole or other phosgene equivalents useful in urea formation. The reaction is generally conducted at a temperature of about −30° to about 100° C., preferably about 0° to about 30° C., in an inert solvent. Suitable and preferred solvents are as described for Scheme I.

Alternatively, a compound of the formula III may be prepared by reacting a compound of the formula VII with a protected isocyanate of the formula VIII (wherein P is a protecting group). The reaction is generally conducted at a temperature of about −50° to about 100° C., preferably about −10° to about 50° C. The solvent should be an inert solvent. Suitable and preferred solvents are as described for Scheme I. The compound of the formula III can be deprotected to form the compound of the formula IV as described above.

Compounds of the formula III wherein Z is $CH_2$ may also be prepared, as shown in scheme 3, by reacting a compound of the formula VII with a compound of the formula XXII by conventional peptide coupling procedures (e.g., Procedure C described below). When the $R_1R_2N$- group of the compound of formula VII is not a tertiary amine, $R_1$ or $R_2$ may be replaced by a suitable amine protecting group. Preferred protecting groups are t-butoxycarbonyl (BOC) and 9-fluorenylmethyloxycarbonyl (FMOC). This reaction is generally carried out at a temperature of about −30° C. to 100° C., preferably about −5° to 30° C., in an inert solvent. Suitable and preferred solvents are as described for scheme I.

As illustrated in scheme 3, compounds of the formula III may also be prepared by reacting a compound of the formula VII with a compound of the formula XXII in the presence of carbonyldiimidazole or another phosgene equivalent useful in carbamate formation. When $R_1R_2N$ is not a tertiary amine, $R_1$ or $R_2$ may be replaced by a suitable amine protecting group. Preferred protecting groups are BOC and FMOC. This reaction is generally conducted at a temperature of about −30° C. to 100° C., preferably about −10° to 30° C., in an inert solvent. Suitable and preferred solvents are as described for scheme I.

A compound of the formula I that is not a quaternary ammonium salt can be converted to the corresponding quaternary ammonium salt by reacting such compound of the formula I with a compound of the formula $R^7X$ wherein $R^7$ is as defined above and X is Br, Cl, I, $OSO_2CH_3$, $OSO_2CH_3$, $OSO_2$-phenyl, or $OSO_2$-p-methylphenyl. The foregoing reaction is generally conducted in an inert solvent. Suitable solvents include ethyl ether, dichloromethane and acetonitrile. A preferred solvent is acetonitrile. The reaction temperature is generally about −30° to about 100° C., preferably about 20° to about 25° C. It may be convenient to prepare compounds of the formula I wherein $X^−$ is not a pharmaceutically acceptable anion. Such an anion can later be replaced by an anion that is pharmaceutically acceptable by exposure to an ion exchange resin. In addition, an anion that is pharmaceutically acceptable can similarly be replaced by another anion that may be preferred for a reason such as solid state stability or dosage form compatability.

The compounds of the formula I may be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end as described herein. The amino acids utilized to synthesize the compounds of the present invention are commercially available (as free acids, salts or esters, etc.) in both alpha-amino protected and alpha-amino unprotected forms.

Acid addition salts of compounds of the formula I may be prepared by dissolving a compound of the formula I in an inert solvent, adding a slight excess of an appropriate acid, allowing the salt to precipitate and separating the salt by filtration. The temperature of the solution use to prepare the acid addition salts is not critical. Generally, the temperature will be about $-20°$ C. to about 50° C., preferably about 20° to about 25° C. If the salt is soluble, the solvent may be evaporated and replaced by another solvent in which the salt is not soluble. Preferred solvents are ethyl ether, isopropyl ether, hexane and toluene.

The compounds of the formula X are prepared by coupling a compound of the formula

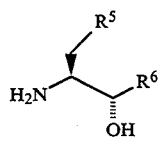

XVI with an N-protected α-amino acid bearing the $R^4$ side-chain. N-protecting groups which may be employed may be, but are not limited to, conventional ones such as CBZ, Boc, or FMOC. When said N-protected α-amino acid is histidine, the side chain is protected by an additional protecting group (e.g., Boc). The conventional coupling conditions described above for the reaction (IV+X→I) in scheme 2 are suitable. The N-protected coupling product of the formula X is then converted to the free amine or its acid addition salt by conventional means. For example, if the N-protecting group is t-Boc, it may be removed by Procedure D or by reaction with trifluoroacetic acid at 0° C., evaporation, and coevaporation with excess HCl-dioxane to form the hydrochloride. If the protecting group is CBZ, it may be removed by hydrogenation in the presence of a noble metal catalyst, preferably palladium or platinum in an inert, preferably polar, solvent such as water, a low molecular weight alcohol, or acetic or formic acid at about 0° to about 80° C., preferably about 20° to about 50° C. and hydrogen pressure of about 1 to about 5 atmospheres. Many other protecting groups and methods for their removal are also well known to those skilled in the art and may also be employed.

N-protected compounds of the formula XI are prepared by coupling an N-protected α-amino acid bearing the requisite sidechain $CH_2R^3$ to a free amine of the formula X. The free amine XI is then generated by an appropriate N-deprotection reaction. The instant N-protecting group, coupling, and deprotection reactions employed are as specified for formation of the compounds of the formula X above.

Compounds of the formula XIII wherein Y is N and Z is NH are prepared by reacting a compound of the formula

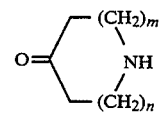

with the appropriate compound of formula IX according the procedure described above for the analogous reaction (VII+IX→III) in scheme 3 or with a protected isocyanate of the formula VIII according to the procedure described above for the analogous reaction (VII+VIII→III) in scheme 3. The resulting O-protected coupling product XIIIa is deprotected as described above for the preparation of compounds of the formula IV to give the free acid of the formula XIII.

Compounds of the formula XIIIa wherein Y=N and $Z=CH_2$ may be prepared by reacting a compound of the formula

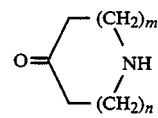

with the appropriate compound of the formula XXII according to the procedure described above for the analogous reaction (VII+XXII→II) in scheme 3.

Compounds of the formula XIIIa wherein Y=N and Z=O may be prepared by reacting a compound of the formula

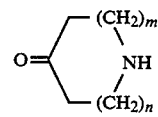

with the appropriate compound of formula XXIII according to the procedure described above for the analogous reaction (VII+XXIII III) in scheme 3.

Compounds of the formula XIIIa wherein Y is CH and Z is N or O may be prepared by reacting a compound of the formula

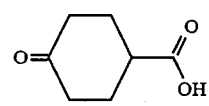

with the appropriate compound of the formula XXIII (Z=O) or IX (Z=NH) by conventional peptide coupling procedures (e.g., Procedure C described below).

Compounds of the formula XIV are prepared from amino acid carboxy protected serine derivatives, e.g. N-t-Boc-serine benzyl ester or N-CBZ-serine t-butyl ester by sequential treatment with a strong base and an alkylating agent. Suitable alkylating agents include compounds of the formula $R^{15}X$ wherein $R^{15}$ is $C_1$ to $C_5$ alkyl or allyl and X is selected from Cl, Br, I, $OSO_2CH_3$, $OSO_2CF_3$, $OSO_2$-phenyl, and $OSO_2$-p-methylphenyl. Suitable strong bases include sodium or potassium hydride. An inert, preferably dipolar, aprotic solvent such as dimethylformamide or dimethyl sulfoxide may be used. The reaction temperature is generally about $-20°$ to 80° C., preferably about 0° to 30° C. The carboxyl protecting group is then removed as described above for the preparation of compounds of the formula IV. The resulting N-protected acid XIV may be purified, if appropriate, by recrystallization as its dicyclohexylamine salt.

Compounds of the formula XV may be prepared by coupling an acid of the formula XIII with a protected α-amino ester having formula XVII, as depicted above using coupling procedures and conditions described above, in the discussion of scheme 2. The coupled product is then reductively aminated as specified above (procedure A or an equivalent procedure) and the carboxyl deprotected as described above for the preparation of the compounds of formula IV, giving a compound of the formula XV. Alternatively, compounds of the formula XV may be prepared by coupling a compound of the formula III with a carboxyl protected α-amino acid bearing the side chain $R^4$ as described above, and then deprotecting the product of such reaction in the conventional manner described above.

Compounds of the formula XVI wherein $R^6$ is COO-$C_1$ to $C_8$ alkyl may be synthesized from the corresponding methyl esters of the formula

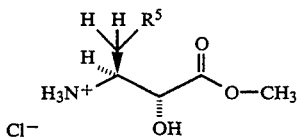

by reacting the appropriate ester with a $C_1$ to $C_8$ alcohol. Generally this reaction is run for about 10° to about 48 hours at a temperature of about 50° to about 100° C. Anhydrous hydrogen chloride may be added to catalyze the reaction.

Compounds of the formula I wherein Q is other than a radical of the formula J may be prepared by the method described above (and illustrated in scheme 2) for preparing compounds of the formula I wherein Q is a radical of the formula J, except that the starting materials are not compounds of the formula IV but the analogous compounds wherein the radicals of formula J are replaced by the appropriate Q groups. These compounds will hereinafter be referred to as compounds of the formula IV'. Compounds of the formula IV' may be prepared by any of the methods described above and illustrated in scheme 3 for converting compounds of the formula VII into compounds of the formula III and then into compounds of the formula IV. When any of these methods is used to obtain a compound of the formula IV', the starting material of formula VII shown in scheme 3 is replaced with a compound of the formula QH. Thus, a compound of the formula QH may be reacted with a compound of the formula VIII or IX or XXII or XXIII to yield a compound analogous to that of formula III but wherein the radical of formula J is replaced by the appropriate Q. Such compound may then be converted, successively, into the corresponding compounds of the formula IV'and I. This procedure is illustrated in Example 34A for

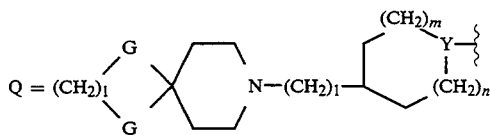

Unless indicated otherwise, the pressures of the foregoing reactions are not critical. Generally, the reaction pressures will be about 0.5 to about 2 atmospheres, preferably ambient pressure (i.e., generally at about one atmosphere).

The compounds of the formula I and the pharmaceutically acceptable salts thereof (hereinafter referred to as the active compounds of the present invention) exhibit antihypertensive activity in vivo in mammals, including humans. At least a substantial portion of this activity results from their ability to inhibit the cleavage of angiotensinogen by renin. Although we do not wish to be limited by theory, it is likely that the mechanism of the renin-inhibiting activity of the active compounds of the invention is their selective binding (as compared to angiotensinogen) to renin. The active compounds of the invention exhibit an enzyme-inhibiting activity that is selected for renin. The compounds are soluble in aqueous media, thus making oral administration feasible. The active compounds of the present invention are also useful against congestive heart failure and for the treatment of glaucoma.

The activity of the active compounds of the present invention as inhibitors of the angiotensinogen-cleaving activity of renin may be determined by studying their ability to inhibit the angiotensinogen-cleaving activity of renin in vitro.

The active compounds of the present invention may be administered for the treatment of glaucoma by direct topical application of a solution to the corneal surfaces.

The active compounds of the present invention can be administered as antihypertensive agents or agents for the treatment of congestive heart failure by either the oral or parental routes of administration, with the former being preferred for reasons of patient convenience and comfort. In general, these compounds are normally administered orally in dosages ranging from about 0.1 mg to about 20 mg per kg of body weight per day, preferably about 0.1 to about 15 mg per kg of body weight per day, and about 0.1 mg to about 5 mg per kg of body weight per day, preferably about 0.05 to about 1 mg per kg of body weight per day, when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The active compounds of the present invention can be orally administered in a wide variety of different dosage forms, i.e., they may be formulated with various pharmaceutically acceptable inert carrier in the form of tablets, capsules, lozenges, troches, hard candies, powders, sprays, aqueous suspensions, elixirs, syrups and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the active compounds of the present invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc and compositions of a similar type may also be employed. Lactose or milk sugar as well as high molecular weight polyethylene glycols may be employed as fillers in soft and hard-filled gelatin capsules. When aqueous suspensions and/or elixirs are desired for oral administration, the essential active ingredient therein may be combined with various sweetening or flavoring agents, coloring matter or dyes and, if so desired, emulsifying agents and/or solvents such as water, ethanol, propylene glycol, glycerin or combinations thereof.

One or more other active compounds may be added to the formulations described above to provide formulations for combination therapy. Such compounds include antihypertensives such as diuretics, beta-adrenergic blocking agents, central nervous system-acting agents, adrenergic neuron blocking agents, vasodilators, and angiotensin I converting enzyme inhibitors. A preferred antihypertensive agent for administration together with a compound of the present invention is a diuretic.

The following examples illustrate the invention but are not to be construed as limiting the same. All melting points are uncorrected. In the Examples, "boc" refers to t-butoxycarbonyl and "diboc" to di-t-butoxy- carbonyl.

EXAMPLES

General Methods

Melting points were determined on a Buchi apparatus and are uncorrected. FAB-MS spectra were obtained on a VG70-2505 spectrometer using a liquid matrix consisting of 3:1 dithiothreitol/dithioerythritol. $^1$H NMR spectra were recorded on a Varian XL-300 (trademark) or Bruker AM-300 (trademark) spectrometer at about 25° C. Chemical shifts are expressed in parts per million downfield from trimethylsilane. Thin layer chromatography (TLC) was done on E. Merck Kieselgel 60 $F_{254}$ (trademark) silica plates visualized (after elution with the indicated solvent(s)) by staining with 15% ethanolic phosphomolybdic acid and heating on a hot plate. High pressure liquid chromatography (HPLC) was performed at 1.5 mL/minute with 214 nm detection on a 250×4.6 mm Dupont Zorbax C-8 (trademark) column eluted isocratically by a two-pump-/mixer system supplying the indicated mixture of acetonitrile and aqueous pH 2.1 ($H_3PO_4$) 0.1M $KH_2PO_4$ respectively. Samples to be thus analyzed are dissolved in an HPLC injection buffer consisting of equal portions of acetonitrile and 0.1M pH 7.0 phosphate buffer. The HPLC retention times are reported followed by the acetonitrile/aqueous buffer ratio in parentheses. The terms "concentrated in vacuo" and "coevaporated" refer to removal of solvent at water aspirator pressure on a rotary evaporator with a bath temperature of less than 40° C.

Procedure A (Reductive Amination of Tripeptide Ketones)

The tripeptide ketone (1 mol equivalent) is dissolved in absolute methanol (25–30 mL per gram of ketone) and the resulting solution stirred in an ice bath under a nitrogen atmosphere. The amine hydrochloride (5 mol equivalent), sodium acetate (10 mol equivalent) (or, alternatively, the free amine, five equivalents of acetic acid and five equivalents of sodium acetate) and sodium cyanoborohydride (1.2 mol equivalent) are added sequentially in this order and the mixture is stirred for 16–48 hours (the ice bath is allowed to warm, thus the reaction mixture is typically held at 0°–20° C. for 4–6 hours and 20°–25° C. for the remaining period). The reaction may be conducted in the presence or absence of 3Å molecular sieves. The mixture is then evaporated at reduced pressure and the residue dissolved in dichloromethane or ethyl acetate (typically 130 mL per gram of ketone). This solution is washed twice with 1N NaOH (20 mL/gram ketone) and with brine, dried over sodium sulfate, and concentrated at reduced pressure. The residue is chromatographed on silica packed in ethanol-dichloromethane and eluted with an ethanol-dichloromethane gradient (in a typical example, 1.2 g of crude residue is chromatographed on 15 g of silica packed in 5% (v/v) ethanol-dichloromethane and eluted with 500 mL portions of 5%, 10%, 20%, and 30% (v/v) ethanol-dichloromethane). Fractions containing pure product are identified by TLC or by HPLC of evaporated aliquots reconstituted in HPLC injection buffer, pooled, evaporated, and dried in vacuo giving the target product as the free base.

Procedure B (Formation of Tripeptide Amine Hydrochlorides

The free base is dissolved at 25° C. in anhydrous 4M HCl-dioxane (typically 5–10 mL per gram free base) and evaporated to give a solid residue. This residue is pulverized under ether, hexane, or chloroform-hexane as appropriate (the choice being experimentally determined by the solvent which gives a free-flowing filterable powder) and the resulting solid is filtered, washed with small volumes of solvent, and dried in vacuo at 56° C.

Procedure C (Peptide Coupling Using. DEC.X

An 0.2–0.5M solution of the primary amine (1.0 equivalent) in dichloromethane (or a primary amine hydrochloride and 1.0–1.3 equivalent of triethylamine, unless the carboxylic acid component is a dicyclohexylammonium salt, in which case the triethylamine is omitted, or unless the carboxylic acid component also contains a tertiary amine hydrochloride group, in which case an additional equivalent of methylamine is added) is treated sequentially at 0° C. with 1.0–1.1 equivalents of the carboxylic acid coupling partner, 1.5–1.8 equivalents hydroxybenzotriazole hydrate, and 1.0–1.1 equivalents (corresponding exactly to the amount of carboxylic acid) 1-(3-dimethylaminopropyl)-3-ethylcarbodiimide hydrochloride (DEC) and the mixture is stirred overnight in an ice bath (the ice bath is allowed to warm, thus the reaction mixture is typically held at 0°–20° C. for 4–6 hours and 20°–25° C. for the remaining period). The mixture is diluted with ethyl acetate, washed twice with 1N HCl, twice with 1N NaOH, and once with brine, dried over $MgSO_4$, and concentrated giving crude product which is purified by chromatography on silica gel or trituration with an appropriate solvent as specified.

Procedure D (HCl Cleavage of a t-Boc Protected Amine)

A cold (0°–10° C.) solution of 4N HCl-dioxane is added by syringe to the solid t-Boc amine (typically about 10 mL per gram amine) and the resulting solution is stirred at 25° C. for 0.5–2 hours (the time being determined by complete conversion of the starting material to a more polar compound as judged by TLC). The resulting solution or suspension is concentrated, the residue coevaporated several times with added ether and dried in vacuo. If specified, the solid hydrochloride is further washed or triturated with solvent.

Renin Inhibition Assay

Human plasma (or plasma from other species) contains both $A_0$ and renin, and when incubated at 37° C. in a water bath, $A_1$ is generated. If all the proteolytic enzymes that metabolize $A_1$ are blocked (using ACE inhibitors etc.), then the amount of $A_1$ measured by RIA is indicative of a generation rate or enzyme activity. Plasma incubated in the presence of renin inhibitors shows less $A_1$ generation than plasma incubated without renin inhibitors. The concentration of renin inhibitor that produces one-half the "no-inhibitor" generation rate is the $IC_{50}$ for the inhibitor for that species of renin. The assay system used is Clinical Assays' (Travenol-Genentech Diagnostics Co.) GAMMACOAT-125 (trademark) competitive binding plasma renin activity radioimmunoassay (catalog number CA-533,553). Compound solution is made up as a $6.2 \times 10^{-3}$M stock solution in 100% methanol and serially diluted 1:9 with 100% methanol. Each methanol dilution is further diluted 1:9 with water. A 40 µl aliquot of each compound dilution is removed for mixing with the plasma.

Buffered plasma is made up at the time of the assay in sufficient quantity to mix 208 µl with each of the 40 1 compound aliquots plus four 40 µl aliquots of 10% methanol/H$_2$O ("no-compound" incubates). The contents, per incubate, in the buffered plasma are: 160 µl ethylenediaminetetraacetic acid plasma, 40 µl phosphate generation buffer, and inhibitors of proteolytic enzymes (4 µl 8-hydroxyquinoline, and 4 µl phenylmethylsulfonyl fluoride). All steps involving plasma are conducted in an ice bath. The incubation mix consists of 40 µl of the compound solution and 208 µl of the buffered plasma. Following addition of the buffered plasma, all tubes except two of the "no-compound" incubates are placed in a 37° C. water bath for 1 to 4 hours and returned to the ice bath. The incubation time varies with the species of plasma used. The incubates not incubated at 37° C. remain in the ice bath for the entire incubation.

Using Clinical Assays plasma renin activity kit, 2×100 1 aliquots of each incubate, and an 18 to 20 hours 4° C. incubation, $A_1$ concentrations in each incubate are determined. $A_1$ generation rates for the "no-compound" and the compound incubates are calculated by subtracting the $A_1$ concentration for the ice bath incubate from all the 37° C. incubates and dividing by the 37° C. incubation time.

$A_1$ generation rates for the compound-containing incubates are compared to the rate for the "no-compound" incubate to determine percent inhibition. The percent inhibition is plotted versus compound concentration and the concentration producing 50 percent inhibition is its $IC_{50}$.

Example 1

4-Dimethylaminopiperidine-1-carbonyl-Phe-SMeCys-norCSta Isopropyl Ester

4-Oxopiperidine-1-carbonyl-Phe-SMeCys-norCSta isopropyl ester (see U.S. Pat. No. 4,814,342) (1.5 g) was reductively aminated with dimethylamine hydrochloride for 20 hours according to Procedure A giving 1.13 g of the title substance as a colorless foam (72% yield). $^1$H NMR (300 mHz, CDCl$_3$, partial, ppm) delta: 1.25 and 1.27 (d, 3H ea, J=6.3 Hz), 2.08 (s, 3H), 2.25 (s, 6H), 2.35 (m, 1H), 2.73 (m, 2H), 2.92 (dd, 1H, J=9.3, 14.0 Hz), 3.07 (dd, 1H, J=5.3, 13.8 Hz), 3.28 (dd, 1H, J=5.0, 14.1 Hz), 3.79 (m, 2H), 4.10 (d, 1H), 4.39 (m, 1H), 4.47 (m, 1H), 4.78 (d, 1H), 5.06 (septet, 1H, J=6.3 Hz), 6.87 (d, 1H, J=8.0 Hz), 7.10 (d, 1H, J=9.6 Hz), 7.2–7.35 (m, 5H). FAB-MS m/e (relative intensity): 662 (100, MH+), 302 (55), 274 (50), 155 (50), 129 (95). HPLC (60/40): 2.83 minutes (99%).

According to Procedure B, 1.03 g of the free base was converted to the hydrochloride (1.07 g, 100%, washed with ether).

Example 2

4-Diethylaminopiperidine-1-carbonyl-Phe-SMeCys-norCStaIsopropyl Ester

4-Oxopiperidine-1-carbonyl-Phe-SMeCys-norCSta isopropyl ester (1.5 g) was reductively aminated with diethylamine hydrochloride for 48 hours according to Procedure A giving 0.465 g of the title substance as a colorless foam (28% yield). $^1$H NMR (300 mHz, CDCl$_3$, partial, ppm) delta: 1.25 and 1.27 (d, 3H ea, J=6.2 Hz), 1.38 (t, 6H, J=7.2 Hz), 2.10 (s, 3H), 2.76 (m, circa 4H), 3.01 (m, circa 5H), 3.24 (dd, 1H, J=5.3, 14.0 Hz), 4.01 (m, 1H), 4.08 (br, 1H), 4.40 (m, 3H), 5.04 (septet, 1H, J=6.2 Hz), 5.28 (br, 1H), 6.94 (d, 1H, J=9.5 HZ), 7.09 (d, 1H), 7.09 (d, 1H), 7.2–7.35 (m, circa 6H). FAB-MS m/e (relative intensity): 690 (100, MH+), 302 (33), 155 (50), 119 (100).

According to Procedure B, 0.46 g of the free base was converted to the hydrochloride (0.46 g, 95%, washed with hexane). HPLC (60/40): 3.55 minutes (98%).

Example 3

4-Methylaminopiperidine-1-carbonyl-Phe-SMeCys-norCSta Isopropyl Ester

4-Oxopiperidine-1-carbonyl-Phe-SMeCys-norCSta isopropyl ester (1.5 g) was reductively aminated with methylamine hydrochloride according to Procedure A giving 1.30 g of the title substance as a colorless foam (85% yield). $^1$H NMR (300 mHz, CDCl$_3$, partial, ppm) delta: 1.25 and 1.26 (d, 3H ea, J =6.2 Hz), 2.08 (s, 3H), 2.40 (s, 3H), 2.54 (m, 1H), 2.74 (dd, 1H, J=5.8, 13.8 Hz), 2.83 (m, 1H), 2.93 (dd, 1H, J=9.2, 14.1 Hz), 3.06 (dd, 1H, J=8.6, 13.8 Hz), 3.27 (dd, 1H, J=5.1, 14.1 Hz), 3.70 (m, 1–2H), 4.10 (d, 1H, 2.4 Hz), 4.3–4.5 (m, 2–3H), 4.82 (d, 3.9 Hz), 5.06 (septet, 1H, J=6.3 Hz), 6.90 (d, 1H, J=7.9 Hz), 7.12 (d, 1H, J=9.4 Hz), 7.2–7.35 (m, ca. 6H). FAB-Ms m/e (relative intensity): 648 (90, MH+), 288 (50), 115 (100).

According to Procedure B, 1.03 g of the free base was converted to the hydrochloride (1.37 g, 100%, washed with hexane). HPLC (60/40): 2.77 minutes (96%).

Example 4

4-(1-Morpholino) piperidine-1-carbonyl-Phe-SMeCys-nor-CSta Isopropyl Ester

4-Oxopiperidine-1-carbonyl-Phe-SMeCys-norCSta isopropyl ester (1.0 g) was reductively aminated with morpholine hydrochloride according to Procedure A giving 0.38 g of the title substance as a colorless foam (35% yield). $^1$H NMR (300 mHz, CDCl$_3$, partial,ppm) delta: 1.25 and 1.26 (d, 3H ea, J=6.3 Hz), 2.08 (s, 3H), 2.30 (m, 1H), 2.47 (m, 4H), 2.73 (m, 4H), 2.93 (dd, 1H, J=9.2, 14.2 Hz), 3.06 (dd, 1H, J=5.1, 13.8 Hz), 3.27 (dd, 1H, J=5.0, 14.1 Hz), 3.67 (m, 4H), 3.77 (m, 2H), 3.95 (m, 1H), 4.1 (br, 1H), 4.5 (m, 1H), 4.77 (d, 1H, J=3.9 HZ), 5.06 (septet, 1H, J=6.3 Hz), 6.85 (d, 1H, J=8.1 Hz), 7.07 (d, 1H, J=9.5 Hz), 7.2-7.35 (m, circa 6H).

According to Procedure B, 0.37 g of the free base was converted to the hydrochloride (0.32 g, 80%, precipitated from chloroform with several volumes of hexane). FAB-MS m/e (relative intensity): 704 (100, MH+), 344 (62), 316 (45), 197 (35), 171 (55), 126 (52). HPLC (60/40): 2.47 minutes (92%).

Example 5

4-Aminopiperidine-1-carbonyl-Phe-SMeCys-norCSta Isopropyl Ester

4-Oxopiperidine-1-carbonyl-Phe-SMeCys-norCSta isopropyl ester (1.5 g) was reductively aminated with ammonium chloride according to Procedure A giving 0.58 g of the title substance as a colorless foam (38% yield). $^1$H NMR (300 mHz, CDCl$_3$, partial, ppm) delta: 1.25 and 1.26 (d, 3H ea, J=6.2 Hz), 2.09 (s, 3H), 2.74 (dd, 1H, J=5.9, 13.9 Hz), 2.80 (m, 2-3 H), 2.93 (dd, 1H, J=9.2, 14.1 Hz), 3.07 (dd, 1H, J=5.2, 13.9 Hz), 3.27 (dd, 1H, J=5.0, 14.1 Hz), 3.74 (m, 1H), 4.09 (d, 1H, J=2.3 Hz), 4.3-4.55 (m, 3H), 4.85 (br, 1H), 5.06 (septet, 1H, J=6.3 Hz), 6.90 (d, 1H, J=8.2 Hz), 7.12 (d, 1H, J=9.5 Hz), 7.2-7.4 (m, circa 6H). FAB-MS m/e (relative intensity): 634 (60, MH+), 274 (97), 246 (38), 127 (100). HPLC (60/40): 2.25 minutes (98%).

According to Procedure B, 0.58 g of the free base was converted to the hydrochloride (0.57 g, 93% precipitated from chloroform with 5 parts hexane).

Example 6

4-Dimethylaminopiperidine-1-carbonyl-Phe-OMeSer-norCStaIso propyl Ester

A. t-Butoxycarbonyl-OMeSer Dicyclohexylammonium Salt

Boc-L-serine (15 g, 0.0731 mol) was stirred in 200 mL dry dimethylformamide at 0°-5° C. while 60% sodium hydride dispersion in oil (8.75 g, 0.219 mol) was added in portions over 20 minutes. The resulting mixture was stirred at 0°-5° C. for 1.5 hours. Methyl iodide (5.0 mL, 0.0803 mol) was added over 5 minutes and the mixture was stirred at 25° C. for 1.5 hours. The mixture was poured into a stirred mixture of ethyl acetate (600 mL) and 1N NaOH (200 mL), the layers separated, and the aqueous layer washed again with ethyl acetate (400 mL). The aqueous layer was acidified and extracted repeatedly with ethyl acetate. These extracts were combined, washed with water, dried, and chromatographed on a 9×17 cm silica column packed in 10% methanoldichloromethane giving 13.6 g of an amber oil after drying in vacuo at 60° C. This oil was dissolved in 125 mL ether and treated with 12.4 mL (1.0 equivalents) dicyclohexylamine. No solid separated after chilling or after adding some hexanes. This solution was concentrated to a yellow-brown oil which was dissolved in hexane and chilled in an ice bath. The filtered solid was washed with cold hexane and chilled in an ice bath. The filtered solid was washed with cold hexane and dried (17.2 g, 69%). Recrystallization from 100 mL hexane gave 13.9 g (56%) of the title substance an off-white crystalline solid.

B. Boc-OMeSer-norCSta Isopropyl Ester

Boc-OMeSer dicyclohexylammonium salt (4.00 g) was coupled to isopropyl 2R-hydroxy-3S-amino-4-cyclohexylbutanoate (norCSta isopropyl ester, 2.43 g, U.S. Pat. No. 4,814,342) according to Procedure C and the crudeproduct purified by chromatography on silica packed and eluted with 30/70 (v/v) ethyl acetate-hexanes, giving 3.71 g (84%) of the title substance as a colorless foam, TLC Rf 0.38 (silica, 1:1 hexane:ethyl acetate). $^1$H NMR (300 mHz, CDCl$_3$, partial, ppm) delta: 1.26 (d, 6H, J=6.3 Hz), 1.44 (s, 9H), 3.17 (d, 1H, J=4.8 Hz), 3.35 (m, 1H), 3.37 (s, 3H), 3.70 (dd, 1H, J=3.7, 9 Hz), 4.04 (dd, 1H, J=1.7, 4.9 Hz), 4.10 (m, 1H), 4.48 (m, 1H), 5.02 (septet, 1H, J=6.3 Hz), 5.36 (br, 1H), 6.46 (d, 1H, J=10 Hz).

C. OMeSer-norCSta Isopropyl Ester Hydrochloride

Boc-OMeSer-norCSta isopropyl ester (3.7 g) was deprotected according to Procedure D giving 3.50 g of the title substance as a colorless solid, TLC Rf 0.13 (silica, 18/2/1 chloroform/ethanol/acetic acid). $^1$H NMR (300 mHz, DMSO-d6, partial, ppm) delta: 1.17 and 1.19 (d, 3H ea, J=6.5, 7 Hz), 1.38 (t, 2H), 3.47 (dd, 1H, J=7, 10.5 Hz), 3.57 (s, 3H), 3.62 (dd, 1H, J=3.5, 10.5 Hz), 4.01 (m, 2H), 4.21 (m, 1H), 4.84 (septet, 1H, J=6.3 Hz), 5.60 (d, 1H, J =5.2 Hz), 8.20 (br, 1H), 8.27 (d, 1H, J=9.3 Hz).

D. 4-Piperidone-1-carbonyl-Phe-OMeSer-norCSta Isopropyl Ester

3.17 g of OMeSer-norCSta isopropyl ester hydrochloride and 2.42 g 4-piperidone-1-carbonyl-Phe (U.S. Pat. No. 4,814,342) were coupled according to Procedure C. The crude product was purified by chromatography on 95 g silica packed and eluted with ethyl acetate, giving a light yellow foam which was triturated with chloroform-hexane giving 3.45 g (67%) of the title substance as a colorless solid, TLC Rf 0.17 (silica, ethyl acetate), HPLC (60/40) 3.54 minutes (100%). $^1$H NMR (300 mHz, CDCl$_3$, partial, ppm) delta: 0.9 (m, 2H), 1.26 (d, 6H, J=6.2 Hz), 2.36 (m, 4H), 2.98 (dd, 1H, J=8.7, 14.1 Hz), 3.26 (dd, 1H, J=5.5,14.1 Hz), 3.32 (s, 3H), 3.37 (dd, 1H, J=5.8, 9 Hz), 3.56 (m, circa 4H), 3.79 (dd, 1H, J=3.3, 8.9 Hz), 4.07 (dd, 1H), 4.37 (m, 1H), 4.50 (m, 2H), 4.99 (d, 1H, J=4.8 Hz), 5.05 (septet, 1H, J=6.2 Hz), 6.73 (m, 2H), 7.2-7.35 (m, circa 6H). FAB-MS m/e (relative intensity): 617 (30, MH+), 345 (62), 287 (30), 273 (51), 245 (100), 244 (33), 202 (32).

E. 4-Dimethylaminopiperidine-1-carbonyl-Phe-OMeSer-norCSta Isopropyl Ester

4-Piperidone-1-carbonyl-Phe-OMeCys-norCSta isopropyl ester (0.5 g) was reductively aminated with dimethylamine hydrochloride according to Procedure A giving 0. 365 g of the title substance as a colorless solid (70% yield). $^1$H NMR (300 mHz, CDCl$_3$, partial, ppm)

delta: 1.25 and 1.27 (d, 3H, ea, J=6.3 Hz), 2.46 (s. 6H), 2.95 (dd, 1H, J=9.1, 14.1 Hz), 3.27 (dd, 1H, J=5.1, 14.1 Hz), 3.32 (s, 3H), 3.37 (dd, 1H, J=5.2, 9.2 Hz), 3.82 (dd, 1H, J=3.4, 9.2 Hz), 3.87 (m, 1H), 4.08 (m, 1H), 4.4 (m, 3H), 5.02 (d, 1H), 5.04 (septet, 1H, J=6.3 Hz), 6.79 (d, 7.7 Hz), 6.90 (d, 1H, J =9.8 Hz), 7.2–7.35 (m, circa 6 Hz).

According to Procedure B, 0.36 g of the free base was converted to the hydrochloride (0.292 g, 76%, washed with hexane). FAB-MS m/e (relative intensity): 646 (100, MH+), 302 (48), 274 (35), 155 (38), 129 (92). HPLC (60/40): 1.97 (greater than 95%).

Example 7

4-Dimethylaminopiperidine-1-carbonyl-Phe-nVal-norCSta-Isopropyl Ester

A. Boc-nVal-norCSta Isopropyl Ester 4.45 g of Boc-norvaline and 5.00 g of isopropyl 2R-hydroxy-3S-amino-4-cyclohexylbutanoate (norCStaisopropyl ester, U.S. Pat. No. 4,814,342) were coupled according to Procedure C and the product purified on 200 g silica packed and eluted with 1:3 (v/v) ethyl acetate-hexanes giving the title substance as a colorless solid (6.11 g, 67%), TLC Rf 0.50 (silica, 1:1 ethyl acetate-hexanes). $^1$H NMR (300 mHz, CDCl$_3$, partial, ppm) delta: 0.89 (t, 3H), 1.28 (overlapping d, 6H), 1.42 (s, 9H), 3.18 (d, 1H), 3.94 (dt, 1H), 4.07 (dd, 1H), 4.47 (dt, 1H), 4.91 (br), 5.03 (septet, 1H), 6.07 (d, 1H).

B. nVal-norCSta Isopropyl Ester Hydrochloride 6.09 g of Boc-nVal-norCSta isopropyl ester was deprotected according to Procedure D giving 5.32 g of the title substance as a colorless solid, TLC Rf 0.20 (silica, 18/2/1 trichloromethane/ethanol/acetic acid. $^1$H NMR (DMSO-d6, partial, ppm) delta: 0.87 (t, 3H, J=7.2 Hz), 1.17 and 1.18 (d, 3H ea, J=6.2 Hz), 3.75 (br, 1H), 4.01 (m, 1H), 4.23 (m, 1H), 4.83 (septet, 1H, J=6.2 Hz), 5.60 (d, 1H, J=5.1 Hz), 8.2 (m, circa 4H).

C. 4-Piperidone-1-carbonyl-Phe-nVal-norCSta Isopropy Ester 1.00 g norvaline-norCSta isopropyl ester hydrochloride and 4-piperidone-1-carbonyl-Phe (U.S. Pat. No. 4,814,342) were coupled according to Procedure C (purification by chromatography on 175 g silica packed in 1% ethanol-dichloromethane, eluted with 600 mL of 1% and 1 L each of 2%, 4%, and 6% ethanol-dichloromethane) giving 1.3 g of colorless foam which was combined with 0.18 g of a different lot of similarity prepared material and recrystallized from 9 mL of 1:2 (v/v) chloroform-hexanes giving 1.31 g of the title substance as a colorless solid, TLC Rf 0.25 (silica, ethyl acetate). $^1$H NMR (CDCl$_3$, partial, ppm) delta: 0.87 (t, 3H), 1.27 (d, 6H), 1.47 (t, 2H), 2.37 (m, 4H), 3.03 (dd, 1H), 3.20 (dd, 1H), 3.45–3.7 (m, 5H), 4.11 (dd, 1H), 4.26 (m, 1H), 4.46 (m, 1H), 4.53 (m, 1H), 5.03 (septet, 1H), 5.13 (d, 1H), 6.49 (d, 1H), 6.6 (d, 1H), 7.18–7.38 (m, circa 6H). FAB-MS m/e (relative intensity): 615 (100, MH+), 343 (51), 273 (62), 245 (69), 244 (68), 217 (21), 202 (27).

D.

4-Dimethylaminopiperidine-1-carbonyl-phe-nVal-norCSta Isopropyl Ester

4-Piperidone-1-carbonyl-Phe-nVal-norCSta isopropyl ester (0.5 g) was reductively aminated with dimethylamine hydrochloride for 20 hours according to Procedure A giving 0.33 g of the title substance as a colorless foam (63% yield).

According to Procedure B, 0.33 g of the free base was converted to the hydrochloride (0.33 g, 94%, washed with ether). $^1$H NMR (300 mHz, DMSO-d6, partial, ppm) delta: 0.86 (t, 3H, J=7.2 Hz), 1.16 and 1.18 (d, 3H ea, J=6.2 Hz), 4.83 (septet, 1H, J=6.3 Hz). FAB-MS (m/e, relative intensity): 644 (MH+, 100), 302 (32), 274 (28), 129 (69). HPLC (60/40): 2.46 minutes (99%).

Example 8

4-Dimethylaminopiperidine-1-carbonyl-hexahydrophe-SMeCys-norCSta Isopropyl Ester A. 4-Hydroxypiperidine-1-carbonyl-hexahydroPhe A mixture of 4-piperidone-1-carbonyl-Phe (U.S. Pat. No. 4,814,342), 10% rhodium on carbon, and 40 mL acetic acid was shaken at 25C and 50 p.s.i. hydrogen pressure for 23 hours and filtered through a filter aid (Supercel (trademark)). The filter cake was washed with toluene, and the filtrates concentrated in vacuo giving 3.13 g of a greenish-blue foam which was chromatographed on 200 g silica packed in 2% ethanol-dichloromethane and eluted with 1.5 L of the same solvent followed by 1 liter portions of 4%, 10%, and 15% ethanol- dichloromethane. The fractions containing product were combined and dried giving 2.18 g of a foam which was triturated with isopropyl ether and dried to yield the title substance (1.93 g, 63%), TLC Rf 0.13 (silica, 18/2/1 chloroform/ethanol/acetic acid). $^1$H NMR (300 mHz, MeOH-d4, partial, ppm) delta: 0.9 (m, 2H), 1.57 (t, 2H), 3.0 (m, 2H), 4.06 (t, 1H). FAB-MS m/e (rel intensity): 299 (100, MH+), 128 (46).

B. 4-Piperidone-1-carbonyl-hexahydroPhe

A suspension of 1.57 g of 4-hydroxypiperidine-1-carbonyl-hexahydroPhe in 25 ml diethyl ether was stirred at 0° C. and treated with 4 mL cold chromic acid solution (prepared as described in *Organic Syntheses*, Coll. Vol V, p. 310 (1973)). After 2.3 hours, another 1 mL chromic acid solution was added, the mixture stirred 5 minutes and partitioned between ethyl acetate and water. The layers were separated and the aqueous layer extracted with ethyl acetate, acidified with HCl, and extracted twice more with ethyl acetate. The latter extracts were combined and washed with brine, dried, and concentrated giving 977 mg of a dark oil which was chromatographed on 40 g silica packed in 1% ethanol-dichloromethane and eluted with 500 mL portions of 1%, 2%, 4%, and 10% ethanol-dichloromethane giving 533 mg (34%) of the title substance as an off-white foam, TLC Rf 0.68 (silica, 18/2/1 chloroform/ethanol/acetic acid). $^1$H NMR (300 mHz, CDCl$_3$, partial, ppm) delta: 2.52 (m, 4H), 4.46 (m, 1H), 5.07 (d, 1H, J=7 Hz). Partial hemiketalization or ketalization by ethanol appeared to have occurred: 1.23 (t), 3.71 (m, too large an integration for 4H). FAB-MS m/e (relative intensity): 325 (35, MH++28), 297 (100, MH+), 251 (35), 126 (58).

C.
4-Piperidone-1-carbonyl-hexahydroPhe-SMeCys-norCSta Isopropyl Ester

S-Methylcysteinyl-norCSta isopropyl ester hydrochloride (0.67 g, U.S. Pat. No. 4,814,342) and 4-piperidone-1-carbonyl-hexahydroPhe (0.50 g) were coupled according to Procedure C and the product purified by chromatography on 30 g silica packed in 1:1 ethyl acetate-hexane and eluted with 500 mL portions of 1:1, 3:2, 4:1, and 9:1 ethyl acetate-hexane, giving 0.59 g of the title substance as a colorless solid, TLC Rf 0.3 (silica, ethyl acetate). $^1$H NMR (CDCl$_3$, partial, ppm) delta: 1.26 (d, 6H, J=6.2 Hz), 1.65 (m, cyclohexyl), 2.14 (s, 3H), 2.52 (m, 4H), 2.72 (dd, 1H, J=6.9, 13.8 Hz), 2.97 (dd, 1H, J=5.2, 13.8 Hz), 3.72 (m, 4H), 4.08 (m, 1H), 4.35 (m, 2H), 4.46 (m, 1H), 4.97 (d, 1H, J=6.3 Hz), 5.02 (septet, 1H, J =6.2 Hz), 6.73 (d, 1H, J=9.6 Hz), 6.93 (d, 1H, J=7.4 Hz). Impurities appeared to be represented by singlets at 2.03, 2.08, and 2.18 ppm (circa 10/5/5%, respectively). FAB-MS m/3 (relative intensity): 639 (45, MH+), 361 (52), 279 (80), 251 (100), 202 (37), 126 (85). HPLC (60/40): 6.66 minutes with 6.31 shoulder.

D.
4-Dimethylaminopiperidine-1-carbonyl-hexahydroPhe-SMeCys-norCSta Isopropyl Ester 4-Piperidone-1-carbonyl-hexahydroPhe-SMeCys-nor- CSTA isopropyl ester (254 mg) was reductively aminated with dimethylamine according to Procedure A giving of the title substance as a colorless solid (0.145 g, 55%). $^1$H NMR (300 mHz, CDCl$_3$, partial, delta, ppm): 1.25 and 1.27 (d, 3H ea, J =6.2 Hz), 2.11 (s, 3H), 2.32 (s, 6H), 2.45 (m, 1H), 2.76 (dd, 1H, J=6.2, 13.8 Hz), 2.85 (m, 1H), 3.04 (dd, 1H, J=5.4, 13.8 Hz), 4.00 (m, 1H), 4.08 (d, 1H, J=2.2 Hz), 4.21 (m, 1H), 4.41 (m, 1H), 4.85 (d, 1H), 5.04 (septet, 1H, J=6.2 Hz ), 6.97 (m, 2H).

According to Procedure B, 0.145 g of the free base was converted to 0.125 g of the hydrochloride. FAB-MS m/e (relative intensity): 668 (70, MH+), 308 (45), 280 (45), 129 (100).

Example 9

4-(1-Pyrrolidinyl)-piperidine-1-carbonyl-Phe-SMeCys-nor-CSta Isopropyl Ester

4-Piperidone-1-carbonyl-Phe-SMeCys-norCSta isopropyl ester (1.00 g) was reductively aminated with pyrrolidine hydrochloride according to Procedure A giving 0.90 g of the title substance as a colorless solid. $^1$H NMR (300 mHz, CDCl$_3$, partial, delta, ppm): 0.8–1.0 (m, 2H), 1.25 and 1.27 (d, 3H ea, J=6.2 Hz), 1.45 (dt, 2H, J=5.2 Hz), 1.55–1.9 (overlapping m, circa 11H), 2.08 (s, 3H), 2.2 (m, circa 2H), 2.54 (br, 4H), 2.72 (dd, 1H, J=5.8, 13.9 Hz), 2.82 (m, 1H), 2.91 (dd, 1H, J=9.0, 14.0 Hz), 3.06 (dd, 1H, J=5.3, 13.8 Hz), 3.27 (dd, 1H, J=5.1, 14.1 Hz), 3.69 (t, 1H), 4.10 (d, 1H, J less than 1 Hz), 4.37–4.49 (m, 3H), 4.79 (d, 1H, 3.5 Hz), 5.06 (septet, 1H, J=6.2 Hz), 6.87 (d, 1H, J =8.0 Hz), 7.13 (d, 1H, J=9.5 Hz), 7.2–7.35 (m, circa 6-7 Hz).

According to Procedure B, 0.89 g of the free base was converted to the hydrochloride (0.93 g, 99%, washed with ether). FAB-MS (m/e, relative intensity): 688 (MH+, 100), 300 (30), 181 (30), 155 (67). HPLC (60/40): 2.72 minutes (94%).

Example 10

4-Ethylamino-piperidine-1-carbonyl-Phe-SMeCys-nor-CSta Isopropyl Ester

4-Piperidone-1-carbonyl-Phe-SMeCys-norCSta isopropyl ester (1.00 g) was reductively aminated with ethylamine hydrochloride according to Procedure A giving 0.87 g of the title substance as a colorless solid. $^1$H NMR (300 mHz, CDCl$_3$, partial, delta, ppm): 1.09 (t, 3H, J=7.1 Hz), 1.25 and 1.27 (d, 3H ea, J=6.2 Hz), 1.45 (dt, 2H, J=5.1 Hz), 1.55–1.9 (overlapping m, circa 10H), 2.08 (s, 3H), 2.64 (q , 2H, J=7.1 Hz), 2.74 (dd, J=13.8, 5.7 Hz), 2.8 (m, 1H), 2.93 (dd, 1H, J=14, 9 Hz), 3.07 (dd, 1H, J=13.7, 5.2 Hz), 3.28 (dd, 1H, J=14,5 Hz), 3.70 (m, 1H), 4.11 (d, 1H), 4.38 (m, 1H), 4.46 (m, 1H), 4.80 (d, 1H), 5.06 (septet, 1H, J=6.2 HZ), 6.87 (d, 1H, J=7 HZ), 7.13 (d, 1H, J=9.8 Hz), 7.2–7.4 (m, circa 6H).

According to Procedure B, 0.86 g of the free base was converted to the hydrochloride (0.86 g, 95%, washed with ester). FAB-MS (m/e, relative intensity): 662 (MH+, 100), 302 (57), 155 (63), 129 (97). HPLC (60/40): 2.42 minutes (96.4%).

Example 11

4-Dimethylaminopiperidine-1-carbonyl-OMeTyr-SMe-Cys-norCSta Isopropyl Ester

A. N-t-Butoxycarbonyl-O-methyl-L-tyrosine

A solution of 0-methyl-L-tyrosine (10.0 g, 0.0512 mol) and sodium hydroxide (2.05 g, 1.0 equivalent) in water (100 mL) and tetrahydrofuran (100 mL) was brought to pH 12.7 with added 6N NaOH and treated with di-t-butyldicarbonate (18 mL, 1.5 equivalents). The pH of the stirred solution gradually fell to 10.8. Most of the tetrahydrofuran was removed at reduced pressure and the aqueous residue was extracted twice with ether and mixed with an equal volume of ethyl acetate. The resulting mixture was stirred while aqueous 6N HCl was added to bring the pH to 1.5. The layers were separated and the aqueous layer extracted with ethyl acetate. The combined ethyl acetate layers were washed with brine, dried over MgSO$_4$, and concentrated giving 13.1 g (87%) of the title substance as a colorless foam, TLC Rf 0.22 (silica, 10% ethanol-dichlorome- thane), HPLC (60/40): 2.88 minutes (96%). $^1$H NMR (CDCl$_3$, 300 mHz, partial, ppm) delta: 1.41 (s, 9H), 3.09 (m, 2H), 3.78 (s, 3H), 4.55 (m, 1H), 4.90 (d, 1H), 6.83 (d, 2H, J=8.6 Hz), 7.09 (d, 2H, J=8.6 Hz).

B. N-t-Butoxycarbonyl-O-methyl-L-tyrosine Benzyl Ester

A mixture of N-t-butoxycarbonyl-O-methyl-L-tyrosine (13.1 g, 0. 0444 mol), potassium carbonate (6.14 g, 0.0444 mol, 1.0 equivalent) and benzyl bromide (5.3 mL, 0.0446 mol, 1.0 equivalent) in anhydrous dimethylformamide was stirred in an ice bath which was allowed to achieve room temperature overnight. The reaction mixture was filtered through filter aid (Supercel (trademark)) and the filter cake washed well with ethyl acetate. The combined filtrates were washed with aqueous 1M lithium chloride (3×50 mL), 1N NaOH (2×50 mL), water, and brine, dried over MgSO$_4$, and concentrated in vacuo to a light brown oil which was chromatographed on 600 g silica packed in 10% ethyl acetate-hexanes and eluted with the same solvent (1.5 L) followed by 3 L of 15% ethyl acetate-hexanes. The pure fractions were pooled and evaporated giving 15.3 g (89%) of the title substance as a colorless crystalline solid, mp 67°–69° C., TLC Rf 0.45 (silica, 1:3 ethyl acetate:hexanes), HPLC (60/40) 10.98 minutes (99%). $^1$H NMR (300 mHz, CDCl$_3$, 250 mHz, ppm) delta: 1.40 (s, 9H), 3.01 (m, 2H), 3.76 (s, 3H), 4.58 (m, 1H), 4.95 (d, 1H, J=7.9 Hz), 5.09 (d, 1H, J=11.2 Hz), 5.15 (d, 1H, J=11.2 Hz), 6.74 (d, 2H, J=8.5 Hz), 6.93 (d, 2H, J=8.4 Hz), 7.25–7.35 (m, 5H). FAB-MS m/e (relative intensity): 386 (11, MH+), 330 (50), 286 (100), 268 (50), 194 (23), 150 (45), 121 (99). Analysis: Calculated for C$_{22}$H$_{27}$NO$_5$: C, 68.55; H, 7.06; N, 3.63. Found: C, 68.46; H, 7.10; N, 3.60.

C. O-Methyl-L-tyrosine Benzyl Ester Hydrochloride 14.8 g (0.0384 mol) N-t-butoxycarbonyl-O-methyl-L-tyrosine benzyl ester was deprotected according to Procedure D and the product washed with hexanes giving 12.0 g (98%) of the title product as a colorless solid, TLC Rf 0.30 (silica, 18/2/1 chloroform/ethanol/acetic acid), HPLC (60/40) 1.96 minutes (97%). $^1$H NMR (DMSO, 300 mHz, partial, ppm) delta: 3.05 (dd, 1H, J=7.5, 14.1 Hz), 3.13 (dd, 1H, J=5.7, 14.1 Hz), 3.73 (s, 3H), 4.28 (dd, 1H), 5.15 (s, 2H), 6.84 (d, 2H, J=8.6 Hz), 7.10 (d, 2H, J=8.6 Hz), 7.29 (m, 2H), 7.36 (m, 3H), 8.63 (br, 2H).

D. 4-Piperidone-1-carbonyl-OMeTyr Benzyl Ester

A suspension of 0-Methyl-L-tyrosine benzyl ester hydrochloride (12.0 g, 0.0373 mol) and triethylamine (5.2 mL, 0.0373 mol, 1.0 equivalent) was added in a total of 90 mL dichloromethane over 10 minutes to a stirring 0° C. mixture of imidazole (5.13 g, 0. 0746 mol, 2.0 equivalent) and carbonyldiimidazole (6.65 g, 0. 0410 mol, 1.1 equivalents) in 60 mL dichloromethane. The mixture was stirred at 25° C. for 30 minutes. 4-Piperidone hydrochloride hydrate (7.45 g, 0.0485 mol, 1.3 equivalents) and triethylamine (6.8 mL, 0.0488 mol, 1.3 equivalents) were added sequentially, and the mixture was stirred for 16 hours at 25° C. Dichloromethane (300 mL) was added and the solution was washed with 1N HCl (3×100 mL). The aqueous washes were extracted once with dichloromethane, and the organic layers were combined, washed with brine, dried over MgSO$_4$, and concentrated in vacuo to a light yellow oil which was coevaporated with ether several times and dried giving the title substance as a free-flowing solid (14.3 g, 93%), TLC Rf 0.20 (silica, 2:1 ethyl acetate-hexanes), HPLC (70/30) 2.36 minutes (97%). $^1$H NMR (CDCl$_3$, 300 mHz, ppm) delta: 2.41 (m, 4H), 3.07 (m, 2H), 3.61 (m, 4H), 3.75 (s, 3H), 4.80 (m, 1H), 4.97 (d, 1H, J=7.6 Hz), 5.10 (d, 1H, J=12.1 Hz), 5.20 (d, 1H, J=12.1 Hz), 6.73 (m, 2H), 6.89 (m, 2H), 7.35 (m, 5H).

E. 4-Piperidone-1-carbonyl-OMeTyr

4-Piperidone-1-carbonyl-OMeTyr benzyl ester (5.00 g, 0.0122 mol) and 0.5 g 10% Pd/C were shaken together in 40 mL methanol and 4 mL acetic acid at 25° C. and 50 p.s.i. hydrogen for 1 hour. The mixture was filtered, the residue dissolved in ethyl acetate, and this solution washed with water (2×), and brine, dried over MgSO$_4$, and concentrated giving the title substance as an off-white solid, TLC Rf 0.35 (silica, 18/2/1 HCCl$_3$/EtOH/HOAc), HPLC (40/60) 2.42 minutes (96%). $^1$H NMR (DMSO-d6,300 mHz, ppm) delta: 2.19 (m, 4H), 2.86 (dd, 1H, J=10.5, 13.6 Hz), 3.00 (dd, 1H, J=4.5, 13.6 Hz), 3.56 (m, 4H), 3.70 (s, 3H), 4.22 (m, 1H), 6.83 (d, 2H, J=8.6 Hz), 6.92 (d, 1H, J=8.3 Hz), 7.17 (d, 2H, J=8.6 Hz).

F. 4-Piperidone-1-carbonyl-OMeTyr-SMeCyS-norCSta Isopropyl Ester 1.67 g (4.21 mmol) of S-methylcysteinyl-norCSta isopropyl ester hydrochloride and 1.35 g (4.21 mmol, 1.0 equivalent) 4-piperidone-1-carbonyl-OMeTyr were coupled according to Procedure C and the product chromatographed on 100 g silica packed in 3:1 ethyl acetate-hexanes and eluted with 3.5 L of the same solvent followed by 100% ethyl acetate giving the title substance as an off-white foam (2.08 g, 75%), TLC Rf 0.33 (silica, ethyl acetate), HPLC (60/40) 4.15 minutes (94%). $^1$H NMR (CDCl$_3$, 300 mHz, partial, ppm) delta: 1.25 and 1.26 (d, 3H ea, J=6.2 Hz), 2.10 (s, 3H), 2.41 (m, 4H), 2.71 (dd, 1H, J=6.4, 13.7 Hz), 2.92 (dd, 1H, J=8.5, 14.1 Hz), 3.01 (dd, 1H, J=5.1, 13.8 Hz), 3.20 (dd, 1H, J=5.4, 14.2 Hz), 3.58 (m, 4H), 3.77 (s, 3H), 4.09 (m, 1H), 4.43 (m, 3H), 4.97 (d, 1H, J=5.0 Hz), 5.05 (septet, 1H, J=6.3 Hz), 6.85 (d, 2H, J=8.6 Hz), 7.12 (d, 2H, J=8.6 Hz).

G. 4-Dimethylamino]piperidine-1-carbonyl-OMeTyr-SMeCys-norCsta Isopropyl Ester 4-Piperidone-1-carbonyl-OMeTyr-SMeCys-norCSta isopropyl ester (0.50 g) was reductively aminated with dimethylaminehydrochloride according to Procedure A giving the title substance (0.268 g, 51%) as a colorless solid. $^1$H NMR (CDCl$_3$, 300 mHz, partial, ppm) delta: 1.25 and 1.26 (d, 3H ea, J=6.3 Hz), 2.09 (s, 3H), 2.29 (s, 6H), 2.41 (m, 1H), 2.75 (dd, 1H, J=5.8, 13.7 Hz), 2.74 (m, 1H), 2.87 (dd, 1H, J=9.9, 14.2 Hz), 3.06 (dd, 1H, J=5.2, 13.8 Hz), 3.20 (dd, 1H, J=4.9, 14.2 Hz), 3.78 (s, 3H), 3.80 (m, 1H), 4.09 (d, 1H, J=2.4 Hz), 4.33 (m, 1H), 4.45 (m, 1H), 4.47 (m, 1H), 4.81 (d, 1H), 5.06 (septet, 1H, J=6.3 Hz), 6.85 (m, 3H), 7.14 (m, 3H). FAB-MS m/e (relative intensity): 692 (100, MH+), 332 (40), 304 (40), 155 (50), 129 (99). HPLC (60/40): 2.24 minutes (97%).

According to Procedure B, 0.26 g of the free base was converted to the hydrochloride.

Example 12

BOC-2S-amino-1-[1'4'-cyclohexadienyl]-(3R, 4S)-dihydroxy-6-methylheptane

In a three neck round bottom flask equipped with a stirring bar, a dry ice condenser and an addition funnel, 50 ml of anhydrous ammonia was condensed. BOC-2S-amino-1-phenyl-(3R,4S)-dihydroxy-6-methylheptane (EP 229667), 1.0 g, was added, followed by the addition of lithium wire until a permanent blue coloration persisted. Anhydrous t-butanol, 15 ml, was added dropwise and the reaction was allowed to warm to −30° C. Additional lithium wire was added until the blue color persisted for 15 minutes. Triethylamine hydrochloride, 3.5 g, was added and the dry ice condenser replaced by a long tubing vented into the rear of the hood. After stirring overnight at room temperature, the reaction mixture was evaporated to dryness in vacuo, and dissolved in water-ethyl acetate. The ethyl acetate layer was washed with brine, dried over MgSO$_4$, filtered and evaporated to dryness to afford 0.95 g of the title compound as a white amorphous solid. $^1$H NMR (CDCl$_3$) (partial): 0.85 (6H, 2d's); 1.40 (s, 9H); 5.45 (br, s, 1H); 5.65 (br, s, 2H).

Example 13

BOC-2S-amino-1-[1'-cyclohexenyl]-(3R,4S)-dihydroxy-6-methylheptane

BOC-2S-amino-1-[1',4'-cyclohexenyl]-(3R,4S)-dihydroxy-6-methylheptane, 250 mg, and 50 mg of 10% Pd/C catalyst were added to 20 ml of ethyl acetate. After hydrogenation at 50 psi at room temperature for 2 hours, the reaction was filtered through Super-Cel (trademark) and evaporated to dryness to yield 246 mg of a foam. After chromatography or silica gel employing chloroform as eluant, 207 mg of the title compound were obtained as a foam. $^1$H NMR (CDCl$_3$) (partial): 0.90 (2d's, 6H); 1.42 (s, 9H); 5.46 (br, s, 1H).

Example 14

4-(N-Methoxycarbonylmethyl-N-methylamino)piperidine-1-carbonyl-Phe-SMeCys-norCSTA Isopropyl Ester 4-Piperidone-1-carbonyl-Phe-SMeCys-norCSta isopropyl ester (1.0 g) was reductively aminated with N-methylglycine methyl ester hydrochloride according to Procedure A giving the title substance (0.44 g, 39%) as a colorless solid. $^1$H NMR (CDCl$_3$, 300 mHz, partial, ppm) delta: 1.25 and 1.26 (d, 3H ea, J=6.2 Hz), 2.08 (s, 3H), 2.34 (s, 3H), 2.74, (dd, 1H, J=6.0, 13.7 Hz), 2.91 (dd, 1H, J=9.1, 14.2 Hz), 3.07 (dd, 1H, J=5.0, 13.7 H), 3.27 (s, 2H), 3.28 (dd, 1H), 3.70 (s, 1H), 3.8 (m, 1–2H), 3.93 (d, 1H, J=9.0 Hz), 4.09 (d, 1H, J=8.7 Hz), 4.38 (m, 1H), 4.46 (m, 1H), 4.76 (d, 1H, J =4 Hz), 5.06 (septet, 1H, J=6.2 Hz), 6.85 (d, 1H, J=8.1 Hz), 7.08 (d, 1H, J=9.2 Hz), 7.20–7.35 (m, 5H).

According to Procedure B, 0.44 g of the free base was converted to the hydrochloride (0.34 g, 73% washed with ether). FAB-MS m/e (relative intensity): 720 (75, MH+), 360 (100), 332 (60), 185 (80), 142 (90). HPLC (60/40): 2.76 minutes (97%).

Example 15

4-N-Butylaminopiperidine-1-carbonyl-Phe-SMeCys-norCSta Isopropyl Ester

4-Piperidone-1-carbonyl-Phe-SMeCys-norCSta isopropyl ester (1.0 g) was reductively aminated with n-butylamine hydrochloride according to Procedure A giving the title substance (1.0 g, 92%) as a colorless solid. $^1$H NMR (CDCl$_3$, 300 mHz, partial, ppm) delta: 0.89 (t, 3H, J=7.2 Hz), 1.25 and 1.26 (d, 3H ea, J=6.2 Hz), 2.07 (s, 3H), 2.57 (t, 2H, J=7.2 Hz), 2.72, (dd, 1H, J=5.8, 13.8 Hz), 2.92 (dd, 1H, J=9.0, 14.1 Hz), 3.07 (dd, 1H, J=5.8, 13.8 H), 3.27 (dd, 1H, J=5.2, 14.1 Hz), 3.69 (m, 2H), 4.10 (d, 1H), 4.4–4.5 (m, 3H), 4.79 (d, 1H), 5.06 (septet, 1H, J=6.2 Hz), 6.88 (d, 1H, J=8.0 Hz), 7.12 (d, 1H, J=9.4 Hz), 7.20–7.35 (m, 5H).

According to Procedure B, 1.0 g of the free base was converted to the hydrochloride (0.82 g, 78% washed with ether). FAB-MS m/e (relative intensity): 690 (75, MH+), 330 (45), 183 (62), 157 (100). HPLC (60/40): 3.54 minutes (99%).

Example 16

4-(1-Piperidino)piperidine-1-carbonyl-Phe-SMeCys-norCSta Isopropyl Ester

4-Piperidone-1-carbonyl-Phe-SMeCys-norCSta isopropyl hydrochloride according to Procedure A giving the title substance (0.36 g, 32%) as a colorless solid. $^1$H NMR (CDCl$_3$, 300 mHz, partial, ppm) delta: 1.25 and 1.26 (d, 3H ea, J=6.2 Hz), 2.08 (s, 3H), 2.43 (m, ca. 4H), 2.72 (m, ca 2H), 2.93 (m, 1H), 3.11 (dd, 1H), 3.30 (dd, 1H), 3.8 (m, 2H), 4.4 (m, 1H), 4.5 (m, 2H), 4.76 (d, 1H), 5.07 (septet, 1H, J=6.2 Hz), 6.86 (d, 1H, J=8.1 Hz), 7.13 (d, 1H), 7.2–7.35 (m, 5H).

According to Procedure B, 0.36 g of the free base was converted to the hydrochloride (0.31 g, 82% washed with ether). FAB-MS m/e (relative intensity): 702 (100, MH+), 342 (40), 314 (70), 195 (52), 169 (100). HPLC (60/40): 2.92 minutes (97%).

Example 17

4-Isopropylaminopiperidine-1-carbonyl-Phe-SMeCys-norCSta Isopropyl Ester

4-Piperidone-1-carbonyl-Phe-SMeCys-norCSta isopropyl ester (1.0 g) was reductively aminated with piperidine hydrochloride according to Procedure A giving the title substance (0.68 g, 64%) as a colorless solid. $^1$H NMR (CDCl$_3$, 300 mHz, partial, ppm) delta: 1.02 (d, 6H, J=6.3 Hz), 1.25 and 1.26 (d, 3H ea, J=6.2 Hz), 1.45 (m, 1H), 2.08 (s, 3H), 2.43 (m, ca. 4H), 2.74 (m, 3–4H), 2.92 (m, 2H), 3.07 (dd, 1H, J=5.2, 13.8 Hz), 3.27 (dd, 1H, J=5.1, 14.0 Hz), 3.71 (m, 2H), 4.10 (d, 1H), 4.35–4.5 (m, 3H), 4.80 (d, 1H), 5.06 (septet, 1H, J=6.2 Hz), 6.88 (d, 1H, J=8.2 Hz), 7.12 (d, 1H, J=9.2 Hz), 7.2–7.35 (m, 5H).

According to Procedure B, 0.68 g of the free base was converted to the hydrochloride (0.585 g, 82% washed with ether). FAB-MS m/e (relative intensity): 676 (100, MH+), 316 (52), 288 (25), 169 (50), 143 (85). HPLC (60/40): 2.79 minutes (98%).

Example 18

4-(2-Hydroxyethylamino)-1-carbonyl-Phe-SMeCys-orCStaIsopropyl Ester

4 -Piperidone-1-carbonyl-Phe-SMeCys-norCSta isopropyl ester (1.0 g) was reductively aminated with 2-hydroxyethylamine hydrochloride according to Procedure A giving the title substance (0.68 g, 64%) as a colorless solid. $^1$H NMR (CDCl$_3$, 300 mHz, partial, ppm) delta: 1.26 and 1.27 (d, 3H ea, J=6.2 Hz), 1.45 (m, 1H), 2.09 (s, 3H), 2.77 (m, 2H, overlapping add, 1H), 2.94 (dd, 1H,J=9.0, 14.1 HZ), 3.06 (dd, 1H, J=5.2, 13.9 Hz), 3.27 (dd, 1H, J =4.0, 13.8 Hz), 3.62 (m, 2H), 3.70 (m, 3H), 4.10 (d, 1H, J =2.3 Hz), 4.39–4.5 (m, 3H), 4.82 (d, 1H, J=4.0 Hz), 5.06 (septet, 1H, J=6.2 Hz), 6.88 (d, 1H, J=8.0 Hz), 7.08 (d, 1H, J=9.3 Hz), 7.2–7.35 (m, 5H).

According to Procedure B, 0.75 g of the free base was converted to the hydrochloride (0.70 g, 89% washed with ether). FAB-MS m/e (relative intensity): 678 (70, MH+), 318 (52), 171 (53), 145 (100). HPLC (60/40): 1.96 minutes (98%).

Example 19

4-(N-3-Dimethylaminopropyl-N-methylamino)piperidine-1-carbonyl-Phe-SMeCys-norCSta Isopropyl Ester 4-Piperidone-1-carbonyl-Phe-SMeCys-norCSta isopropyl ester (1.0 g) was reductively aminated with N,N,N'-trimethyl-1,3-propanediamine dihydrochloride according to Procedure A, except that 15 equivalents of sodium acetate was used, giving the title substance (0.49 g, 42%) as a colorless solid. $^1$H NMR (CDCl$_3$, 300 mHz, partial, ppm) delta: 1.26 and 1.27 (d, 3H ea, J=6.2 Hz), 2.08 (s, 3H), 2.17 (s, 3H), 2.20 (s, 6H), 2.24 (t, 2H, J=7.2 Hz), 2.39 (m, 1H), 2.74 (dd, 1H, J=5.7, 13.8 Hz), 2.92 (dd, 1H, J=9.3, 14.0 Hz), 3.07 (dd, 1H, J=5.1, 13.9 Hz), 3.28 (dd, 1H, J=4.9, 14.1 Hz), 3.78 (m, 1H), 4.10 (br, 1H), 4.35–4.50 (m, 3H), 4.75 (d, 1H, J=3.7 Hz), 5.07 (septet, 1H, J=6.0 Hz), 6.87 (d, 1H, J=8.1 Hz), 7.13 (d, 1H, J=9.5 Hz), 7.2–7.35 (m, 5H).

According to Procedure B, 0.49 g of the free base was converted to the dihydrochloride (0.438 g, 85% washed with ether). FAB-MS m/e (relative intensity): 733 (100, MH+). HPLC (50/50): 1.65 minutes (89%).

Example 20

4-(2-Methoxyethylamino) piperidine-1-carbonyl-Phe -SMeCys-norCSta Isopropyl Ester 4-Piperidone-1-carbonyl-Phe-SMeCys-norCSta isopropyl ester (1.0 g) was reductively aminated with 2-methoxyethylamine hydrochloride according to Procedure A giving the title substance (0.89 g, 82%) as a colorless solid. $^1$H NMR (CDCl$_3$, 300 mHz, partial, ppm) delta: 1.26 and 1.27 (d, 3H ea, J=6.2 Hz), 2.08 (s, 3H), 2.92 (dd, 1H, J =9.1, 14.1 Hz), 3.07 (dd, 1H, J=5.1, 13.8 Hz), 3.27 (dd, 1H, J=5.2, 13.8 Hz), 3.33 (s, 3H), 3.46 (m, 2H), 3.69 (m, 2-3H), 4.10 (br, 1H), 4.36-4.50 (m, 3H), 4.77 (d, 1H, J=3.7 Hz), 5.06 (septet, 1H, J=6.0 Hz), 6.87 (d, 1H, J=8.1 Hz), 7.13 (d, 1H, J=9.4 Hz), 7.2-7.35 (m, 5H).

According to Procedure B, 0.89 g of the free base was converted to the hydrochloride (0.85 g, 91% washed with ether). FAB-MS m/e (relative intensity): 692 (75, MH+), 332 (43), 185 (45), 159 (100). HPLC (60/40): 2.59 minutes (94%).

Example 21

4-(4-Hydroxy-1-piperidino)piperidine-1-carbonyl-Phe -SMeCys-norCSta Isopropyl Ester 4-Piperidone-1-carbonyl-Phe-SMeCys-norCSta isopropyl ester (1.0 g) was reductively aminated with 4-hydroxypiperidine hydrochloride according to Procedure A giving the title substance (0.51 g, 45%) as a colorless solid. $^1$H NMR (CDCl$_3$, 300 mHz, partial, ppm) delta: 1.26 and 1.27 (d, 3H ea, J=6.2 Hz), 2.08 (s, 3H), 2.73 (dd, J=5.9, 13.9 Hz overlapping m, 3-4H total), 2.92 (dd, 1H, J=9.2, 14.1 Hz), 3.06 (dd, 1H, J=5.2, 13.8 Hz), 3.27 (dd, 1H, J=5.0, 14.2 Hz), 3.79 (m, 2H), 4.09 (d, 1H, J=2.3 Hz), 4.37-4.50 (m, 3H), 4.78 (d, 1H, J=4.0 Hz), 5.06 (septet, 1H, J=6.3 Hz), 6.86 (d, 1H, J=8.0 Hz), 7.07 (d, 1H, J=9.5 Hz), 7.2-7.35 (m, 5H).

According to Procedure B, 0.51 g of the free base was converted to the hydrochloride (0.474 g, 88% washed with ether). FAB-MS m/e (relative intensity): 718 (100, MH+), 330 (40), 185 (50), 148 (40). HPLC (60/40): 2.11 minutes (95%).

Example 22

4-(4-Methyl-1-piperazino)piperidine-1-carbonyl-Phe -SMeCys-norCSta Isopropyl Ester 4-Piperidone-1-carbonyl-Phe-SMeCys-norCSta isopropyl ester (0.80 g) was reductively aminated with N-methylpiperazine dihydrochloride according to Procedure A (except that 15 equivalents of sodium acetate was used) giving the title substance (0.64 g, 71%) as a colorless solid. $^1$H NMR (CDCl$_3$, 300 mHz, partial, ppm) delta: 1.26 and 1.27 (d, 3H ea, J=6.2 Hz), 2.08 (s, 3H), 2.30 (2, 3H), 2.92 (dd, 1H, J=9.1, 14.1 Hz), 3.07 (dd, 1H, J=5.2, 13.8 Hz), 3.27 (dd, 1H, J=5.0, 13.9 Hz), 3.80 (m, 2H), 4.09 (d, 1H), 4.36-4.50 (m, 3H), 4.80 (d, 1H, J=3.7 Hz), 5.06 (septet, 1H, J=6.2 Hz), 6.87 (d, 1H, J=8.0 Hz), 7.09 (d, 1H, J=9.4 Hz), 7.2-7.35 (m, 5H).

According to Procedure B, 0.641 g of the free base was converted to the dihydrochloride (0.59 g, 88% washed with ether). FAB-MS m/e (relative intensity): 718 (92), 717 (70, MH+), 357 (40), 329 (80), 184 (75), 139 (100). HPLC (50/50): 1.76 minutes (92%).

Example 23

3-Dimethylaminopyrrolidine-1-carbonyl-Phe-SMeCys-norCSta Isopropyl Ester

A. R,S-3-Pyrrolidinol-1-carbonyl-Phe Benzyll Ester

A solution of 22.9 g phenylalanine benzyl ester p-toluenesulfonate and 7.5 mL triethylamine in 40 mL dichloromethane was added dropwise over 30 minutes to a OC solution of imidazole (7.3 g) and carbonyldi- imidazole (9.6 g) in 60 mL dichloromethane. The mixture was stirred at 25° C. for 30 minutes and 3-pyrrolidinol (4.9 g) was added. After 2.5 hours in the mixture was diluted with 200 mL CHCl$_3$ and the solution washed with 3×100 mL 2N HCl, and then with brine and then dried. The solution was then concentrated giving 20.1 g of the title substance as a colorless solid.

B. 3-Pyrrolidone-1-carbonyl-Phe Benzyl Ester

A solution of 2.7 mL dimethylsulfoxide in 12 mL dichloromethane was treated at -70° C. with 2.0 mL oxalyl chloride. A solution of 7 g R,S-3-pyrrolidinol-1-carbonyl-Phe benzyl ester in 12 mL dry dichloromethane was added at −65° C. over 10 minutes and the mixture was stirred at −65° C. for 10 minutes and -40° C. for 30 minutes, and cooled to −78° C. 13.3 mL triethylamine was added, the mixture warmed to 25° C., diluted with 75 mL CHCl$_3$ and extracted with 3×50 mL 1N HCl, and then with brine and then dried. The solution was then concentrated to yield a solid which was then recrystallized from 1:1 dichloromethane-ether giving the title compound 1.68 g of an off-white solid (24%).

C. 3-Pyrrolidone-1-carbonyl-Phe

A solution of 1.57 g 3-pyrrolidone-1-carbonyl-Phe benzyl ester in 72 mL methanol and 8 mL acetic acid was shaken with 1.5 g 10% Pd/C for 1.5 hours under 50 p.s.i. hydrogen pressure. The mixture was filtered, the filtrate concentrated, and the residue coevaporated with added dichloromethane giving 1.28 g of the title compound as an off-white solid.

D. 3-Pyrrolidone-1-carbonyl-Phe-SMeCys-nor CStaIsopropyl Ester 225 mg of SMeCys-norCSta isopropyl ester hydrochloride (U.S. Pat. No. 4,814,342) and 0.204 g 3-pyrrolidone-1-carbonyl-Phe were coupled according to Procedure C. The crude product was purified by chromatography on silica packed and eluted with ethyl acetate-hexane (3:1), giving the title compound as an off-white foam (0.218 g, 61%).

E. 3-Dimethylaminopyrrolidine-1-carbonyl-Phe-SMeCys-norCSta Isopropyl Ester 3-Pyrrolidone-1-carbonyl-Phe-SMeCys-norCSta isopropyl ester (0.1 g) was reductively aminated with dimethylamine hydrochloride according to Procedure A giving the title substance (0.06 g, 57%) as a colorless solid. $^1$H NMR (CDCl$_3$, 300 mHz, partial, ppm) delta: 1.25 and 1.26 (d, 3H ea, J=6.2 Hz), 2.09 (s, 3H), 2.24 (s, 6H), 4.11 (d, 1H), 4.35-4.55 (m, 3-4H), 5.05 (septet, 1H, J=6.2 Hz), 6.93 (m, 1H), 7.15-7.35 (m, 6H).

According to Procedure B, 0.06 g of the free base was converted to the hydrochloride (0.019 g, 30% washed with ether). FAB-MS m/e (relative intensity): 648 (25, MH+), 288 (30), 260 (27), 141 (45), 115 (100). HPLC (60/40): 2.25 minutes (87%).

Example 24

4-Dimethylaminopiperidine-1-carbonyl -Phe-OEtSer-norCSta Isopropyl Ester

A. t-Butoxycarbonyl-OEtSer Dicyclohexylammonium Salt

Boc-L-serine (9.5 g, 0.0463 mol) was stirred in 125 mL dry dimethylformamide at 0°-5° C. while 60% sodium hydride dispersion in oil (5.55 g, 0.139 mol) was added in portions over 30 minutes. The resulting mixture was stirred at 0°-5° C. for 1.5 hours. Ethyl iodide (4.1 mL, 0.0507 mol) was added and the mixture was stirred at 25° C. for 15 hours. The mixture was poured into a stirred mixture of ethyl acetate (800 mL) and 1 N NaOH (200 mL), the layers separated, and the aqueous layer washed again with ethyl acetate. The aqueous layer was acidified and extracted repeatedly with ethyl acetate. These extracts were combined, washed with water, dried, and concentrated giving 9.25 g, 86% of the acid as an oil: $^1$H NMR (CDCl$_3$, 300 mHz, partial, ppm) delta: 1.17 (t, 3H, J=7.0 Hz), 1.44 (s, 9H), 3.52 (q, 2H, J=7.0 Hz), 3.63 (dd, 1H, J=4.1, 9.4 Hz), 3.88 (dd, 1H, J=6.2 Hz), 4.42 (br, 1H), 5.38 (d, 1H, J=7.5 Hz). The oil was dissolved in ether and 7.9 mL of dicyclohexylamine was added. The mixture was concentrated and dissolved in hexane and chilled to give a solid which was filtered and washed with hexanes (11.6 g, 71%).

B. Boc-OEtSer-norCSta Isopropyl Ester

Boc-OEtSer dicyclohexylammonium salt (5.0 g) was coupled to isopropyl 2R-hydroxy-3S-amino-4-cyclohexylbutanoate (norCSta isopropyl ester, 2.94 g, U.S. Pat. No. 4,814,342) according to Procedure C and the crude product purified by chromatography on silica packed and eluted with 1/5 (v/v) ethyl acetate-hexanes, giving 3.72 g (67%) of the title substance as a colorless foam, TLC Rf 0.42 (silica, 1:1 hexane:ethyl acetate). $^1$H NMR (CDCl$_3$, 300 mHz, partial, ppm) delta: 1.20 (t, 3H, J=7.0 Hz), 1.26 (d, 6H, J=6.3 Hz), 1.44 (s, 9H), 3.16 (d, 1H, J=4.7 Hz), 3.36 (dd, 1H, J=7.6, 8.7 HZ), 3.52 (q, 2H, J=7.0 HZ), 3.74 (dd, 1H, J =3.7, 9 HZ), 4.04 (dd, 1H, J=1.7, 5.0 Hz), 4.09 (br, 1H), 4.49 (m, 1H), 5.02 (septet, 1H, J=6.3 Hz), 5.39 (br, 1H), 6.55 (d, 1H, J=9.8 Hz). FAB-MS m/e (relative intensity): 459 (50, MH+), 483 (100), 359 (95).

C. OEtSer-norCSta Isopropyl Ester Hydrochloride

Boc-OEtSer-norCSta isopropyl ester (3.72 g) was deprotected according to Procedure D giving 3.46 g of the title substance as a colorless solid, TLC Rf 0.20 (silica, 18/2/1 HCCl$_3$/ethanol/acetic acid). $^1$H NMR (DMSO-d6, 300 mHz, partial, ppm) delta: 1.14 (t, 3H, J=7.0 Hz), 1.17 and 1.19 (d, 3H ea, J=6.0, 6.3 Hz), 3.47 (m, 2H), 3.65 (dd, 1H, J =3.5, 10.4 Hz), 4.01 (m, 2H), 4.21 (m, 1H), 4.83 (septet, 1H, J=6.2 Hz), 5.60 (d, 1H, J=5.2 Hz), 8.17 (br, 1H), 8.25 (d, 1H, J=9.1 Hz).

D. 4-Piperidone-1-carbonyl-Phe-OEtCys-norCsta Isopropyl Ester 2.18 g of OEtSer-norCSta isopropyl ester hydrochloride and 1.6 g 4-piperidone-1-carbonyl-Phe (U.S. Pat. No. 4,814,342) were coupled according to general procedure C. The crude product was purified by chromatography on 100 g silica packed and eluted with ethyl acetate-hexane (9:1), giving an off-white foam which was recrystallized from chloroform-hexane giving 1.44 g (41%) of a colorless solid, TLC Rf 0.22 (silica, ethyl acetate): HPLC (60/40): 4.37 minutes (99%). $^1$H NMR (CDCl$_3$, 300 mHz, partial, ppm) delta: 1.14 (t, 3H, J=7.0 Hz), 1.26 (d, 6H, J=6.2 Hz), 2.34 (m, 4H), 2.99 (dd, 1H, J=8.6, 14.1 Hz), 3.25 (dd, 1H, J=5.6, 14.0 Hz), 3.39 (dd, 1H, J=6.1, 9.1 Hz), 3.48 (q, 2H, J=7.0 Hz), 3.59 (m, 4H), 3.81 (dd, 1H, J=3.2, 9.1, Hz), 4.07 (dd, 1H, J=2.0, 7.4 Hz), 4.33 (m, 1H), 4.49 (m, 2H), 5.05 (m, 2H), 6.77 (m, 2H), 7.2–7.35 (m, circa 5H). FAB-MS m/e (relative intensity): 631 (65, MH+), 359 (95), 273 (72), 245 (100), 125 (88).

E. 4-Dimethylaminopiperidine-1-carbonyl-Phe-OEtCys-norCSta Isopropyl Ester

4-Piperidone-1-carbonyl-Phe-OEtSer-norCSta isopropyl ester (0.54 g) was reductively aminated with dimethylamine hydrochloride according to Procedure A giving 0.348 g of the title substance as a colorless solid (63% yield). $^1$H NMR (CDCl$_3$, 300 mHz, partial, ppm) delta: 1.13 (t, 3H, J=7.0 Hz), 1.25 and 1.26 (d, 3H ea, J=6.3 Hz), 2.25 (s, 6H), 2.73 (m, 1H), 2.93 (dd, 1H, J=9.1, 14.1 Hz), 3.27 (dd, 1H, J=5.0, 14.1 Hz), 3.41 (m, 1H), 3.46 (dq, 2H, J=1.4, 7.0 Hz), 3.87 (dd, 1H, J=3.0, 9.3, Hz), 4.09 (d, 1H), 4.4 (m, 2H), 4.5 (m, 1H), 4.84 (d, 1H), 5.06 (septet, 1H, J=6.2 Hz), 6.8 (d, 7.2 Hz), 7.01 (d, 1H, J=9.4 Hz), 7.2–7.35 (m, 5H).

According to Procedure B, 0.36 g of the free base was converted to the hydrochloride (0.30 g, 82%). FAB-MS m/e (relative intensity): 660 (100, MH+), 302 (41), 274 (40), 129 (90). HPLC (60/40): 2.34 minutes (98%).

Example 25

4-Dimethylaminopiperidine-1-carbonyl-Phe-SMeCys -norCStan-Propyl Ester

A. 4-Piperidone-1-carbonyl-Phe N-Hydroysuccinimide Ester

A solution of 4-Piperidone-1-carbonyl Phe (20 g, 0.069 mol), N-hydroxysuccinimide (7.93 g, 0.069 mol), and dicyclohexylcarbodiimide (14.1 g, 0.069 mol) was stirred in an ice bath which was allowed to warm to 25° C. overnight. The suspension was filtered, the filtrate concentrated, and the residue dissolved in ethyl acetate. The resulting solution was washed with aqueous NaHCO$_3$, and then with brine and then dried. The solution was then concentrated giving 25.6 g of the title compound as a solid (96%).

B. 4-Piperidone-1-carbonyl-Phe-SMeCys Dicyclohexyl-amine salt

A solution of 7.92 g of 4-piperidone-1-carbonyl- Phe N-hydroxysuccinimide ester in 22 mL tetrahydrofuran was added to a 25° C. solution of 4.14 g S-methylcysteine in 45 mL of saturated aqueous NaHCO$_3$. After 30 minutes, the pH was adjusted to 10.5 with 1N NaOH and the mixture was extracted with ethyl ether. The aqueous layer was acidified to pH 1 with HCl and extracted with chloroform. The chloroform layers were dried and concentrated giving 6.9 g of a solid which was chromatographed on 200 g silica packed in ethyl acetate, eluting with 1 L portions of 5% and 10% ethanol-ethyl acetate giving 5.5 g of impure solid. This material was dissolved in 80 mL dichloromethane and treated with 2.7 mL dicyclohexylamine and concentrated giving 7.9 g of solid. Two recrystallizations from etherdichloromethane gave 4.75 g (39%) of the title salt.

C. 4-Piperidone-1-carbonyl-Phe-SMeCys-norCSta methylester 1.44 g of norCSta methyl ester (U.S. Pat. No. 4,814,342) and 3.37 g 4-piperidone-1-carbonyl-Phe-S-MeCys dicyclohexylamine salt were coupled according to Procedure C. The crude product was purified by chromatography on 240 g silica packed and eluted with ethyl acetate-hexane (2:1), giving 2.2 g (64%) of the title ester. Anal.: Calc'd for C, 59.54%; H, 7.33%; N, 9.26%. Found: C, 59.44%, H, 7.30%; N, 8.94%.

D. 4-Piperidone-1-carbonyl-Phe-SMeCys-norCSta n-propyl ester

4-Piperidone-1-carbonyl-Phe-SMeCys-nor-CSta methyl ester (0.35 g) was stirred with 0.06 mL titanium tetraisopropoxide in 1 mL n-propyl alcohol at 100° C. for 1 hour, concentrated, and the mixture chromatographed on silica packed in 1:1 ethyl acetate:hexanes and eluted with 2:1, 3:1, 4:1 and 5:0 ethyl acetate: hexanes giving 0.272 g (74%) of the title substance as a colorless solid.

E. 4-Dimethylaminopiperidine-1-carbonyl-phe-SMeCys-norCSta n-propyl ester

4-Piperidone-1-carbonyl-Phe-SMeCys-norCSta n-propyl ester (0.13 g) was reductively aminated with dimethylamine hydrochloride according to Procedure A giving the title substance (0.084 g, 62%) as a colorless solid. $^1$H NMR (CDCl$_3$, 300 mHz, partial, ppm) delta: 0.94 (t, 3H, J=7.4 Hz), 2.09 (s, 3H), 2.33 (s, 6H), 2.95 (dd, 1H, J=9.2, 14.0 Hz), 3.03 (dd, 1H, J=5.2, 13.8 Hz), 3.27 (dd, 1H, J=9, 14.0 Hz), 3.82 (d, 2H, J=13.1 Hz), 4.10 (t, J=6.9 Hz overlapping s, 3H total), 4.37–4.45 (m, 3H), 4.87 (d, 1H), 6.92 (d, 1H, J=8.0 Hz), 7.05 (d, 1Hz, J=9.4 Hz), 7.2–7.35 (m, 5–6H).

According to Procedure B, 0.084 g of the free base was converted to the hydrochloride (0.56 g, 63%, washed with ether). HPLC (60/40): 3.29 minutes (93%).

Example 26
4-Dimethylaminopiperidine-1-carbonyl-Phe-Nle-norC-Sta Isopropyl Ester

A. Boc-Nle-norCSta Isopropyl Ester

Boc-Nle (3.64 g) was coupled to isopropyl 2R-hydroxy-3S-amino-4-cyclohexylbutanoate (norCSta isopropyl ester, 3.82 g, U.S. Pat. No. 4,814,342) according to Procedure C and the crude product purified by chromatography on silica packed and eluted with 1/4 (v/v) ethyl acetate/hexanes, giving 4.85 g (68%) of the title substance as colorless foam, TLC Rf 0.18 (silica, 4:1 hexane:ethyl acetate). $^1$H NMR (CDCl$_3$, 300 mHz, partial, ppm) delta: 0.88 (t, 3H, J=6.7 Hz), 1.26 and 1.27 (d, 3H ea, J=6.3 Hz), 1.43 (s, 9H), 3.18 (d, 1H, J=4.4 Hz), 3.91 (dt, 1H), 4.05 (dd, 1H, J=1.8, 4.4 Hz), 4.46 (dt, 1H), 4.89 (br, 1H), 5.03 (septet, 1H, J=6.3 Hz), 6.06 (d, 1H, J=9.7 Hz). FAB-MS m/e (relative intensity): 4.57 (54, MH+), 401 (100), 357 (88), 315 (25), 244 (36), 202 (43), 126 (60).

B. Nle-norCSta Isopropyl Ester Hydrochloride

Boc-Nle-norCSta isopropyl ester (4.80 g) was deprotected according to Procedure D giving 4.38 g of the title substance as a colorless solid, TLC Rf 0.33 (silica, 18/2/1 HCCl$_3$/ethanol/acetic acid). $^1$H NMR (DMSO-d6, 300 mHz, partial, ppm) delta: 0.87 (t, 3H), 1.17 and 1.18 (d, 3H ea, J=6.3 Hz), 3.74 (m, 1H), 4.01 (dd, 1H), 4.25 (dt, 1H), 4.83 (septet, 1H, J=6.3 Hz), 5.60 (d, 1H, J=5.2 Hz), 3.17 (br, 1H), 8.22 (d, 1H). FAB-MS m/e (relative intensity) 357 (100, MH+), 244 (33), 202 (20).

C. 4-Piperidone-1-carbonyl-Phe-Nle-norCSta Isopropyl Ester 2.18 g of Nle-norCSta isopropyl ester hydro- chloride and 2.33 g 4-piperidone-1-carbonyl-Phe (U.S. Pat. No. 4,814,342) were coupled according to Procedure C. The crude product was purified by chromatography on 100 g silica packed and eluted with ethyl acetate-hexane (7:3), giving a 1.83 g of an off-white foam which was recrystallized from chloroform-hexane giving 1.20 g (24%) of the title compound as a colorless solid, TLC Rf 0.44 (silica, ethyl acetate), mp 175°–176° C. $^1$H NMR (CDCl$_3$, 300 mHz, partial, ppm) delta: 0.85 (t, 3H, J=7.3 Hz), 1.26 (d, 6H, J=6.3 Hz), 2.36 (m, 4H), 3.03 (dd, 1H, J=7.9, 14.1 Hz), 3.17 (dd, 1H, J=6.0, 14.0 Hz), 3.53 (m, 3H), 3.64 (m, 2H), 4.10 (m, 1H), 4.21 (m, 1H), 4.45 (dt, 1H), 4.52 (m, 1H), 5.06 (septet, 1H, J=6.3 Hz), 5.10 (d, 1H, J=6.1 Hz), 6.35 (d, 1H, J=9.7 Hz), 7.51 (d, 1H, J=7.8 Hz), 7.2–7.32 (m, 5H). FAB-MS m/e (relative intensity): 629 (40, MH+), 357 (55), 273 (66), 245 (100), 202 (44), 126 (71). HPLC (60/40): 5.7 minutes.

D. 4-Dimethylaminopiperidine-1-carbonyl-Phe-Nle-norCStA Isopropyl Ester

4-Piperidone-1-carbonyl-Phe-Nle-norCSta isopropyl ester (0.45 g) was reductively aminated with dimethylamine hydrochloride according to Procedure A giving 0.362 g of the title substance as a colorless solid (77% yield). $^1$H NMR (CDCl$_3$, 300 mHz, partial, ppm) delta: 0.86 (t, 3H, J=7.2 Hz), 1.25 and 1.26 (d, 3H ea, J=6.2 Hz), 2.34 (s, 6H), 2.51 (m, 1H), 3.00 (dd, 1H, J=8.4, 14.1 Hz), 3.18 (dd, 1H, J=5.7, 14.1 Hz), 3.78 (d, 1H, J=13.2 Hz), 3.89 (d, 1H), 4.08 (d, 1H, J=2.5 Hz), 4.22 (m, 1H), 4.40 (m, 2H), 4.99 (d, 1H), 5.04 (septet, 1H, J=6.2 Hz), 6.54 (d, 1H, J=7.9 Hz), 6.65 (d, 1H, J=9.5 Hz), 7.2–7.33 (m, 5H). According to Procedure B, 0.36 g of the free base was converted to the hydrochloride (0.39 g, 96%). FAB-MS m/e (relative intensity): 658 (40, MH+), 302 (50), 274 (35), 155 (36), 129 (100). HPLC (60/40): 2.89 minutes (98%).

Example 27
4-Dimethylaminopiperidine-1-carbonyl-Phe-His-norCSta Isopropyl Ester

A. Boc-His-norCSta Isopropyl Ester

Diboc-His (3.50 g) was coupled to isopropyl 2R-hydroxy-3S-amino-4-cyclohexylbutanoate (norCSta isopropyl ester, 2.40 g, U.S. Pat. No. 4,814,342) according to Procedure C and the crude product purified by chromatography on silica packed and eluted with 1/1 (v/v) ethyl acetate-hexanes, giving 4.85 g (68%) of the title substance as an off-white foam, TLC Rf 0.2 (silica, 1:1 hexane:ethyl acetate). $^1$H NMR (CDCl$_3$, 300 mHz, partial, ppm) delta: 1.24 and 1.26 (d, 3H ea, J=6.2 Hz), 1.44 (s, 9H), 1.58 (s, 9H), 2.86 (dd, 1H, J=6.0, 14.9 Hz), 3.03 (dd, 1H, J=4.8, 14.9 Hz), 3.68 (br, 1H), 4.0 (d, 1H), 4.29 (dt, 1H), 4.39 (dt, 1H), 5.01 (septet, 1H, J=6.3 Hz), 6.18 (d, 1H, J=7.2 Hz), 7.17 (s, 1H), 8.01 (s, 1H).

B. His-norCSta Isopropyl Ester Dihydrochloride

Diboc-His-norCSta isopropyl ester (3.30 g) was dissolved at 0° C. in 25 mL trifluoroacetic acid, stirred 2 hours at 0° C., and evaporated. The residue was dissolved in 15 mL 4M HCl-dioxane and evaporated, and the residue washed with ether on a filter and dried giving 2.62 g (100%) of the title substance as an off-white powder. $^1$H NMR (DMSO-d6, 300 mHz, partial, ppm) delta: 1.16 and 1.17 (d, 3H ea, J=6.2 Hz), 3.08 (d, 1H, J=8.2, 15.8 Hz), 3.24 (dd, 1H, J=4.8, 15.8 Hz), 4.00 (d, 1H, J=2.9 Hz), 4.23 (d, 2H), 4.78 (septet, 1H, J=6.3 Hz), 7.5 (s, 1H), 9.09 (2, 1H), 14.5 (br, 1H).

C. 4-Piperidone-1-carbonyl-Phe-His-norCSta Isopropyl Ester 1.60 g of His-norCSta isopropyl ester dihydrochloride and 1.03 g 4-piperidone-1-carbonyl-Phe (U.S. Pat. No. 4,814,342) were coupled according to general Procedure C. The crude product was purified by chromatography on 80 g silica packed with 2% ethanol-dichloromethane and eluted with 1 L each of 2%, 4%, 10% and 20% ethanol-dichloromethane, giving 1.05 g (46%) of an off-white foam. $^1$H NMR (CDCl$_3$, 300 mHz, partial, ppm) delta: 1.24 and 1.28 (d, 3H ea, J=6.2 Hz), 2.34 and 2.43 (m, 3H ea), 2.79 (dd, 1H), 2.95 (dd, 1H, J=4.0, 14.0 Hz), 3.57 (m, 4H), 4.05 (d, 1H, J=2.3 Hz), 4.35 (m, 1H), 4.43 (m, 1H), 4.57 (m, 1H), 5.06 (septet, 1H, J=6.2 Hz), 5.21 (d, 1H), 6.80 (s, 1H), 6.90 (d, 1H), 7.21–7.37 (m, 6H). HPLC (60/40): 2.21 minutes (98%).

D. 4-Dimethylaminopiperidine-1-carbonyl-Phe-His-norCSt a-Isopropyl Ester

4-Piperidone-1-carbonyl-Phe-His-norCSta isopropyl ester (0.395 g) was reductively aminated with dimethylamine hydrochloride according to Procedure A giving 0.190 g of the title substance as a colorless solid (46% yield). $^1$H NMR (CDCl$_3$, 300 mHz, partial, ppm) delta: 1.24 and 1.26 (d, 3H ea, J=6 Hz), 2.27 (s, 6H), 2.6–2.95 (m, 3–4H), 3.15–3.35 (overlapping dd, 2H), 3.7 (d, 1H), 3.8 (d, 1H), 4.06 (d, 1H, J=2.7 Hz), 4.35 (m, 2H), 4.59 (m, 1H), 5.07 (septet, 1H, J=6.2 Hz), 6.78 (s, 1H), 7.04 (d, 1H, J=9.3 Hz), 7.2–7.34 (m, 5–6H), 7.57 (s, 1H), 8.1 (br, 1H).

According to Procedure B, 0.19 g of the free base was converted to the dihydrochloride (0.181 g). FAB-MS m/e (relative intensity): 682 (100, MH+), 381 (25). HPLC (40/60): 2.32 minutes (97%).

Example 28

4-Dimethylaminopiperidine-1-carbonyl-Phe-L-allylglycine-norCSta Isopropyl Ester Hydrochloride

A. Boc-L-allylglycine-norCSta Isopropyl Ester

Boc-L-allylglycine (450 mg) and norCStaOiPr (535 mg) were coupled according to Procedure C and the product purified by silica gel chromatography (1:1 v/v EtOAc/hexanes) to afford 593 mg (64%) of the title compound, TLC Rf 0.73 (EtOAc).

B. L-allylglycine-norCSta Isopropyl Ester Hydrochloride

The title compound of Example 28A (490 mg) was deprotected according to Procedure D to yield 390 mg of the title compound as a colorless solid.

C. 4-Piperidone-1-carbonyl-Phe-L-allyglycine-norCSta Isopropyl Ester

The title compound of Example 28B (305 mg) and 258 mg 4-piperidone-1-carbonyl-Phe were coupled according to Procedure C. The product was purified by trituration from hot isopropyl ether/ethyl acetate to to yield 230 mg (44%) of the title compound.

D. 4-Dimethylaminopiperidine-1-carbonyl-Phe-L-allylglycine-norCSta Isopropyl Ester According to Procedure A, 200 mg of the title compound of Example 28° C. aminated with dimethylamine hydrochloride to afford 146 mg of the title compound.

E. 4-Dimethylaminopiperidine-1-carbonyl-Phe-L-allylglycine-norCSta Isopropyl Ester Hydrochloride According to Procedure B, 146 mg of the title compound of Example 28D was converted to the hydrochloride salt. After filtration from ether, 137 mg of the title compound was obtained as a pale yellow solid (86%). HPLC (70/30): 2.54 minutes (97%). FAB-MS (m/e) (relative intensity): 642.5 (MH+), 302.2, 274.3. $^1$H NMR (CD3OD, 300 mHz, partial) delta 1.25 (d, J=6.2 Hz, 3H), 1.29 (d, J=7.4 Hz, 3H), 1.90 (m, 1H), 2.45 (m, 1H), 2.52 (m, 1H), 2.81 (br s, 6H), 2.90 (dd, J=10.9, 14.1 Hz, 1H), 4.09 (d, J=2.4 Hz, 1H), 5.00 (m, 1H), 5.10 (m, 2H), 5.80 (m, 1H), 7.20 (m, 5H).

Example 29

4-(1-Pyrrolidinyl)piperidine-1-carbonyl-Phe-L-allylglycine-norCSta Isopropyl Ester 4-Piperidone-1-carbonyl-Phe-L-allylglycine-norCStaisopropyl ester (100 mg) was treated with pyrrolidine and sodium cyanoborohydride according to Procedure A. The free amine was then converted to its hydrochloride salt according to Procedure B to provide 46 mg (41%) of the title compound as a pale yellow powder. HPLC(70/30): 3.09 minutes (92%). FAB-MS (m/e) (relative intensity): 668.5 (MH+), 328.2, 300.3. $^1$H NMR (CDCl$_3$, 300 mHz, partial) delta: 1.24 (d, J=6.3 Hz, 3H), 1.26 (d, J=6.1 Hz, 3H), 2.80 (m, 2H), 2.94 (dd, J=8.6, 14.1 Hz, 1H)), 3.20 (dd, J=5.3 Hz, 14.1 Hz, 1H), 3.50 (m, 1H), 3.70 (m, 2H), 4.10 (m, 1H), 4.82 (d, J=4.0 Hz, 1H), 5.10 (m, 2H), 5.60 (m, 1H), 6.41 (d, J=7.0 Hz, 1H), 6.89 (d, J=9.4 Hz, 1H), 7.30 (m, 5H).

Example 30

(4-(4-Dimethylamino)-1-piperidino)-2R-benzylsuccinoyl -SMeCys-norCSta Isopropyl Ester

A. 1-benzyl 4-(4-piperidone)-2R-benzylsuccinate

1-Benzyl 2R-benzylsuccinate (prepared as described by J. Plattner et al. (J. Med. Chem., 31, 2277, (1988)) (1.82 g) and 4-piperidone monohydrate hydrochloride (1.03 g) were coupled according to Procedure C to give 2.08 g (90%) of the title compound.

B. 4-(4-piperidone)-2R-benzylsuccinoyl-SMeCys-norCSta Isopropyl Ester

Catalytic hydrogenation of the title compound of Example 30A (1.90 g) with Pd(OH)2 in ethanol (45 PSI H$_2$, 16 hours) afforded 760 mg (53%) of the free acid. The crude acid was then coupled with SMeCys-norC- Sta Isopropyl Ester according to Procedure C to give after silica gel chromatography (ethyl acetate), 405 mg (27%) of the title compound.

C. 4-(4-Dimethylamino)-1-piperidino)-2R-benzylsuccinoyl-SMeCys-norCSta Isopropyl Ester According to Procedure A, the title compound of Example 30B (105 mg) was reductively aminated with dimethyl amine hydrochloride to give the title compound. FAB-MS m/e (relative intensity): 661.3 (MH+), 301.2. $^1$H NMR (CDCl$_3$, 300 mHz, two rotamers) delta: 1.22 (d, 3H), 1.23 (d, 3H), 2.23 (s, 1.5H), 2.24 (s, 1.5H), 3.70 (m, 1H), 4.05 (d, 1H), 4.52 (m, 1H), 5.00 (septet, 1H), 6.66 (d, 0.5H), 6.70 (d, 0.5H), 6.74 (d, 0.5H), 6.72 (d, 0.5H), 7.20 (m, 6H). HPLC (70/30): 3.05 minutes (95%). The free amine was converted to the hydrochloride salt according to Procedure B (62 mg, 37%).

Example 31
4-Dimethylaminopiperidine-1-carbonyl-3-L-phenyl-lactyl-SMeCys-norCSta Isopropyl Ester

A. 4-Piperidone-1-carbonyl-3-L-phenyllactic acid

To a stirred solution of imidazole (691 mg) and 1,1'-carbonyldiimidazole (843 mg) in 20 mL of dry methylene chloride at 0° C., benzyl-L-3-phenyllactate (1.30 g) in 5 mL of methylene chloride was added dropwise. After being stirred for 15 minutes at 0° C., the solution was warmed to 23° C. and stirred for an additional 1 hour. A solution of piperidone monohydrate hydrochloride (780 mg) and triethylamine (564 mg) in 5 mL of methylene chloride was added in a single portion, and the reaction mixture stirred for 18 hours. The mixture was diluted with ethyl acetate (150 mL), and extracted with 1N sodium hydroxide, water, and brine and then dried (MgSO4) and concentrated. The crude product was purified by silica gel chromatography (ethyl acetate/hexanes 25:75) to give 1.60 g (83%) of the benzyl ester. The ester was treated with hydrogen (45 PSI) and Pd(OH)$_2$ (100 mg) in ethanol for 16 hours, filtered through diatomaceous earth (Celite(trade- mark)), and concentrated to give 1.00 g (72%) of the title compound. $^1$H NMR (CDCl$_3$) delta: 2.40 (m, 4H), 3.18 (dd, 1H), 3.32 (dd, 1H), 3.70 (m, 4H), 5.17 (dd, 1H), 6.80 (br. s, 1H), 7.25 (m, 5H).

B. 4-Piperidone-1-carbonyl-3-L-phenyllactyl-SMeCys-norCSta Isopropyl Ester

The title compound of Example 31A (422 mg) and SMeCys-norCSta Isopropyl Ester (575 mg) were coupled according to Procedure C to give after silica gel-chromatography (ethyl acetate/hexanes 1:1), 390 mg (42%) of the title compound. $^1$H NMR (CDCl$_3$, 300 mHz, partial) delta: 1.22 (d, 3H), 1.24 (d, 3H), 2.16 (s, 3H), 2.45 (dd, 1H), 2.95 (dd, 1H), 3.16 (dd, 1H), 3.33 (dd, 1H), 4.10 (m, 1H), 4.45 (m, 2H), 5.02 (septet, 1H), 5.32 (dd, 1H), 6.52 (d, 1H), 6.86 (d, 1H), 7.25 (m, 5H).

C. 4-Dimethylaminopiperidine-1-carbonyl-3-L-phenyl-lactyl-SMeCys-norCSta Isopropyl Ester The title compound of Example 31 B (228 mg) was reductively aminated with dimethylamine hydrochloride according to Procedure A to give 145 mg of the title compound. FAB-MS (m/e) (relative intensity): 663 (MH+), 300,275. $^1$H NMR (CDCl$_3$, partial) delta: 1.22 (t, 6H), 3.10 (dd, 1H), 3.18 (m, 1H), 4.40 (m, 2H), 5.02 (septet, 1H), 5.17 (m, 1H), 6.65 (m, 2H), 7.25 (m, 6}{). The free base was converted to its hydrochloride salt according to Procedure B to give a colorless solid (132 rag, 55%).

Example 32
4-(1-Pyrrolidinyl)piperidine-1-carbonyl-Phe-Serine-norCSta Isopropyl Ester

A. Boc-Ser-norCSta Isopropyl Ester 1.05 g of Boc-Ser and 1.30 g of norCSta Isopropyl Ester were coupled according to Procedure C, and the product purified by silica gel chromatography (ethyl acetate) to give 1.86 g of the title compound (93%).

B. 4-Piperidone-1-carbonyl-Phe-Ser-norCSta Isopropyl Ester 1.86 g of the title compound of Example 32A was deprotected according to Procedure D to give 1.47 g of a colorless solid. This material was coupled with 1.38 g of 4-piperidone-1-carbonyl-Phe according to Procedure D to afford 1.24 g (47%) of a colorless solid after silica gel chromatography (ethyl acetate/methanol, 95: 5). 1H NMR (CDCl$_3$, partial) delta: 1.25 (d, 6H), 3.0 (dd, 1H), 3.18 (dd, 1H), 3.88 (dd, 1H), 4.10 (m, 2H), 4.40 (m, 2H), 4.55 (m, 1H), 5.02 (septet, 1H), 5.45 (d, 1H), 7.02 (d, 1H), 7.22 (m, 6H). FAB-MS (m/e) (relative intensity): 603 (MH+), 33, 273, 245.

C. 4-(1-Pyrrolidinyl)piperidine-1-carbonyl-Phe-Ser-norCSta Isopropyl Ester 182 mg of the title compound of Example 32B was reductively aminated with pyrrolidine according to Procedure A to give 125 mg of the title compound after silica gel chromatography (10% methanol/ethylacetate). The free base was converted to the hydrochloride salt according to Procedure B (105 mg, 50%). FAB-MS (m/e) (relative intensity): 659 (MH$_2$+), 328, 300. $^1$H NMR (CD$_3$OD, 300 mHz, partial) delta: 1.21 (d, 3H), 1.22 (d, 3H), 2.60 (m, 4H), 2.70 (m, 2H), 2.90 (dd, 1H), 3.20 (dd, 1H), 3.40 (dd, 1H), 5.00 (septet, 1H), 5.30 (d, 1H), 7.24 (m, 5H).

Example 33
4-(bis-(2-methoxyethyl)-amine)piperidine-1-carbonyl-Phe-SMeCys-norCSta Isopropyl Ester According to Procedure A, 4-Piperidone-1-carbonyl-Phe-SMeCys-norCSta Isopropyl Ester (734 mg) was reductively aminated with bis-(2-methoxyethyl)-amine to give 120 mg (15%) of the title compound. FAB-MS (m/e) (relative intensity): 750.3 (MH+), 390.1, 362.1. $^1$H NMR (CDCl$_3$D, 300 mHz, partial) delta: 1.25 (d, 3H), 1.28 (d, 3H), 2.10 (s, 3H), 2.92 (dd, 1H), 3.13 (dd, 1H), 3.30 (s, 6H), 3.38 (t, 4H), 5.00 (m, 2H), 6.96 (d, 1H), 7.20 (d, 1H), 7.24 (m, 5H). The free base was converted to the hydrochloride salt according to Procedure B to give a colorless solid (110 mg, 91%).

Example 34
2-(4-Morphollno)ethyl-1-amino-1-carbonyl-Phe-SMeCys-norCSta Isopropyl Ester

A. 2-(4-Morphollno)ethyl-1-amino-1-carbonyl-Phe

Phe-benzyl ester isocyanate (420 mg) and 4-(2-aminoethyl) morpholine were dissolved in 15 mL of methylene chloride and stirred at 23° C. for 16 hours. The mixture was diluted with 50 mL of ethyl acetate and washed with 1N NaOH and then brine. The solution was then dried ($K_2CO_3$) and concentrated to give 500 mg of the benzyl ester. The crude ester was deprotected by catalytic hydrogenation ($H_2$, 45 PSI, Pd(OH)$_2$, ethanol 1% acetic acid). After 16 hours, the mixture was filtered through diatomaceous earth (Celite (trademark)) and concentrated to yield 291 mg (32%) of the title compound. $^1$H NMR (CD$_3$OD), delta: 2.90 (m, 3H), 3.00 (m, 4H), 3.05 (dd, 1H), 3.50 (m, 2H), 3.80 (m, 4H), 4.35 (m, 1H), 7.20 (m, 5H).

B. 2-(4-Morpholino)ethyl-1amino-1-carbonyl-Phe-SMe-Cys-norcsta Isopropyl Ester

L-SMeCys-norCSta Isopropyl Ester hydrochloride (396 mg) and 2-(4-Morpholino) ethyl-1-amino-1-carbonyl-Phe (291 mg) were coupled according to Procedure C and the product chromatographed (silica gel, methanol/ethyl acetate, 5:95) to give 190 mg of the free base. FAB-MS (m/e) (relative intensity): 664.2 (MH$_2$+), 244.2, 157.0. $^1$H NMR (CD$_3$OD, 300 mHz, partial) delta: 1.30 (d, 6H), 2.10 (s, 3H), 2.45 (m, 5H), 2.75 (dd, 1H), 2.98 (dd, 1H), 3.22 (m, 2H), 3.65 (m, 4H), 4.10 (d, 1H), 5.00 (septet, 1H), 6.88 (d, 1H), 6.90 (d, 1H), 7.25 (m, 6H). The free amine was converted to its hydrochloride salt according to Procedure B to give 170 mg (32%) of a colorless solid. HPLC (70/30): 2.97 minutes (92%).

Example 35

2-(4-Morpholino)propyl-1-amino-1-carbonyl-Phe-SMe-Cys-norCSta Isopropyl Ester

A. 2-(4-Morpholino)propyl-1-amino-1-carbonyl-Phe

According to the procedure described in Example 34A, the title compound was prepared from 340 mg of 4-(3-aminopropyl)morpholine and 640 mg of Phe-benzyl ester isocyanate to give 763 mg (80%) of the free acid. $^1$HNMR (CDCl$_3$, 300 mHz, partial) delta: 1.78 (m,2H), 2.90 (m, 6H), 3.05 (m, 3H), 3.20 (dd, 1H), 3.75 (t, 1H), 3.80 (m, 4H), 4.43 (m, 1H), 6.05 (m, 1H), 7.20 (m, 5H).

B. 2-(4-Morpholino)propyl-1-amino-1-carbonyl-Phe-SMeCys-norCSta Isopropyl Ester

According to Procedure C, the title compound of Example 35A (763 mg) and SMeCys-norCSta isopropyl ester (766 mg) were coupled to give the title compound as a colorless foam. FAB-MS (m/e): (relative intensity): 678.4 (MH+), 171.1 $^1$H NMR (CDCl$_3$, partial) delta: 1.22 (d, 3}{), 1.23 (d, 3H), 2.07 (s, 3H), 2.45 (m, 4H), 2.70 (dd, 1H), 3.08 (dd,1H), 3.22 (m, 2H), 4.10 (m, 1H), 4.50 (m, 2H), 5.10 (septet, 1H), 6.95 (d, 1H), 7.25 (m, 6H).

The free amine was converted to the hydrochloride salt of the title compound according to Procedure B to give 536 mg (40%) of a colorless solid. HPLC (70/30): 3.00 minutes (94%).

Example 36

(1-Dimethylamino)-cyclohexane-4-carbonyl-Phe-SMe-Cys-norCSta Isopropyl Ester

A. 1-Cyclohexanone-4-carbonyl-Phe-SMeCys-norCSta Isopropyl Ester

According to Procedure C, 1-cyclohexanone-4-carboxylic acid (320 Mg) and Phe-SMeCys-NorCSta Isopropyl Ester (1.23 g) were coupled and purified by crystallization (hot isopropyl ether/ethyl acetate) to give 950 mg (67%) of the title compound. FAB-MS (m/e) (relative intensity): 632.3 (MH+), 361.2, 244.3. $^1$H NMR (CDCl$_3$, 300 mHz, partial) delta: 1.25 (d, 6H), 2.65 (dd, 1H), 2.90 (dd, 1H), 3.08 (dd, 1H), 3.20 (dd, 1H), 4.10 (m, 1H), 4.70 (q, 1H), 5.07 (septet, 1H), 6.12 (m, 1H), 6.50 (d, 1H), 6.80 (m, 1H), 7.25 (m, 5H).

B. (1-Dimethylamino)-cyclohexane-4-carbonyl-Phe-SMe-Cys-norCSta Isopropyl Ester

According to Procedure A, 300 mg of 1-cyclohexanone-4-carbonyl-Phe-SMeCys-norCSta Isopropyl Ester was reductively aminated with dimethylamine hydrochloride to give a 1:1 mixture of the cis and trans cyclohexane isomers. Purification by silica gel chromatography (ethyl acetate/methanol, 85:15) failed to resolve the two isomers. FAB-MS (m/e) (relative intensity) 661.3 (MH+), 154.1, 119.9. $^1$H NMR (CDCl$_3$, 300 mHz, partial, two isomers) delta: 1.30 (d, 6H), 2.09 (s, 3H), 2.19 (s, 3H), 2.24 (s, 3H), 2.68 (m, 1H), 3.00 (m, 2H), 3.20 (m, 1H), 4.10 (d, 1H), 4.65 (q, 1H), 5.05 (septet, 1H), 6.61 (d, 0.5H), 6.62 (d, 0.5H), 6.78 (d, 0.5H), 6.80 (d, 0.5H), 7.25 (m, 6H).

The free amine was converted to the hydrochloride salt of the title compound according to Procedure B to give 200 mg (61%) of a colorless solid. HPLC (60/40): 4.24 and 5.46 minutes (96%, 1:1 ratio).

Example 37

4-(1-Pyrrolidinyl)piperidine-1-carbonyl-Phe-SMeCys-2S-amino-1-cyclohexyl-(3R, 4S)-dihyroxy-6-methylheptane A. Boc-SMeCys-2S-amino-1-cyclohexyl-(3R, 4S) dihydroxy-6-methylheptane 2S-amino-1-cyclohexyl-(3R, 4S)-dihydroxy-6-methylheptane (prepared as described by J. Luly et al. (J. Med. Chem., 31, 2264 (1988)) (476 mg) and Boc-SMeCys (420 mg) were coupled according to Procedure C to give 343 mg (43%) of the title compound after crystal- lization from hot isopropyl ether/hexanes. $^1$H NMR (CDCl$_3$, 300 mHz, partial) delta: 0.89 (d, 3H), 0.92 (d, 3H), 1.44 (s, 9H), 1.95 (m, 1H), 2.15 (s, 3H), 2.88 (d, 2H), 3.22 (d, 2H), 3.32 (m, $^1$H), 4.03 (d, 1H), 4.22 (q, 1H), 4.40 (m, 1H), 5.32 (d, 1H), 6 . 3 0 (d, 1H).

B. 4-Piperidine-1-carbonyl-Phe-SMeCys-2S-amino-1-cyclohexyl-(3R, 4S)-dihydroxy-6-methylheptane The title compound of Example 37A (340 mg) was deprotected according to Procedure D. The resulting hydrochloride salt was coupled with 4-piperidone-1-carbonyl-Phe (236 mg) according to Procedure C to give 240 mg (51%) of the title compound after purification by silica gel chromatography (ethyl acetate/hexanes, 80:20). FAB-MS (m/e): 634 (MH+), 361, 274, 244. $^1$H NMR (CDCl$_3$, 300 mHz, partial) delta: 0.94 (dd, 6H), 2.12 (s, 3H), 2.90 (dd, 1H), 3.20 (m, 2H), 3.40 (m, 2H), 4.03 (d, 1H), 4.32 (m, 1H), 4.42 (m, 1H), 4.58 (q, 1H), 4.90 (d, 1H), 6.95 (d, 1H), 7.30 (m, 6H).

C. 4-(1-Pyrrolidinyl)piperidine-1-carbonyl-Phe-SMeCys-2S-amino-1-cyclohexyl-(3R, 4S)-dihydroxy-6methylheptane 4-Piperidine-1-carbonyl-Phe-SMeCys-2S-amino-1-cyclohexyl-(3R, 4S)-dihydroxy-6-methylheptane (149 mg) was reductively aminated with pyrrolidine according to Procedure A to give, after silica gel chromatography (ethyl acetate/methanol, 80:20), 150 mg of the title compound: FAB-MS (m/e): 688.7 (MH+), 328.3, 300.3. $^1$H NMR (CDCl$_3$, 300 mHz, partial) delta: 0.94 (d, 6H), 2.23 (s, 3H), 2.55 (m, 4H), 2.80 (m, 2H), 3.20 (dd,1H), 3.40 (dd, 1H), 4.18 (m, 1H), 4.40 (m, 1H), 4.82 (d, 1H), 6.95 (d, 1H), 7.30 (m, 7H).

The free amine was then converted to its hydrochloride salt according to procedure B to provide 145 mg (83%) of the salt as a pale yellow powder.

Example 38

4-Trimethylammoniopiperidine-1-carbonyl-Phe-SMe-Cys-norCSta Isopropyl Ester Iodide

4-Dimethylaminopiperidine-1-carbonyl-Phe-SMe-Cys-norCSta Isopropyl Ester (100 mg) was dissolved in 3.5 mL acetonitrile at 25C and treated with 19 uL (2 equivalents) methyl iodide. After 45 minutes, the solution was evaporated and the solid residue washed on the filter with ethyl ether and dried giving 109 mg of a colorless solid, HPLC (60/40): 1.41 minutes (27%, iodide) and 2.46 minutes (70%). $^1$H NMR (300 mHz, CH$_3$OH-d4, partial, ppm) delta: 1.26 (d, 6H, J=6.3 Hz), 2.13 (s, 3H), 3.07 (s, 9H), 4.12 (d, 1H, J=2.7 Hz), 5.00 (septet, 1H, J=6.3 Hz). FAB-MS (m/e) (relative intensity): 676.3 (200, M for the cation).

The compounds of Examples 1 to 38 were tested for inhibition of human plasma renin activity at pH 7.4 using the renin inhibition assay described above on pages 44–46. All of the compounds had an IC$_{50}$ less than 50 nanomolar.

Using the procedures of Examples 6B/6C, substituting the appropriate statines (EP 332008, Example 12 and Example 13) for nor CSta isopropyl ester and SMe-Cys for OMeTyr, followed by the use of the procedure of Example 30, the following analogs were synthesized.

TABLE

| Example | R | R$^1$ | FAB (M + H)$^+$ * | $^1$H NMR (CDCl$_3$) (δ) (Partial) ≠ |
|---|---|---|---|---|
| 39 | cyclohexyl | cyclopropyl | 645.4 | 0.10–0.65(m, 2 5H), 2.05(s, 3H), 2.22(d, 6H), 6.85(m, 1H) |
| 40 | cyclohexadienyl | isobutyl | | 0.90(m, 6H), 2.05(s, 3H), 2.24(s, 6H), 5.50(br.s, 1H), 5.61(br.s, 2H) |
| 41 | cyclohexenyl | isobutyl | 659.4 | 0.92(m, 6H), 2.05(s, 3H), 2.24(d, 6H), 5.50(br.s, 1H) |

*FAB on Hydrochloride Salts For Final Products of examples 39–82
≠NMR On Free Bases for Final Products of examples 39–82

Using the Procedure of Example 11, substituting the appropriate amino acid for OMeTyr, the following analogs were prepared:

TABLE

| Example | R | MS FAB(M + H)$^+$ | $^1$H NMR(CDCl$_3$) (δ) (Partial) |
|---|---|---|---|
| 42 | thienyl | 668.4 | 1.23(2d's, 6H), 2.07(s, 3H), 2.20(s, 6H), 7.20(m, 3H) |
| 43 | thienyl | | 1.23(2d's, 6H), 2.02(s, 3H), 2.20(s, 6H), 5.02(m, 1H), 7.00(m, 3H) |

TABLE -continued (Me)₂N-piperidine-C(=O)-NH-CH(CH₂R)-CO—SMECys—NORCSta—O—iPr

| Example | R | MS FAB(M + H)+ | ¹H NMR(CDCl₃) (δ) (Partial) |
|---------|---|----------------|------------------------------|
| 44 | 2-naphthyl | 712.5 | 1.30(2d's, 6H), 2.05(s, 3H), 2.17(s, 6H), 5.05(m, 1H), 6.70(d, 1H) |
| 45 | 1-naphthyl | | 1.20(2d's, 6H), 1.97(s, 3H), 2.05(s, 6H), 6.95(d, 1H), 6.09(d, 1H) |
| 46 | phenyl | 676.1 | 1.24(2d's, 6H), 2.10(s, 3H), 2.41(s, 6H), 5.02(m, 1H) |

Using the procedures of Example 6, substituting SMeCys for OMeSer and the appropriate nor CSta Amide (Example 50) for nor CSta isopropyl ester, the following analogs were synthesized:

TABLE (Me)₂N-piperidine-C(=O)-N-Phe—SMECys—NORCSta—R

| Example | R | FAB | ¹H NMR |
|---------|---|-----|--------|
| 47 | NH-CH₂-(2-pyridyl) | 710.5 | 2.05(s, 3H), 2.24(s, 6H), 7.62(m, 2H), 8.50(d, 1H) |
| 48 | NH-CH₂-CF₃ | | 2.09(s, 3H), 2.30(s, 6H), 4.85(m, 1H), 7.30(m, 5H) |
| 49 | NH-CH₂CH₂-morpholino | 732.9 | 2.01(s, 3H), 2.20(s, 6H), 2.40(m, 4H), 3.80(m, 4H), 7.20(m, 5H) |

Example 50

A. nor CSta—2'-aminomethylpyridyl amide hydrochloride

To a solution of BOC nor CSta acid (U.S. Pat. No. 4,599,198), 150.5 mg (0.5 mmol), in 15 ml of methylene chloride was sequentially added 54 mg (0.5 mmol) of 2-aminomethylpyridine, 67.5 (0.5 mmol of N-hydroxybenztriazole and 103 mg (0.5 mmol) of dicyclohexylcarbodiimide- After stirring at room temperature overnight, the reaction mixture was filtered and evaporated to dryness. The residue was dissolved in ethylacetate, filtered and the resulting solution washed with saturated aqueous NaHCO₃, brine, and dried over anhydrous MgSO₄, to yield 256 mg of the BOC derivative of title compound as a foam, which was converted to 200 mg of the title substance as a foam by the use of Procedure D. ¹H NMR (CD₃OD) (partial): 8.10 (d, 1H, J=8 H$_z$).

B. Using the previous procedure the following analogous substances were prepared using the appropriate amine.

TABLE

HCl.NH₂-CH(cyclohexylidene-CH₂-)-CH(OH)-C(=O)-R

R:
- NH-CH₂-CF₃
- NH-CH₂CH₂-morpholino

Using the procedure of Example 6, substituting SMeCys for OMeSer and the appropriate nor CSta ester (Example 59) for nor CSta isopropyl ester, the following analogs were synthesized:

TABLE (Me)₂N-piperidine-C(=O)-N-Phe—SMECys—NORCSta—R

| Example | R | FAB | ¹H NMR |
|---------|---|-----|--------|
| 51 | O-CH(CF)(F) (difluoro) | | 2.10(s, 3H), 2.30(s, 6H), 4.70(m, 4H), 7.30(m, 5H) |

TABLE-continued (Me)₂N-piperidine-C(=O)-Phe—SMECys—NORCSta—R

| Example | R | FAB | ¹H NMR |
|---|---|---|---|
| 52 | O—(2-methylcyclohexyl) | | 0.95(2d's, 3H), 2.04(s, 3H), 2.22(s, 6H), 7.30(m, 5H) |
| 53 | O—(2,6-dimethylcyclohexyl) | | 0.92(2d's, 6H), 2.10(s, 3H), 2.30(s, 6H), 7.30(m, 5H) |
| 54 | O—cyclopentyl | | 2.10(s, 3H), 2.30(s, 3H), 5.20(m, 1H), 7.20–7.40(m, 5H) |
| 55 | O—(2-methylcyclopentyl) | | 1.00(2d's, 3H), 2.10(s, 3H), 2.25(s, 6H), 7.15–7.35(m, 5H) |
| 56 | O—isopropyl(ish) | | 0.75(m, 6H), 2.05(s, 3H), 2.20(s, 6H), 7.15–7.35(m, 5) |
| 57 | O—(2,2-dimethylcyclopentyl) | 716.5 | 1.00(4s's, 6H), 2.10(s, 3H), 2.35(s, 6H), 5.00(m, 1H), 7.30(m, 5H) |
| 58 | O—(2,4-dimethylcyclopentyl) | 716.3 | 1.05(2d's, 6H), 2.10(s, 3H), 2.25(s, 6H), 4.80(m, 1H), 7.40(m, 5H) |

Example 59

A. nor CSta-trans-2'-trans-5'-dimethylcylopentyl ester hydrochloride

Nor CSta methyl ester hydrochloride (U.S. Pat. No. 4,814,342), 200 mg, was slurried in 1.5 g of trans-2-trans-5-dimethylcyclopentanol (L. Brener; H. C. Brown; J. Org. Chem. 1977, 42, 2702). The slurry was saturated with anhydrous HCl gas at 25° and then heated to 90°100° overnight. After being allowed to cool to room temperature, the reaction mixture was diluted with ether and the resulting solid collected to afford 215 mg of the title compound as a white amorphous solid. ¹H NMR (DMSO-d6) (partial): 0.95 (2d's, 6H), 2.95 (m, 2H), 4.03 (t, 1H), 4.26 (t, 1H).

B. Employing the previous procedure the following related substances were prepared in an analogous manner using the appropriate alcohols:

TABLE

Cyclohexyl-CH(NH₂·HCl)-CH(OH)-C(=O)-R

| R |
|---|
| O—cyclopentyl |
| O—CF₂ (gem-difluoro) |
| O—cyclobutyl |
| O—(2-methylcyclopentyl) |
| O—cyclohexyl |
| O—(2-methylcyclohexyl) |
| O—(2,6-dimethylcyclohexyl) |
| O—(2,4-dimethylcyclopentyl) |
| O—(3-methylcyclopentyl) |
| O—(2,2-dimethylcyclopentyl) |

Using the procedures of Examples 6B/6C, substituting the appropriate nor CSta ester (Example 50) for nor CSta isopropyl ester, followed by the use of the procedure of Example 30, the following analogs were synthesized:

TABLE

[Structure: (CH3)2N-piperidine-N-C(=O)-CH(CH2Ph)-CO—SMECys—NORCSta—R]

| Example | R | FAB | ¹H NMR |
|---|---|---|---|
| 60 | O-cyclopentyl | | 2.12(s, 3H), 2.32(s, 6H), 5.14(br.s, 1H), 7.30(m, 5) |
| 61 | O-cyclobutyl (t-Bu) | | 0.90(m, 6H), 2.11(s, 3H), 2.25(d, 6H), 4.70 (m, 1H), 7.30(m, 5H) |
| 62 | O-(2-methylcyclopentyl) | 701 | 0.90(2d's, 6H), 2.15 (s, 3H), 2.40(S, 6H), 4.80 (m, 1H) |
| 63 | O-(2,3-dimethylcyclopentyl) | 715.6 | 1.05(2d's, 6H), 2.12 (s, 3H), 2.25(s, 6H), 4.10 (m, 1H), 7.25(m, 5H) |
| 64 | O-(2,4-dimethylcyclopentyl) | | 1.0(m, 6H), 2.10(s, 3H), 2.27(s, 6H), 4.30(m, 5) |
| 65 | O-(gem-dimethylcyclopentyl) | 715.4 | 0.97(4s's, 6H), 2.12 (s, 3H), 2.25(d, 6H), 7.30 (m, 5H) |

Employing the procedure of Examples 30A/30B, substituting either 3-dimethylamino azetidine or 3-piperidino azetidine (Japan; 74,109,369; A. G. Anderson; R. Lok; J. Org. Chem. 1972, 3.5, 3953) for 4-piperidone, the following analogs were synthesized:

TABLE

[Structure: R-azetidine-N-C(=O)-CH(CH2Ph)-CO—SMECys—NORCSta—O-tBu]

| Example | R | FAB | ¹H NMR |
|---|---|---|---|
| 66 | (CH3)2N— | 633.3 | 1.55(d, 6H), 2.10(s, 3H), 2.15(s, 6H), 5.0(m, 1), 7.30(m, 5H) |
| 67 | piperidino— | | 1.25(d, 6H), 2.70(m, 2H), 5.00(m, 1H), 7.25(m, 5H) |

Using the procedures of Example 11A-E, substituting 1-naphthylalanine for Phe, and subsequently using the procedure of Example 11G, substituting either N-methyl ethanolamine or N-methyl-N'-BOC ethylene diamine for dimethylamine, the following analogs were synthesized:

TABLE

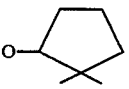

[CH3(R)N-piperidine-N-C(=O)-[1-NAPHTHYLALANINE]-SMECys—NORCSta—O-tBu]

| Example | R | FAB | ¹H NMR |
|---|---|---|---|
| 68 | —CH2CH2OH | 742.4 | 1.25(2d's, 6H), 2.05(s, 3H), 2.15(s, 3H), 5.05(m, 1H) |
| 69 | —CH2CH2NH2* | 666.6 | 1.15(d, 6H), 2.10(s, 3H), 2.65 (s, 3H), 4.80(m, 1H), 7.85(d, 1H) |

*After The Use Of Procedure D On The BOC Precursor

Using the procedure of Example 11, substituting the appropriate amino acid for OMeTyr and piperidine for dimethylamine in Step G, the following analogs were prepared.

TABLE

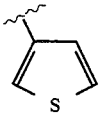

[piperidino-piperidine-N-C(=O)-NH-CH(R)-C(=O)—SMeCys—NOR CSta—O-tBu]

| Example | R | FAB | ¹H NMR |
|---|---|---|---|
| 70 | 3-thienylmethyl | 708.4 | 1.30(2d's, 6H), 2.10(s, 3H), 2.48(m, 4H), 7.35(t, 1H) |

TABLE-continued

[Structure: piperidine-N-piperidine-NH-C(=O)-CH(R)-C(=O)-SMeCys-NOR CSta-O-iPr]

| Example | R | FAB | ¹H NMR |
|---------|---|-----|--------|
| 71 | 2-naphthyl | 752.6 | 1.21(2d's, 6H), 2.01(s, 3H), 2.35(m, 4H), 6.95(d, 1H) |
| 72 | -CH₂CH₂-phenyl | 716.4 | 1.21(2d's, 6H), 2.06(s, 3H), 2.20(m, 4H), 7.15-7.30(m, 5H) |

Example 73

4-(1-Dimethylamino.)piperidine-1-carbonyl-3-thienylalanine-SMeCys-2S-amino-1-cyclohexyl-(3R,4S)-dihydroxy-6-methyl-Heptane Using the procedure of Example 37, substituting 3thienylalanine for Phe and dimethylamine for pyrrolidine in Step C, the title compound was synthesized: ¹H NMR(CDCl₃): 2.09(S,3H), 2.24(S,6H), 2.79(d,3H), 5.80(m,1U), 6.10(m,1H), FAB(M+H)+668.4.

Using the procedure of Example 6, substituting SMeCys for OMeSer, the appropriate statine ester (Example 59) for nor CSta isopropyl ester and, in Step E, piperidine for dimethylamine, the following analogs were synthesized:

TABLE

[Structure: piperidine-N-piperidine-N-C(=O)-Phe-SMeCys-NH-CH(CH₂-cyclohexyl)-CH(OH)-C(=O)-R]

| Example | R | FAB | ¹H NMR |
|---------|---|-----|--------|
| 74 | O-cyclopentyl | | 2.06(s, 3H), 2.50(m, 4H), 5.35(m, 1H), 7.20-7.40(m, 5H) |
| 75 | O-(2-methylcyclopentyl) | 742.4 | 1.00(2d's, 3H), 2.10(s, 3H), 4.80(m, 1H), 7.20-7.45(m, 5H) |

Using the procedure of Example 6, substituting SMeCys for OMeSer, either OMeTyr or hexahydroPhe for Phe, and the appropriate statine ester (Example 59) for nor CSta isopropyl ester, the following analogs were prepared.

TABLE

[Structure: Me₂N-piperidine-N-C(=O)-NH-CH(CH₂R)-CO-SMeCys-NH-CH(CH₂-cyclohexyl)-CH(OH)-C(=O)-R¹]

| Example | R | R¹ | FAB | ¹H NMR |
|---------|---|----|----|--------|
| 76 | cyclohexyl | O-isopropyl | | 0.90(m, 6H), 2.15(s, 3H), 2.40(s, 6H), 4.80(m, 1H) |
| 77 | cyclohexyl | O-(2-methylcyclopentyl) | | 1.00(2d's, 3H), 2.10(s, 3H), 2.22(d, 6H), 4.72(m, 1H), 7.30(m, 5H) |

TABLE-continued

[Structure: (CH3)2N-piperidine-C(O)-NH-CH(R)-CO-SMeCys-NH-CH(CH2-cyclohexyl)-CH(OH)-C(O)-R1]

| Example | R | R¹ | FAB | ¹H NMR |
|---|---|---|---|---|
| 78 | cyclohexyl | O-(2,2-dimethylcyclopentyl) | | 0.90(4s's, 6H), 2.09(s, 3H), 2.29 (s, 6H), 2.92(m, 2) |
| 79 | 4-OCH₃-phenyl | O-cyclobutyl | | 0.90(m, 6H), 2.10(s, 3H), 2.30 (s, 6H), 3.80(s, 3H), 6.85(d, 2H), 7.15(d, 2m) |
| 80 | 4-OCH₃-phenyl | O-cyclopentyl | | 2.05(s, 3H), 2.40(s, 6H), 3.75 (s, 3H), 6.85(d, 2H), 7.20(d, 2H) |
| 81 | 4-OCH₃-phenyl | O-(2-methylcyclopentyl) | | 1.00(2d's, 3H), 2.15(s, 3H), 2.30 (s, 6H), 4.85(m, 1H) |
| 82 | 4-OCH₃-phenyl | O-(2,2-dimethylcyclopentyl) | 746.4 | 1.00(4's, 6H), 2.10(s, 3H), 2.30 (s, 6H), 3.80(s, 3H), 6.88(d, 2H), 7.15(d, 2H) |

Example 83

9-Fluorenylmethylenoxycarbonyl-S-methyl-L-cysteine

Reaction of N-(9-Fluorenylmethylenoxycarbonyloxy) succinimide with S-methyl-L-cysteine according to the reported procedure (J. Org. Chem. 1972, 37, p3404) gave the title substance in 99% yield. FAB-MS m/e (rel intensity) 358 (25, M++H), 179 (100). ¹H NMR (CDCl₃, partial) δ 2.15 (s, 3H), 3.0 (m, 2H), 4.22 (t, 1H), 4.42 (d, 2H), 4.64 (q, 2H), 4.70 (d, 1H).

Example 84

A compound of formula X, where R₄=CH₂SCH₃, R₅=cyclohexyl, and R₆=

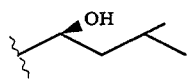

N-(9-Fluorenylmethylenoxycarbonyl)-S-methyl-L-cysteine (2.20 g) and 2(S)-amino-1-cyclohexyl-(3R, 4S)-dihydroxy-6-methylheptane (1.50 g) were coupled according to General Procedure C (above) and the crude product triturated with ethyl acetate giving 2.4 g of the FMOC-protected dipeptide which was dissolved in methanol (35 ml). A large excess of dimethylamine was introduced at 0° C. and the resulting mixture stirred at 25° C. until deprotection was complete (3h). Evaporation gave a colorless solid which was washed with hexane and dried giving the title substance (1.15 g). ¹H NMR (CDCl₃, partial) δ 0.86 (d, 3H), 0.93 (d, 3H), 2.11 (s, 3H), 2.72 (dd, 1H), 2.96 (dd, 1H), 3.22 (m, 2H), 3.59 (dd, 1H), 4.27 (dt, 1H), 7.47 (d, 1H).

In directly analogous fashion, except that the trituration solvents were varied as appropriate, or trituration replaced by column chromatography on silica gel in a suitable solvent system, the following compounds of general formula X were also prepared by coupling FMOC-S-methylcysteine with the requisite amines:

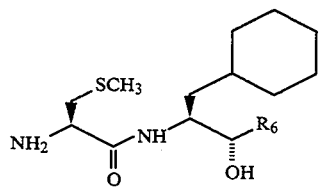

| Example # | R6 | FAB-MS Base Peak M+ + H (%) | 1H NMR (CDCl3, partial) δ |
|---|---|---|---|
| 85 | ⟨S-S⟩ | 379 (100) | CDCl3, 0.90(m, 2H), 2.10(s, 3H), 2.67(dd, 1H), 2.98(dd, 1H), 3.17(m, 4H), 3.36(dd, 1H), 3.55(dd, 1H), 4.28(m, 1H), 4.38(d, 1H) |
| 86 | ⟨S-S⟩ | 393 (100) | CDCl3 0.93(m, 2H), 2.11(s, 3H), 3.63(d, 1H), 3.84(dd, 1H), 4.52(q, 1H), 7.54(d, 1H) |
| 87 | ⟨O-O⟩ | 347 (100) | DMSO-D6 2.03(S, 3H), 4.62(d, 1H) |
| 88 | ⟨O-O⟩ | 361 (100) | CDCl3 2.10(s, 3H), 2.65(dd, 1H), 2.99(dd, 1H), 3.51(ddd, 1H), 3.75(m, 1H), 4.37(d, 1H) 7.50(d, 1H) |

Example 89

2S-(N-t-Boc-amino)-3(R),4(S)-dihydroxy-6-methyl-1-phenyl-heptane

A solution of 3(S)-(Boc-amino)-2(R)-hydroxy-4-phenylbutyronitrile (U.S. Pat. No. 4,599,198, 50 g) in 650 ml ethyl ether was treated dropwise at reflux with 600 ml 2.0M isobutylmagnesium bromide and the mixture stirred at reflux for 1 hour. The mixture was poured onto ice and extracted with ether giving after drying and concentration the corresponding isobutyl ketone as an oil which crystallized on standing. THF(1 L) and ethanol (0.25 L) were added and the solution treated at 0° C. with 19.2 g NaBH4. After being stirred overnight the mixture was partially concentrated, poured into 1L of ice water, treated with 10% aqueous citric acid, and the solution extracted repeatedly with ethyl acetate. The organic layers were washed with saturated aqueous NaHCO3 and dried giving 58 g of a colorless solid which was crystallized from 1:4 ethyl acetate—hexanes. The solid was recrystallized from the same solvent giving 20.3 g of the title substance, mp 139°–140° C., [α]D20—56.4° (C=1, CHCl3).

Example 90

2 (S)-Amino-3(R), 4(S)-dihydroxy-6-methyl-1-phenylheptane

The product of the preceding example (6.0 g) was dissolved in trifluoroacetic acid (25 ml) at 0° C., stirred 20 minutes at this temperature, and concentrated. The residue was dissolved in 5 ml of 4M HCl-dioxane, and the solution evaporated, giving a colorless solid which contained the title hydrochloride and the corresponding trifluoroacetamide derivative. Acid-base extraction provided 2.09 g of the title substance as a colorless solid. FAB-MS 238 (100%, M+ +H).

Example 91

4-Ketopiperidine-1-carbonyl-p-IodoPhe

According to the conditions of Procedure D, 1.45 g of 4-ketopiperidine-1-carbonyl-p-IodoPhe benzyl ester gave 1.45 g of a colorless solid which was purified by chromatography on silica eluting with an ethanol-dichloromethane gradient giving 1.03 g of the title substance, CI-MS 417 (M+ +H).

Example 92

4-Ketopiperidine-1-carbonyl-hexahydro-L-phenyllactic acid

A solution of the methyl ester of the title substance (9.7 g) in 100 ml THF and 50 ml water was treated at 0° C. with 7.8 ml of 6N NaOH for 2 h, concentrated, diluted with 250 ml water, and extracted with ether. The aqueous layer was acidified and extracted with ethyl acetate giving a colorless oil which crystallized on standing (8.73 g). 1H NMR (CDCl3, partial) 6 3.68 (br, 2H), 3.93 (br, 2H), 5.07 (dd, 1H). FAB-MS 298 (100%, M+ +H).

Example 93

4-Dimethylaminopiperidine-1-carbonyl-O-MeTyr Hydrochloride

By the method of Example 11E, 1.36 g of 4-dimethylaminopiperidine-1-carbonyl-O-MeTyr benzyl ester was hydrogenated and further converted to the hydrochloride by coevaporation with 3.2 mL of added 1N HCl. The residue was washed with ether and dried giving the title substance as a colorless solid (1.28 g). $^1$H NMR (CD3OD, partial) 2.82 (s, 6H), 3.75 (s, 3H), 4.17 (m, 2H), 4.42 (dd, 1H), 4.97 (s, 2H), 6.86 (d, 2H), 7.13 (d, 2H). The following examples were prepared by coupling of the indicated intermediate of general formula

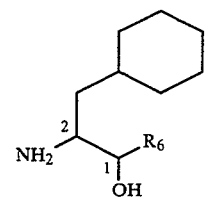

with 1 equivalent 4-[4-dimethylaminopiperidine-1-carbonyl]-2(R)-benzyl-1-succinoyl-S-MeCys at 0° C. using 1.1 equivalent triethylamine and 1.1 equivalent diethlyphosphoryl cyanide in dichloromethane, with workup and purification as described in procedure C.

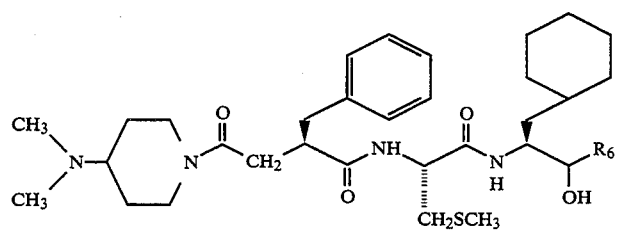

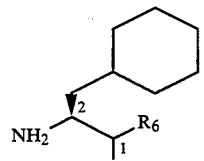

| Example | Y | Isomer used as starting material | FAB-MS Base, M$^+$ + H (%) | $^1$HNMR (CDCl$_3$, partial) δ |
|---|---|---|---|---|
| 94 | N⟩—⟨S (thiazole) | More polar[1], 1S, 2S stereochemistry | 301 (100) 658 (92) | CDCl$_3$ 2.11 and 2.12(s, 3H total), 2.29 and 2.30(s, 6H total), 4.2(m, 1H), 5.05(m, 1H) |
| 95 | N(CH$_3$)—S | Less polar[a] | 301 (100) 686 (83) | CDCl$_3$ 2.07 and 2.08(s, 3H total), 2.23, 2.25, 2.26, and 2.27(s, 3H ea), 3.72(m, 2H), 4.21(m, 2H), 4.35(m, 1H), 4.52(m) |
| 96 | N—S(CH$_3$) dimethyl thiazole | More polar[b] | 301 (100) 686 (60) | CDCl$_3$ 2.10 and 2.11(s, 3H total), 2.22, 2.23, 2.26, and 2.28(s, 3H ea), 3.72(d, 1H) |
| 97 | N(CH$_3$)—S | Less polar[a] | 301 (100) 672 (100) | CDCl$_3$ 2.06 and 2.07(s, 3H total), 2.23, 2.25, and 2.40(s, 3H ea), 3.72(d, 1H), 4.9(t, 1H) |
| 98 | N—S—H | More polar[b] | 301 (100) 672 (60) | CDCl$_3$ 2.09 and 2.10(s, 3H total), 2.23 and 2.24(s, 6H total), 2.39 and 2.40(s, 3H total) |
| 99 | H—N—S | Less polar[a] | 672 (100) | CDCl$_3$ 2.03 and 2.04(s, 3H total), 2.22 and 2.24(s, 6H total), 2.39(S, 3H), 4.85(m, 1H) |
| 100 | N—S—CH$_3$ | More polar[b] | 672 (100) | CDCl$_3$ 2.09 and 2.10(s, 3H total), 2.23, 2.25 and 2.4(s, 3H ea) |
| 101 | N(CH$_3$)—S(vinyl) | less polar[2] | 119 (100) 698 (25) | CDCl$_3$ 0.85(m, 2H), 2.02,(s, 3H) 2.31 and 2.33(s, 6H total), 4.82(d, 1H), 5.14(d, 1H), 5.35(d, 1H) |
| 102 | benzothiazole | less polar[a] | 119 (100) 708 (42) | CDCl$_3$ 1.97 and 1.98(s, 3H total), 2.26(s, 6H total), 3.72(d, 1H), 4.37(m, 2H), 4.52(m, 1H), 5.02(m, 1H) |

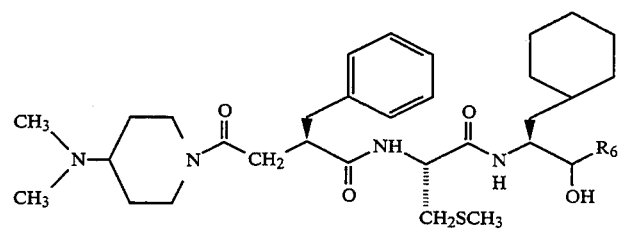

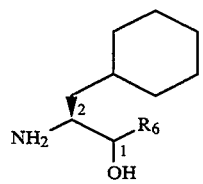

| Example | Y | Isomer used as starting material | FAB-MS Base, M+ + H (%) | ¹HNMR (CDCl₃, partial) δ |
|---|---|---|---|---|
| 103 | OH, CF₂CF₃ | 1R, 2S Stereochemistry | 301 (100) 723 (90) | CDCl₃ 2.03 and 2.06(3H total), 2.25 and 2.26(s, 6H total), 3.82(br, 1H), 4.24(m, 1H), 4.48(m, 1H) |
| 104 | N, N-OCH₂Ph | 1R, 2S Stereochemistry (EP 337 295) | 761 (100) | CDCl₃ 2.07 and 2.08(s, 3H total) 2.23, (s, 6H total) 4.42(s, 2H), 5.22(d, 1H), 5.55(d, 1H) |

ᵃin 1821/1 HCCl₃/EtOH/NH₄OH on silica gel compared to the isomeric substance (less polar = faster moving);
ᵇBoc analog identical to the compound described previously as having the (R) stereochemistry (EP 337 295, p. 50, Squibb), at this stereocenter.

Example 105

2,5-diaza-5-methyl-bicyclo [4.3.0] nonane a) N-(t-BOC)-3-allyl-4-piperidone

A stirred solution of N-(t-BOC)-piperidone (6 g) and allyl alcohol (3 g) in 40 mL of benzene was heated at a reflux for 16 hours in an apparatus connected to a Dean-Stark water separator filled with 4° seives. The reaction was cooled to room temperature and concentrated in vacuo. Xylenes (50 mL) were added and the reaction was brought to reflux for an additional 4 hours. After cooling, the reaction was concentrated and the residue was chromatographed (Amicon matrix silica SI (trademark), 30 μM) to give 5.6 g of the title compound. ¹H-NMR (CDCl₃, 300 MHz) δ 1.50 (s, 9H), 2.12 (m, 1H), 2.50 (m, 4H), 3.02 (m, 1H), 3.38 (m, 1H), 4.08 (m, 2H), 5.03 (m, 2H), 5.78 (m, 1H).

b) 2-BOC-2,5-diaza-5-methylbicyclo[4.3.0]nonane

The above compound (5.6 g) was dissolved in CH₂Cl₂ (60 mL), cooled to −78° C. and ozone introduced until a blue solution resulted. Nitrogen was passed through the solution to remove the excess ozone, and then methyl sulfide (3 mL) was added. The reaction was warmed to room temperature, stirred overnight, and concentrated. The crude oil was reductively aminated with methylamine according to procedure A to give after chromatography (Amicon matrix silica SI (trademark), 30 μM) 720 mg of the title compound. H-NMR (CD₃OD, 300 MHz) 6 1.49 (s, 9H), 1.50 (m, 2H), 1.74 (m, 1H), 1.92 (m, 1H), 2.05 (m, 1H), 2.47 (m, 1H), 2.50 (s, 3H), 2.52 (m, 1H), 2.70 (m, 1H), 3.20 (m, 2H), 3.48 (m, 1H), 3.60 (dd, 1H). FAB-MS 241 (MH+), 185.

c) 2,5-diaza-5-methyl-bicyclo [4.3.0] nonane

The above compound was deprotected according to procedure D to give the title as compound the dihydrochloride salt.

Example 106

4-(dimethylaminomethyl) piperidine a) BOC-(4-formyl) piperidine

To a stirred solution of methoxymethyl-triphenylphosphonium chloride (9.6 g) in 75 mL of dry THF, 3.5 g of potassium tert-butoxide was added. The solution was stirred for 2 hours, and 5.6 g of N-t-BOC-4-piperidone was added. After stirring for 16 hours the brown reaction mixture was quenched with 1N NaOH, diluted with ethyl acetate, and extracted with saturated sodium bicarbonate, brine, dried (MgSO₄) and concentrated. The residue was triturated with ether/hexanes (1:1) and the solid removed by filtration. The mother liquor was concentrated and purified (Amicon matrix silica SI (trademark), 30 μM) to give 5.1 g of the methyl enol ether. This material was dissolved in 40 mL of THF and 2 mL of concentrated HCl was added. The reaction was stirred for 1 hour, diluted with ethyl acetate, extracted with 0.5N NaOH, brine, dried (Na₂SO₄) and concentrated. Purification (Amicon matrix silica SI (trademark), 30 μM) provided 3.90 g of the title compound. ¹H NMR (CDCl₃, 300 MHz) 6 1.43 (s, 9H), 1.60 (m, 2H), 1.90 (m, 2H), 2.39 (m, 1H), 2.90 (m, 2H), 3.97 (m, 2H), 9.64 (s, 1H).

b) BOO-(4-(dimethylaminomethyl)piperidine

According to procedure A, 652 mg of the above compound was reductively aminated with dimethylamine hydrochloride to afford 656 mg of the title compound. $^1$H NMR (CDCl$_3$, 300 MHz) δ 1.12 (m, 2H), 1.49 (s, 9H), 1.66 (m, 1H), 1.75 (m, 2H), 2.12 (d, 2H), 2.22 (s, 6H), 2.69 (m, 1H), 4.10 (m, 2H).

c) 4-(dimethylaminomethyl)piperidine

According to procedure D, 346 mg of the above compound was deprotected to give the dihydrochloride salt of the title compound.

Example 107

4-(1-piperidinomethyl)piperidine

According to the procedure described in Example 106b, 638 mg of N-t-BOC-(4-formyl) piperidine was reductively aminated with piperidine and deprotected to give the title compound.

Example 108

4-(BOC-(N-methyl)aminomethyl)piperidine a)
1-Benzyl-4-(BOC-(N-methyl)aminomethyl)piperidine 1-benzyl-4-formyl piperidine (1.13 g) and 1 g of 4 Å seives were added to 30 mL of a 2:1 mixture of benzene and methanol at 0° C. Methylamine gas was introduced into the system with a sparge tube for 15 minutes. The solution was stirred at 0° C. for an additional 30 minutes and then concentrated. The residue was dissolved in methanol, cooled to 0° C., and NaCNBH$_3$ (700 mg) was added in one portion. The mixture was warmed to room temperature and stirred for 3 hours. After filtering through a pad of celite, the mixture was concentrated, diluted with ethyl acetate, extracted with 1N NaOH, brine, dried (K$_2$CO$_3$) and concentrated to give 1.20 g of a yellow oil. The crude amine was dissolved in a 2:1 mixture of dioxane/water, and di-tert-butyl-dicarbonate (1.12 g) was added. The pH of the solution was maintained at pH 10-11 by the addition of 1N NaOH. After 2 hours, the dioxane was removed in vacuo, and the residue extracted 2× with ethyl acetate. The combined organic layers were washed with 1N NaOH, brine, dried (K$_2$CO$_3$) and concentrated. Purification (Amicon matrix silica SI (trademark), 30 μM) gave 0.80 g of the title compound. H-NMR (CDCl$_3$, 300 MHz) δ 1.32 (m, 2H), 1.45 (s, 9H), 1.62 (m, 2H), 2.00 (m, 2H), 2.84 (s, 3H), 2.92 (m, 2H), 3.09 (d, 2H), 3.49 (s, 2H). FAB-MS: 319 (MH+).

b) 4-(N-t-BOC-(N-methyl) aminomethyl)piperidine

The above compound (0.80 g) was dissolved in 10 mL of methanol and added to 50 mL of a 5% formic acid solution in methanol which contained 375 mg of palladium black. The reaction was stirred under nitrogen for 36 hours, filtered, and concentrated. The residue was taken up in methyl acetate and extracted with 1N NaOH, brine, dried (Na$_2$SO$_4$) and concentrated to give 0.59 g of the title compound as a colorless oil. $^1$H NMR (CD$_3$OD, 300 MHz) δ 1.14 (m, 2H), 1.43 (s, 9H), 1.61 (m, 2H), 1.77 (m, 1H), 2.53 (tit, 2H), 2.82 (s, 3H), 3.03 (m, 2H), 3.12 (m, 2H).

Example 109 a) 4-(2-(4-morpholino)ethyl-1-N-methylamino)-(2R)benzylsuccinnic acid 1-monobenzyl ester 2(R)-benzylsuccinate 1-monobenzyl ester (700 mg) and 4-(2-(N-methyl)-aminoethyl) morpholine (372 mg) were coupled according to procedure C to give 518 mg of the title compound. H-NMR (CDCl$_3$, 300 MHz, partial) δ 2.40 (m, 4H), 2.50 (4H), 2.90 (s, 3H), 3.10 (m, 1H), 3.30 (m, 1H), 3.67 (m, 4H), 5.10 (ABq, 2H), 7.20 (m, 10H).

b) 4-(2,5-diaza-5-methyl-bicyclo[4.3.0]nonane)-(2R)benzylsuccinnic acid 1-monobenzyl ester According to procedure C, 2,5-diaza-5-methyl-bicyclo [4.3.0] nonane (390 mg) and 2(R)-benzylsuccinnic acid 1-monobenzyl ester (551 mg) were coupled to give 360 mg of the title compound. $^1$H NMR (CDCl$_3$, 300 MHz, partial) 1.36 (m, 2H), 1.75 (m, 5H), 2.30 (s, 3H), 2.72 (m, 2H), 2.80 (m, 2H), 3.71 (m, 1H), 3.93 (m, 1H), 3.93 (m, 1H), 5.02 (m, 1H), 5.22 (m, 1H).

Using the previous procedure, the following analogous substances were prepared by coupling the appropriate amine with 2(R)-benzylsuccinnic acid 1-monobenzyl ester.

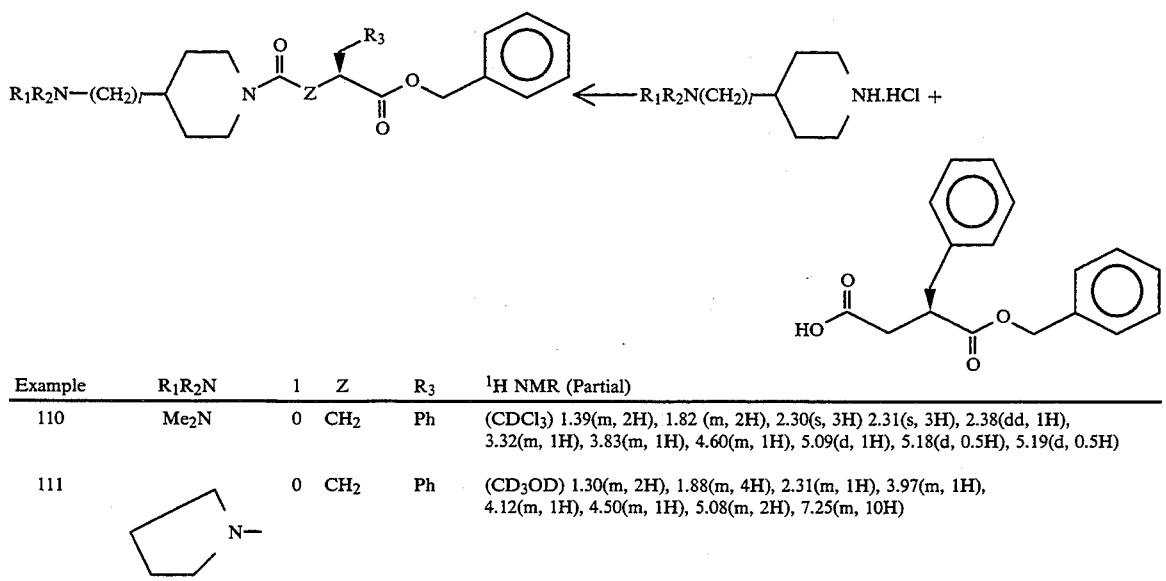

| Example | R$_1$R$_2$N | 1 | Z | R$_3$ | $^1$H NMR (Partial) |
|---|---|---|---|---|---|
| 110 | Me$_2$N | 0 | CH$_2$ | Ph | (CDCl$_3$) 1.39(m, 2H), 1.82 (m, 2H), 2.30(s, 3H) 2.31(s, 3H), 2.38(dd, 1H), 3.32(m, 1H), 3.83(m, 1H), 4.60(m, 1H), 5.09(d, 1H), 5.18(d, 0.5H), 5.19(d, 0.5H) |
| 111 | ⟨N—⟩ | 0 | CH$_2$ | Ph | (CD$_3$OD) 1.30(m, 2H), 1.88(m, 4H), 2.31(m, 1H), 3.97(m, 1H), 4.12(m, 1H), 4.50(m, 1H), 5.08(m, 2H), 7.25(m, 10H) |

| | | | | | |
|---|---|---|---|---|---|
| 112 | [piperidine-N—] | 0 | CH₂ | Ph | (CDCl₃) 2.38(dd, 1H), 2.79(dd, 1H), 3.04(dd, 1H), 3.37(m, 1H), 3.81(m, 1H), 4.62(m, 1H), 5.10(d, 1H), 5.17(d, 0.5H), 5.19 (0.5H) |
| 113 | (CH₃)₂N | 1 | CH₂ | Ph | (CDCl₃) 2.12(d, 2H), 2.23(s, 6H), 2.72(dd, 1H), 3.11(dd, 1H), 3.30(m, 1H), 3.87(m, 1H), 4.56(m, 1H), 5.09(d, 1H), 5.17(m, 1H) |
| 114 | [piperidine-N—] | 1 | CH₂ | Ph | (CDCl₃) 1.03(m, 2H), 2.10(d, 2H), 2.72(dd, 1H), 3.33(m, 1H), 3.64(m, 1H), 4.53 (m, 1H) 5.01(d, 1H), 5.13(d, 0.5H), 5.15 (d, 0.5H) |
| 115 | CH₃(t-BOC)N | 1 | CH₂ | Ph | (CDCl₃) 1.10(m, 2H), 1.62(m, 2H), 2.38(dd, 1H), 2.53(m, 1H), 3.30(m, 1H), 3.78(m, 1H), 4.50(m, 1H), 5.02(d, 1H), 5.13(d, 1H) |
| 116 | [piperidine-N—] | 0 | CH₂ | [cyclohexyl] | (CDCl₃) 0.88(m, 2H), 2.40(dd, 1H), 2.71(m, 1H), 2.92(m, 1H), 3.95 (m, 1H), 4.63(m, 1H), 5.03(d, 1H), 5.24(d, 0.5H), 5.26(d, 0.5H) |

Example 117

(2,5-diaza-5-methyl-bicyclo[4.3.0]nonane)-1-carbonyl-Phe/benzyl ester

L-Phenylalanine benzyl ester isocyanate (290 mg) and triethylamine (305 μL) were dissolved in 10 mL of CH₂Cl₂ at 0° C., and 2,5-diaza-5-methyl-bicyclo[4.3.0]nonane (230 mg) was added. The solution was warmed to 25° C. and stirred for 16 hours. The mixture was diluted with ethyl acetate, extracted with 1N NaOH, brine, and dried (K₂CO₃). Purification (Amicon matrix silica SI (trademark), 30 μM) gave 210 mg of the title compound. ¹HNMR (CDCl₃, 300 MHz, partial) δ 1.38 (m, 1H), 1.65 (m, 1H), 2.22 (s, 1.5H), 2.23 (s, 1.5H), 2.98 (m, 1H), 3.50 (m, 1H), 4.77 (m, 1H), 4.83 (m, 1H), 5.15 (ABq, 2H).

Example 118 a) (2,5-diaza-5-methyl-bicyclo[4.3.0]nonane)-1-carbonyl-Phe

The substance of the preceding Example was hydrogenated (H₂, 45 psi, Pd(OH)₂, methanol, 0.95 eq of aqueous HCl). After 5 hours, the mixture was filtered through diatomaceous earth (Celite (trademark)) and concentrated to yield 170 mg of the crude acid which was used without further purification.

b) 4-(2,5-diaza-5-methyl-bicylo[4.3.0]nonane)-2R-benzylsuccinate

Using the above procedure, 4-(2,5-diaza-5-methyl-bicyclo [4.3.0] nonane)-2R-benzylsuccinic acid 1-monobenzyl ester was hydrogenated to give the title compound. ¹H NMR (CD₃OD, 300 MHz, partial) 6 2.00 (m, 2H), 2.80 (m, 4H), 2.98 (s, 3H), 3.72 (m, 2H), 7.27 (m, 5H).

c) 4-(2-(4-morpholino)ethyl-1-N-methylamino)-2R-benzylsuccinate

Using the above procedure, 1-benzyl 4-(2-(4-morpholino) ethyl-1-N-methylamino)-2R-benzylsuccinate was hydrogenated to give the title compound. ¹H NMR (CDCl₃, 300 MHz, partial) δ 2.47 (dd, 1H), 2.79 (m, 2H), 3.07 (s, 3H), 3.60 (m, 2H), 3.81 (m, 2H), 4.02 (m, 2H), 4.19 (m, 2H), 7.22 (m, 5H).

Using procedure of Example 118, the following compounds were prepared:

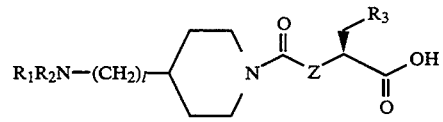

| Example | R₁R₂N | l | Z | R₃ | Salt Form | ¹H NMR (Partial) |
|---|---|---|---|---|---|---|
| 119 | Me₂N | 0 | CH₂ | Ph | HCl | (D₂O) 1.65(m, 2H), 1.98(m, 1H), 2.84(s, 6H), 3.50(m, 1H), 3.62(m, 1H), 4.05(d, 1H), 4.50(d, 1H) |
| 120 | [pyrrolidine-N—] | 0 | CH₂ | Ph | HCl | (CD₃OD) 1.65(m, 2H), 2.00(m, 2H), 3.12(m, 2H), 3.39 (m, 1H), 3.62(m, 2H), 4.03(m, 1H), 4.62(m, 1H) |
| 121 | [piperidine-N—] | 0 | CH₂ | Ph | HCl | (CD₃OD) 2.12(m, 2H), 2.40(ddd, 1H), 2.60(ddd, 1H), 2.85 (m, 2H), 3.46(m, 2H), 4.10(d, 1H), 4.61(d, 1H), 7.30(m, 5H) |
| 122 | (CH₃)₂N | 1 | CH₂ | Ph | HCl | (D₂O) 1.22(m, 2H), 1.60(m, 1H), 1.70(m, 2H), 3.41(m, 1H), 3.93(m, 1H), 4.45(m, 1H) |

-continued

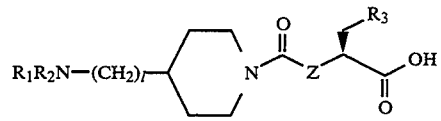

| Example | R₁R₂N | l | Z | R₃ | Salt Form | ¹H NMR (Partial) |
|---|---|---|---|---|---|---|
| 123 | piperidino | 1 | CH₂ | Ph | HCl | (CD₃OD) 2.32(dd, 1H), 2.54(dd, 1H), 3.92(m, 1H), 4.50 (m, 1H), 7.21(m, 5H) |
| 124 | piperidino | 0 | CH₂ | cyclohexyl | HCl | (CD₃OD) 2.50(dt, 1H), 2.70(dt, 1H), 2.78 (m, 1H), 3.53 (m, 3H), 4.10(d, 1H), 4.60(d, 1H) |

Example 125

4-(4-(N-t-BOC-(N-methyl)aminomethyl) piperidino)-2R-benzylsuccinate

1-Benzyl 4-(4-(BOC-(N-methyl) aminomethyl) piperidino)-2R-benzylsuccinate (310 mg) was hydrogenated (H₂, 45 psi, Pd(OH)₂, methanol), the mixture filtered through diatomaceous earth (Celite (trademark)) and concentrated to give the title compound (190 mg) which was used without further purification. ¹H NMR (CD₃OD, 300 MHz, partial) δ 1.12 (m, 2H), 1.66 (m, 2H), 2.39 (m, 1H), 2.60 (m, 1H), 2.72 (s, 3H), 3.83 (m, 1H), 4.40 (m, 1H).

Example 126 a) 4-(4-BOc-(N-methyl) aminomethyl) piperidino)-2R -benzylsuccinate-SMeCys-2(S)-amino-1-cyclohexyl- (3(R),4(S)) -dihydroxy-6-methylheptane According to procedure C, 4-(4-(BOC-(N-methyl)aminomethyl) piperidino)-2R-benzylsuccinate (180 mg) and SMeCys-2 (S)-amino-1-cyclohexyl-(3 (R), 4 (S))-dihydroxy-6-methylheptane (176 mg) were coupled to give the title compound (186 mg). ¹H NMR (CD3OD, 300 MHz, partial) δ 0.88 (d, 3H), 0.91 (d, 3H), 2.12 (s, 3H), 2.62 (m, 1H), 2.82 (s, 3H), 3.70 (m, 1H), 4.38 (m, 1H), 4.53 (m, 2H), 7.25 (m, 5H). FAB-MS 761 (MH+), 345.

Using General Procedure C, the following analogous substances were also prepared by coupling the appropriate intermediate of type

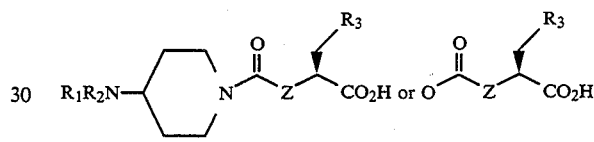

with the appropriate intermediate of type

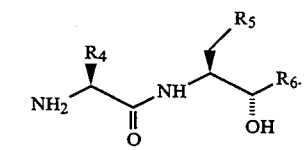

Either of these amines could also be used as the hydrochloride salt in which case an additional equivalent of triethylamine per additional equivalent of hydrochloride salt was employed.

| Example | R₁R₂N | Z | R₃ | R₄ | R₅ | R₆ | Salt Form | FAB-MS M⁺ + H (%) | ¹H NMR (Partial) |
|---|---|---|---|---|---|---|---|---|---|
| 127 | Me₂N | CH₂ | Ph | CH₂SCH₃ | Cy[a] | (OH, alkenyl chain) | HCl | 673 (27%) 301 (100%) | (CDCl₃) c 2.08(s, 1.5H), 2.09(s, 1.5H), 2.28(s, 3H), 2.29(s, 3H), 3.70(m, 1H), 4.58(m, 1H), 4.98(m, 2H), 5.80(m, 1H) |
| 128 | Me₂N | CH₂ | Ph | CH₂SCH₃ | Cy[a] | (OH, cyclopentylmethyl) | HCl | 687 (45%) 301 (100%) | (CDCl₃) c 2.08(s, 1.5H), 2.09(s, 1.5H), 2.27(s, 3H), 2.28(s, 3H), 3.70(m, 1H), 4.36(m, 1H), 4.45(m, 1H), 4.53(m, 1H), 6.80(d, 1H) |
| 129 | Me₂N | CH₂ | Ph | CH₂SCH₃ | 2-thienyl | (OH, isobutyl) | HCl | 661 (60%) 301 (100%) | (CD₃OD) 0.86(d, 3H), 0.91(d, 3H), 2.10(s, 1.5H), 2.31(s, 3H), 2.32(s, 3H), 3.22(dd, 1H), 3.94(m, 1H), 4.40(m, 1H), 4.53(m, 1H) |
| 130 | Me₂N | CH₂ | Ph | CH₂SCH₃ | Cy[a] | (OH, alkenyl) | HCl | 659 (40%) 301 (100%) | (CD₃OD) c 2.13(s, 1.5H), 2.14(s, 1.5H), 2.85(s, 3H), 2.87(s, 3H), 4.08(m, 1H), 4.24(m, 1H), 4.50(m, 1H), 4.60(m, 1H), 5.00(m, 2H), 5.72(m, 1H) |
| 131 | Me₂N | CH₂ | Ph | CH₂SCH₃ | Cy[a] | (tetrahydrofuran-methyl) | HCl | 659.5 (85%) 301.3 (100%) | (CDCl₃)c 1.20(d, 3H), 2.10(s, 3H), 2.29(s, 3H), 2.30(s, 3H), 3.50(m, 1H), 3.70(m, 1H), 3.83(m, 1H), 4.41(m, 1H), 4.60(m, 1H) |
| 132 | (piperidinyl) | CH₂ | Cy | CH₂SCH₃ | Cy[a] | (OH, isobutyl) | HCl | 707 (72%) 347 (100%) | (CDCl₃)c 0.92(d, 1.5H), 0.93(d, 1.5H), 0.94(d, 1.5H), 0.95(d, 1.5H), 2.12(s, 3H), 3.00(dd, 1H), 3.30(m, 1H), 3.92(m, 1H) |
| 133 | Me₂N | CH₂ | Ph | CH₂SCH₃ | Cy[a] | (OH, isobutyl) | HCl | 661 (40%) 301 (100%) | (CD₃OD)c 0.90(d, 3H), 0.98(d, 3H), 2.13(s, 1.5H), 2.15(s, 1.5H), 2.30 (s, 3H), 2.32(s, 3H), 3.40(m, 1H), 3.92(m, 1H), 4.38(m, 1H) |

-continued

Structure:
R₁R₂N-C(=O)-N(Z)-CH(R₃)-C(=O)-NH-CH(R₄)-C(=O)-NH-CH(R₅)-CH(OH)-R₆ (with 4-aminopiperidine on left side)

| Example | R₁R₂N | Z | R₃ | R₄ | R₅ | R₆ | Salt Form | FAB-MS[b] M⁺ + H (%) | ¹H NMR (Partial) |
|---------|-------|---|----|----|----|----|-----------|---------------------|------------------|
| 134 | pyrrolidinyl | CH₂ | Ph | CH₂SCH₃ | Cy[a] | CO₂i-Pr | HCl | 327 (100%) 687 (95%) | (CD₃OD)[c] 1.26(d, 6H), 2.11(s, 1.5H), 2.13(s, 1.5H), 4.36(m, 1H), 4.58(m, 1H), 4.90(m, 1H), 7.15–7.35(m, 5H) |
| 135 | piperidinyl | CH₂ | ZPh | (CH₂)₃CH₃ | Cy[a] | CO₂i-Pr | HCl | 697 (100%) 341 (87%) | (CDCl₃)[c] 1.25(d, 6H), 0.89(t, 1.5H), 0.91(t, 1.5H), 2.90(m, 1H), 3.55(m, 1H), 3.70(m, 1H), 4.42(m, 1H), 4.60(m, 1H), 5.00(m, 1H) |
| 136 | Me₂N | NH | Ph | i-Pr | Ph | OH | CH₃SO₃H | 638 (85%) 129 (100%)[c] | (CDCl₃)[c] 0.47(d, 3H), 0.75(d, 3H), 0.92(d, 6H), 2.21(s, 6H), 3.8(m, 2H), 4.6(q, 1H) |
| 137 | Me₂N | NH | Cy[a] | CH₂SMe | Cy[a] | OH | CH₃SO₃H | 668 (85) 129 (100)[c] | (CDCl₃)[c] 0.92(d, 3H), 0.93(d, 3H), 2.09(s, 3H), 2.28(s, 6H), 2.88(m, 3H), 3.17(m, 2H), 3.31(m, 1H), 4.39(q, 1H), 4.5(q, 1H) |
| 138 | Me₂N | NH | Cy[a] | CH₂SMe | Cy[a] | CONHMe | CH₃SO₃H | 639 (100)[c] | (CDCl₃)[c] 2.07(s, 3H), 2.29(s, 6H), 2.79(d, 3H), 3.09(dd, 1H), 4.13(m, 1H), 4.34(m, 1H), 4.44(q, 1H), 6.8(q, 1H) |
| 139 | Et₂N | NH | Cy[a] | CH₂SMe | Cy[a] | COOiPr | CH₃SO₃H | 696 (100)[c] | (CDCl₃)[c] 0.86(t, 6H), 1.24(d, 3H), 1.25(d, 3H), 2.10(s, 3H), 2.52(q, 4H), 2.53(dd, 1H), 4.2(m, 1H), 4.78(d, 1H), 5.04(m, 1H) |
| 140 | Me₂N | NH | Cy[a] | n-Pr | Cy[a] | COOiPr | CH₃SO₃H | 658 (100)[c] | (CDCl₃)[c] 0.88(t, 3H), 1.25(d, 6H), 2.28(s, 6H), 2.84(q, 2H), 3.95(m, 2H), 4.08(d, 1H), 4.42(d, 1H), 4.83(d, 1H), 5.03(m, 1H) |
| 141 | piperidinyl | NH | Cy[a] | n-Bu | Cy[a] | COOiPr | CH₃SO₃H | 704 (100)[c] | (CDCl₃)[c] 0.86(t, 3H), 1.25(d, 6H), 2.80(q, 2H), 3.97(m, 2H), 4.08(d, 1H), 4.43(q, 1H), 4.79(d, 1H), 5.03(m, 1H), 6.50(d, 1H) |
| 142 | piperidinyl | NH | Cy[a] | CH₂SMe | Cy[a] | COOiPr | CH₃SO₃H | 708 (100)[c] | (CDCl₃)[c] 1.25(d, 6H), 1.26(d, 3H), 2.11(s, 3H), 2.45(m, 4H), 3.05(dd, 1H), 4.20(m, 1H), 4.42(m, 2H), 4.75(d, 1H), 5.03(m, 1H) |
| 143 | Me₂N | NH | Ph | iPr | Ph | COOiPr | CH₃SO₃H | 638 (100)[c] | (CDCl₃)[c] 0.67(d, 3H), 0.92(d, 3H), 1.22(d, 3H), 1.25(d, 3H), 2.25(s, 6H), 2.88(dd, 1H), 2.99(dd, 1H), 3.23(dd, 1H), 4.03(m, 1H) |

-continued

| Example | R₁R₂N | Z | R₃ | R₄ | R₅ | R₆ | Salt Form | FAB-MS[b] M⁺ + H (%) | ¹H NMR (Partial) |
|---|---|---|---|---|---|---|---|---|---|
| 144 | pyrrolidinyl-N | NH | Ph | n-Bu | Cy[a] | COOiPr | CH₃SO₃H | 684 (95) 155 (100)[c] | (CDCl₃)[c] 0.86(t, 3H), 1.25(d, 3H), 1.26(d, 3H), 2.98(dd, 1H), 3.18(dd, 1H), 3.70(m, 2H), 4.08(d, 1H), 4.21(m, 1H), 5.06(m, 1H) |
| 145 | Me₂N | NH | Cy | n-Bu | Cy[a] | COOiPr | CH₃SO₃H | 664 (100)[c] | (CDCl₃)[c] 0.86(t, 3H), 1.25(d, 6H), 2.29(s, 6H), 2.82(m, 2H), 3.93(m, 2H), 4.08(d, 1H), 4.41(m, 1H), 4.83(m, 1H), 5.03(m, 1H) |
| 146 | Me₂N | CH₂ | Ph | CH₂SMe | Cy[a] | acetonide | None | 647 (90) 301 (100)[c] | (CDCl₃)[c] 2.13(s, 3H), 2.26 and 2.27(s, 6H total), 4.78(d, 1H), 7.15–7.3(m, 5-6H) |
| 147 | Me₂N | CH₂ | Ph | CH₂SMe | Cy[a] | thiazolyl | 2CH₃SO₃H | 658 (60) 301 (100)[c] | (CDCl₃)[c] 2.03 and 2.04(s, 3H total), 2.24 and 2.25(s, 6H total), 3.73(d, 1H), 4.35(m, 2H), 4.5(m, 1H), 4.94(t, 1H) |
| 148 | Me₂N | CH₂ | Ph | CH₂SMe | Cy[a] | imidazolyl-CH₂OCH₂Ph | 2HCl | 761 (100)[c] | (CDCl₃)[c] 2.08 and 2.09(s, 3H total), 2.23 and 2.25(s, 6H total), 4.7(dd, 1H), 5.35–5.55(m, 2H), 7.1–7.4(m, ca. 10H) |
| 149 | piperidinyl-N | NH | Cy[a] | CH₂SMe | Cy[a] | CONHMe | CH₃SO₃H | 665 (100)[c] | (CDCl₃)[c] 2.08(s, 3H), 2.79(d, 3H), 3.08(dd, 1H), 3.88(t, 3H), 4.07(d, 1H), 4.11(m, 1H), 4.27(m, 1H), 4.45(m, H) |
| 150 | piperidinyl-N | NH | Cy[a] | N-Bu | Cy[a] | COOiPr | CH₃SO₃H | 609 (100)[c] | (CDCl₃)[c] 0.85(t, 3H), 1.23(d, 6H), 2.55(m, 4H), 2.87(q, 2H), 3.82(t, 2H), 4.05(s, 1H), 4.4(m, 1H) |
| 151 | cyclohexyl-N | NH | Cy[a] | CH₂SMe | Cy[a] | CH(OH)CH₂CH(CH₃)₂ | CH₃SO₃H | 708 (100)[c] | (CDCl₃)[c] 0.91(d, 3H), 0.92(d, 3H), 2.09(s, 3H), 2.45(m, 4H), 4.38(m, 1H), 4.48(m, 1H), 4.82(d, 1H) |

-continued

R₁R₂N-[piperidine with C(=O)-N]-CH(R₃)-C(=O)-NH-CH(R₄)-C(=O)-NH-CH(R₅)-CH(R₆)-OH

| Example | R₁R₂N | Z | R₃ | R₄ | R₅ | R₆ | Salt Form | FAB-MS[b] M⁺ + H (%) | ¹H NMR (Partial) |
|---|---|---|---|---|---|---|---|---|---|
| 152 | pyrrolidin-1-yl | NH | Cy[a] | CH₂SMe | Cy[a] | OH (with isobutyl branch) | CH₃SO₃H | 694 (92) 155 (100)[c] | (CDCl₃)[c] 0.91 (d, 3H), 0.92(d, 3H), 2.09(s, 3H), 2.55(m, 4H), 2.78(dd, 1H), 3.09(dd, 1H), 4.37(m, 1H), 4.48(m, 1H), 4.82(d, 1H) |
| 153 | pyrrolidin-1-yl | NH | Cy[a] | CH₂SMe | Cy[a] | COOiPr | CH₃SO₃H | 694 (97) 155 (100)[c] | (CDCl₃)[c] 1.25(d, 3H), 1.26(d, 3H), 2.11(s, 3H), 2.77(dd, 1H), 2.94(t, 2H), 3.05(dd, 1H), 4.10(m, 1H), 4.20(m, 1H), 5.07(m, 1H) |

Legend:
[a]Cy = Cyclohexyl,
[b]obtained on salt,
[c]obtained on free base

| Example | R₁R₂N | Z | R₃ | R₄ | R₅ | R₆ | Salt Form | FAB-MS[b] M⁺ + H (%) | ¹H NMR (Partial) |
|---|---|---|---|---|---|---|---|---|---|
| 154 | (N-methyl octahydropyrrolo-piperidine) | NH | Ph | CH₂SMe | Cy[a] | CO₂iPr | HCl | 674 (60%) 141 (100%) | (CDCl₃)[c] 1.27 (d, 3H), 1.28(d, 3H), 2.05(s, 3H), 2.72 (dd, 1H), 2.36(s, 3H), 4.12(m, 1H), 4.62(m, 1H), 4.73 (m, 1H), 5.10(m, 1H) |
| 155 | (N-methyl octahydropyrrolo-piperidine) | CH₂ | Ph | CH₂SMe | Cy[a] | CO₂iPr | HCl | 673 (55%) 313 (100%) | (CDCl₃) 1.24(d, 3H), 1.26(d, 3H), 2.03(s, 1.5H), 2.04 (s, 1.5H), 2.31(s,1.5H), 2.34(s, 1.5H), 4.08 (m, 1H), 5.01(m, 1H), 7.20(m, 5H) |
| 156 | Me₂NCH₂—(azetidine)—N— | CH₂ | Ph | CH₂SMe | Cy[a] | CH(OH)CH₂CH(CH₃)₂ | HCl | 675 (25%) 315 (100%) | (CD₃OD)[c] 0.88(d, 3H), 0.92(d, 3H), 2.12(s, 1.5H), 2.14 (s, 1.5H), 2.33(dd, 1H), 2.89(s, 3H), 2.90(s, 3H), 3.92 (m, 1H), 4.31(m, 1H) |
| 157 | piperidino-CH₂—(azetidine)—N— | CH₂ | Ph | CH₂SMe | Cy[a] | CH(OH)CH₂CH(CH₃)₂ | HCl | 715 (55%) 355 (100%) | (CD₃OD)[c] 0.88(d, 3H), 0.92(d, 3H), 2.12(s, 1.5H), 2.13 (s, 1.5H), 3.42(m, 1H), 3.92(m, 1H), 4.28(m, 1H), 4.44 (m, 2H), 7.26(m, 5H) |
| 158 | morpholino-N-CH₂CH₂-N(CH₃)— | CH₂ | Ph | CH₂SMe | Cy[a] | CO₂iPr | HCl | 677 (100%) 317 (15%) | (CDCl₃)[c] 1.25(d, 6H), 1.80(m, 1H), 2.11(s, 1.5H), 2.12 (s, 1.5H), 3.43(m, 1H), 4.07(m, 1H), 4.32(m, 1H), 4.48 (m, 1H), 5.01(m, 1H) |

Legend:
[a]Cy = cyclohexyl; [b]obtained on salt; [c]obtained on free base

Example 159

4-(4-(N-methylaminomethyl)piperidino)-2R-benzylsuccinate-SMeCys-2S-amino-1-cyclohexyl-(3R, 4S) dihydroxy-6-methylheptane 4-(4-(BOC-(N-methyl) aminomethyl) piperidino-2R-benzylsuccinate-SMeCys-2S-amino-1-cyclohexyl-(3R, 4S)-dihydroxy-6-methylheptane (156 mg) was deprotected according to procedure D to give the title compound (167 mg). ¹H-NMR (CD₃OD, 300 MHz, partial) 0.87 (d, 3H), 0.91 (d, 3H), 2.12 (s, 1.5H), 2.13 (s, 1.5H), 2.82 (d, 3H), 3.42 (m, 1H), 4.35 (m, 1H). .FAB MS (m/e): 661.6 (MH⁺), 301.3.

The following Examples [160–197] were prepared by reductive amination of the appropriate tripeptide ketone with the appropriate amine according to general procedure A.

| Example | R₁R₂N | Z | R₃ | R₄ | R₅ | R₆ | Salt Form | FAB-MS M⁺ + H (%) | ¹H NMR (Partial) |
|---|---|---|---|---|---|---|---|---|---|
| 160 | [spiro-dioxolane piperidine] | NH | Ph | CH₂SMe | Cy[a] | COOiPr | | 786 (100)[b] | (CDCl₃)[c] 1.26(d, 3H), 1.27(d, 3H), 2.08(s, 3H), 2.93(dd, 1H), 3.07(dd, 1H) 3.29(dd, 1H), 3.93(s, 4H), 4.78(d, 1H), 5.06(m, 1H) |
| 161 | PhCH₂(Me)N | NH | Ph | CH₂SMe | Cy[a] | COOiPr | | 738 (100)[b] | (CDCl₃)[c] 1.26(d, 3H), 1.27(d, 3H), 2.06(s, 3H), 2.13(s, 3H), 2.91(dd, 1H), 3.09(dd, 1H), 3.30(dd, 1H), 4.75(d, 1H), 5.07(m, 1H) |
| 162 | MeNH | NH | Cy[a] | CH₂SMe | Cy[a] | COOiPr | HCl | 654 (90) 115 (100)[b] | (CDCl₃)[c] 1.25(d, 3H), 1.26(d, 3H), 2.11(s, 3H), 2.42(s, 3H), 2.56(m, 1H), 2.77(dd, 1H), 3.06(dd, 1H), 4.09(d, 1H), 5.04(m, 1H) |
| 163 | [morpholine] | NH | Cy[a] | CH₂SMe | Cy[a] | COOiPr | CH₃SO₃H | 710 (100)[c] | (CDCl₃)[c] 1.25 (d, 3H), 1.26(d, 3H), 2.14(s, 3H), 2.74(dd, 1H), 3.03(dd, 1H), 4.21(m, 1H), 4.40(m, 2H), 4.82(br, 1H), 5.03(m, 1H) |
| 164 | [piperidine] | NH | p-MeO—C₆H₄ | CH₂SMe | Cy[a] | COOiPr | HCl | 732 (100)[c] | (CDCl₃)[c] 1.25(d, 3H), 1.26(d, 3H), 2.08(s, 3H), 3.08(dd, 1H), 3.22(dd, 1H), 4.09(d, 1H), 5.06(d, 1H), 6.85(d, 2H), 7.13(d, 2H) |
| 165 | [pyrrolidine] | NH | p-MeO—C₆H₄ | CH₂SMe | Cy[a] | COOiPr | HCl | 718 (100)[c] | (CDCl₃)[c] 1.25 (d, 3H), 1.26(d, 3H), 2.08(s, 3H), 3.08(dd, 1H), 3.20(dd, 1H), 3.78(s, 3H), 4.09(d, 1H), 6.85(d, 2H), 7.13(d, 2H) |
| 166 | Me₂N | NH | Ph | CH₂SMe | Cy[a] | CONHMe | HCl | 633 (70) 129 (100)[c] | (CDCl₃)[c] 2.12(s, 3H), 2.49(s, 6H), 2.73(s, 3H), 7.25(m, 5H) |
| 167 | Me₂N | NH | p-MeO—C₆H₄ | CH₂C=CH₂ | Cy[a] | COOiPr | HCl | 127 (100)[c] 672 (73) | (CDCl₃)[c] 1.26(d, 3H), 1.27(d, 3H), 2.36(s, 6H), 3.78(s, 3H), 4.08(d, 1H), 5.6(m, 1H), 6.84(d, 2H), 7.14(d, 2H) |
| 168 | Me₂N | NH | p-I—C₆H₄ | n-Pr | Cy[a] | COOiPr | HCl | 770 (100)[c] | (CDCl₃)[c] 0.88(t, 3H), 1.26(d, 3H), 2.28(s, 3H), 2.92 (dd, 1H), 3.12(dd, 1H), 4.09(d, 1H), 4.2(m, 1H), 4.89(d, 1H), 5.03(m, 1H) |
| 169 | [piperidine] | NH | p-MeO—C₆H₄ | CH₂SMe | Cy[a] | OH (isobutyl-CH) | CH₃SO₃H | 732 (100)[c] | (CDCl₃)[c] 0.94(d, 6H), 2.09(s, 3H), 2.88(dd, 1H), 3.79 (s, 3H), 6.87(d, 2H), 7.15(d, 2H) |

-continued

| Example | R₁R₂N | Z | R₃ | R₄ | R₅ | R₆ | Salt Form | FAB-MS M⁺ + H (%) | ¹H NMR (Partial) |
|---|---|---|---|---|---|---|---|---|---|
| 170 | Me₂N | NH | p-MeO—C₆H₄ | CH₂SMe | Cyᵃ | 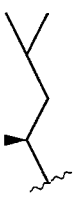 OH | HCl | 692 (100)ᵇ | (CDCl₃)ᶜ 0.93(d, 6H), 2.09(s, 3H), 2.09(s, 3H), 2.26(s, 6H), 3.79(s, 3H), 6.87(d, 2H), 7.13(d, 2H) |
| 171 | 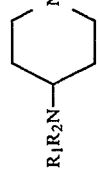 | NH | p-MeO—C₆H₄ | CH₂SMe | Cyᵃ |  OH | CH₃SO₃H | 718 (100)ᶜ | (CDCl₃)ᶜ 0.94(d, 6H) 2.09(s, 3H), 4.11(m, 1H), 4.38(m, 1H), 4.57(q, 1H), 4.74(s, 1H), 6.87(d, 2H), 7.13(d, 2H) |
| 172 | Me₂N | NH | p-I—C₆H₄ | CH₂SMe | Cyᵃ | COOiPr | HCl | 788 (65) 129 (100)ᶜ | (CDCl₃)ᶜ 1.25(d, 3H), 1.26(d, 3H), 2.09(s, 3H), 2.31(s, 6H), 2.91(dd, 1H), 3.03(dd, 1H), 3.18(dd, 1H), 3.82(m, 1H), 5.03(m, 1H) |
| 173 | MeNH | O | Ph | CH₂SMe | Cyᵃ | 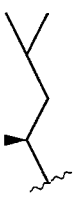 | CH₃SO₃H | 649 (100)ᶜ | (CDCl₃)ᶜ 0.85(m, 2H), 2.06(s,3H), 2.45(d, 3H), 3.73(q, 4H), 4.4(m, 2H), 7.1–7.3(m, 5H) |
| 174 | MeNH | O | Ph | CH₂SMe | Cyᵃ |  | CH₃SO₃H | | (CDCl₃)ᶜ 0.9(m, 2H), 2.00(s, 3H), 2.38(d, 3H), 3.23(d, 1H), 4.2(m, 1H), 4.32(d, 1H), 4.40(m, 1H), 7.1–7.3(m, 5H) |
| 175 | MeNH | O | Ph | CH₂SMe | Cyᵃ | 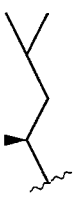 | CH₃SO₃H | 681 (60) 119 (100) | (CDCl₃)ᶜ 0.9(m, 2H), 2.04(s, 3H), 2.44(d, 3H), 3.78(s, 1H), 7.1–7.3(m, 5H) |
| 176 | MeNH | O | Cyᵃ | CH₂SMe | Cyᵃ | COOiPr | HCl | 655 (100)ᶜ | (CDCl₃)ᶜ 1.25 (d, 6H), 2.15(s, 3H), 2.43(s, 3H) |
| 177 |  | O | Cyᵃ | CH₂SMe | Cyᵃ | 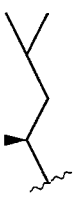 OH | CH₃SO₃H | 709(100)ᶜ | (CDCl₃)ᶜ 0.90(d, 3H), 0.93(d, 3H), 2.11(s, 3H) |

-continued

| Example | R₁R₂N | Z | R₃ | R₄ | R₅ | R₆ | Salt Form | FAB-MS M⁺ + H (%) | ¹H NMR (Partial) |
|---|---|---|---|---|---|---|---|---|---|
| 178 | morpholine (N with O) | O | Ph | CH₂SMe | Cy$^a$ | OH | CH₃SO₃H | 705 (100)$^b$ | D₂O$^b$ 0.88(d, 3H), 0.93(d, 3H), 2.14(s, 3H), 2.8(s), 5.2(br, 1H), 7.35(m, ca. 5H) |
| 179 | morpholine (N with O) | CH₂ | Ph | CH₂SMe | Cy$^a$ | OH | CH₃SO₃H | 703 (90) 343 (100)$^b$ | (CDCl₃) 2.12 and 2.13(s, 3H total), 2.5(m, 4H), 3.7(m, 4H), 4.03(d, 1H), 5.02(m, 1H) |
| 180 | Me(H)N | CH₂ | Ph | CH₂SMe | Cy$^a$ | CO₂iPr | HCl | 287 (100%)$^b$ 647 (50%) | (CDCl₃)$^c$ 1.22(d, 3 H), 1.23(d, 3H), 2.12(s, 3H), 2.42(d, 3H), 3.70(m, 1H), 4.00(t, 1H), 4.92(m, 1H), 6.92(m, 1H) |
| 181 | Et(Me)N | CH₂ | Ph | CH₂SMe | Cy$^a$ | CO₂iPr | HCl | 675 (100%)$^b$ 315 (92%) | (CD₃OD)$^c$ 1.24(d, 6H), 1.40(dt, 3H), 2.09(s, 1.5H), 2.11(s, 1.5H), 2.76(s, 1.5H), 2.78(s, 1.5H), 3.50(m, 1H), 4.62(m, 1H) |
| 182 | Et₂N | CH₂ | Ph | CH₂SMe | Cy$^a$ | CO₂iPr | HCl | 689 (100%)$^b$ 329 (92%) | (CD₃OD)$^c$ 1.24(t, 3H), 1.36(t, 3H), 2.10(s, 1.5H), 2.12(s, 1.5H), 2.53(dd, 1H), 3.72(m, 1H), 4.07(dd, 1H), 4.30(m, 1H), 5.10(m, 1H) |
| 183 | H₂N | CH₂ | Ph | CH₂SMe | Cy$^a$ | CO₂iPr | HCl | 633 (35%)$^b$ 273 (100%) | (CDCl₃)$^c$ 1.25(d, 3H), 1.26(d, 3H), 2.11(s, 1.5H), 2.13(s, 3H), 2.53(dd, 1H), 3.72(m, 1H), 4.07(dd, 1H), 4.30(m, H), 5.02 (m, 1H) |
| 184 | piperidine | CH₂ | Ph | CH₂SMe | Cy$^a$ | CO₂iPr | HCl | 701 (100%)$^b$ 341 (95%) | (CDCl₃)$^c$ 1.20(d, 3H), 1.21(d, 3H), 2.06(s, 1.5H), 2.07(s, 1.5H), 3.76(br d, 1H), 4.40(m, 1H), 4.17(d, 1H), 4.60(br d, 1H), 5.00 (m, 1H) |
| 185 | Me₂N | CH₂ | p-I—C₆H₄ | CH₂SMe | Cy$^a$ | CO₂iPr | HCl | 707 (100%)$^b$ 427 (98%) | (CDCl₃)$^c$ 1.26(d, 6H), 2.21(s, 1.5H), 2.22(s, 1.5H), 3.70 (m, 1H), 4.02(dd, 1H), 4.50(m, 1H), 5.02(m, 1H), 6.98 (d, 2H), 7.12(d, 2H) |
| 186 | Me₂N | CH₂ | 2-thienyl | CH₂SMe | Cy$^a$ | CO₂iPr | HCl | 667 (77%)$^b$ 307 (100%) | (CD₃OD)$^c$ 1.22(d, 3H), 1.23(d, 3H), 2.12(s, 1.5H), 2.13(s, 1.5H), 2.40(s, 3H), 2.41(s, 3H), 4.02(m, 1H), 4.65(m, 1H), 5.02(m, 1H), 7.23(d, 1H) |
| 187 | Me₂N | NH | Ph | CH₂-(2-thienyl) | Cy$^a$ | CO₂iPr | HCl | 698.7 (100%)$^b$ 302.4 (55%) | (CDCl₃)$^c$ 1.25(d, 3H), 1.28(d, 3H), 2.23(s, 6H), 3.18(dd, 1H), 3.37 (dd, 1H), 3.68(m, 1H), 3.73(m, 1H), 4.08(m,1H), 4.60(m, 1H), 5.05 (m, 1H) |

-continued

| Example | R₁R₂N | Z | R₃ | R₄ | R₅ | R₆ | Salt Form | FAB-MS M⁺ + H (%)[b] | ¹H NMR (Partial) |
|---------|-------|---|----|----|-----|-----|-----------|---------------------|------------------|
| 188 | Me—N⌒N— (piperazine) | NH | Ph | CH₂ (vinyl) | Cy[a] | CO₂iPr | HCl | 697 (100%) 329 (80%) | (CD₃OD)[c] 1.23(d, 6H), 2.32(s, 3H), 2.90(dd, 1H), 3.20(dd, 1H), 4.10 (d, 1H), 4.50(dd, 1H), 5.00(m, 1H), 5.10(m, 1H), 5.75(m, 1H) |
| 189 | iPr(H)N | CH₂ | Ph | CH₂SMe | Cy[a] | CO₂iPr | HCl | 675 (75%) 315 (100%) | (CD₃OD)[c] 1.26(d, 6H), 1.31(d, 3H), 3.32(d, 3H), 2.13(s, 1.5H), 2.15 (s, 1.5H), 2.38(m, 1H), 2.92(dd, 1H), 4.00(m, 1H), 4.12(dd, 1H) |
| 190 | ME(H)N | CH₂ | p-I—C₆H₄ | CH₂SMe | Cy[a] | CO₂iPr | HCl | 773 (50%) 647 (30%) 413 (100%) | (CD₃OD)[c] 1.24(d, 6H), 1.88(m, 1H), 2.09(s,1.5H), 2.10(s, 1.5H), 2.70(d, 3H), 4.10(dd, 1H), 4.98(m, 1H), 7.03(d, 2H), 7.60(d, 2H) |
| 191 | MeO—C(=O)CH₂—N(Me)— | NH | Ph | CH₂ (vinyl) | Cy[a] | OH | HCl | 700 (50%) 360 (100 %) | (CDCl₃)[c] 0.93(d, 6H), 2.38(s, 3H), 3.20(m, 1H), 3.70(s, 3H), 4.75 (d, 1H), 5.03(m, 2H), 5.60(m, 1H), 6.38(d, 1H), 7.25(m, 5H) |
| 192 | Me₂N | NH | Ph | CH₂ (vinyl) | Cy[a] | OH | HCl | 642 (100%) 302 (100%) | (CDCl₃)[c] 0.95(d, 6H), 2.28(s, 6H), 2.88(dd, 1H), 3.12(m, 1H), 3.70(m, 1H), 4.10(m, 1H), 4.80(m, 1H), 5.03(m, 2H), 5.55(m, 1H) |
| 193 | piperidinyl-N | NH | Ph | CH₂SCH₃ | Cy[a] | OH | HCl | 702 (100%) 314 (20%) 413 (100%) | (CDCl₃)[c] 0.97(d, 6H), 2.18(s, 3H), 2.92(dd, 1H), 3.20(m, 2H), 3.98(d, 1H), 4.13(m, 1H), 4.30(m, 1H), 4.50(m, 1H), 4.68(d, 1H) |
| 194 | piperidinyl-N | CH₂ | Ph | CH₂SCH₃ | Cy[a] | OH | HCl | 701 (60%) 154 (100%) | (CDCl₃)[c] 0.92(d, 1.5H), 0.93(d, 1.5H), 0.95(d, 3H), 2.13 (s, 1.5H), 2.14(s, 1.5H), 3.70(m, 1H), 4.18(m, 1H), 4.56(m, 1H) |
| 195 | Me₂N— | CH₂ | 2-thienyl | CH₂SCH₃ | Cy[a] | OH | HCl | 667 (75%) 307 (100%) | (CDCl₃)[c] 0.92(d, 3H), 0.94(d, 3H), 2.12(s, 3H), 2.32(s, 6H), 2.80(m, 1H), 2.95(dd, 1H), 3.78(m, 1H), 6.88(d, 1H), 7.21 (d, 1H) |
| 196 | Me(H)N— | CH₂ | 3-thienyl | CH₂SCH₃ | Cy[a] | OH | HCl | 653 (80%) 293 (100%) | (CD₃OD)[c] 0.92(d, 3H), 0.96(d, 3H), 2.13(s, 1.5H), 2.14 (s, 1.5H), 2.72(s, 3H), 2.45(m, 1H), 4.30(m, 1H), 7.01(d, 1H), 7.12(d, 1H), 7.38(dd, 1H) |

-continued
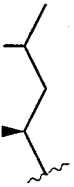
| Example | R₁R₂N | Z | R₃ | R₄ | R₅ | R₆ | Salt Form | FAB-MS M⁺ + H (%)[b] | ¹H NMR (Partial) |
|---|---|---|---|---|---|---|---|---|---|
| 197 | Me₂N— | O | Ph | CH₂SCH₃ | Cy[a] | OH | HCl | 663 (100%)[b] 244 (15%) | (CD₃OD)[c] 0.91(d, 3H), 0.93(d, 3H), 2.80(dd, 1H), 2.12(s, 3H), 3.42(dd, 1H), 4.28(m, 1H), 4.61(m, 1H), 5.12(dd, 1H), 7.28(m,5H) |
Legend:
[a]Cy = Cyclohexyl,
[b]obtained on salt,
[c]obtained on free base.

The following Examples were synthesized by coupling of the appropriate intermediate
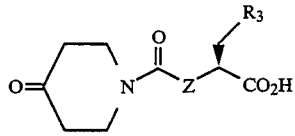
with the appropriate intermediate
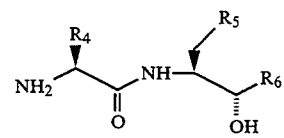
according to general procedure C. If the amine component was a hydrochloride, 1 equiv of triethylamine was employed.

| Example | Z | R₃ | R₄ | R₅ | R₆ | FAB-MS M⁺ + H (%)[b] | ¹H NMR (Partial) |
|---|---|---|---|---|---|---|---|
| 198 | NH | p-I—C₆H₄ | CH₂SMe | Cy[a] | COOiPr | 371 (100)[b]<br>759 (22) | (CDCl₃) 0.9(m, 2H), 1.26(d, 6H), 2.12(s, 3H), 3.62(m, 4H), 4.08 (d, 1H), 5.03(m, 1H), 6.97(d, 2H), 7.63(d, 2H) |
| 199 | NH | p-I—C₆H₄ | n-Pr | Cy[a] | COOiPr | 741 (27)[b]<br>371 (100) | (CDCl₃) 0.88(t, 3H), 1.26(d, 3H), 1.27(d, 3H), 2.40(m, 4H), 3.00 (d, 1H), 3.11(dd, 1H), 4.09(m, 1H), 6.96(d, 1H), 7.60(d, 1H) |
| 200 | O | Ph | CH₂SMe | Cy[a] | (1,3-dioxane) | 634 (30)[b]<br>119 (100) | (CDCl₃) 0.88(m, 2H), 2.12(s, 3H), 3.15(dd, 1H), 3.27 (dd, 1H), 4.42(d, 1H), 5.31(dd, 1H), 4.3–4.5(m, 3H), 5.27(dd, 1H) |
| 201 | O | Ph | CH₂SMe | Cy[a] | (dithiane-CMe) | 652 (42)[b]<br>119 (100) | (CDCl₃) 0.87(m, 2H), 2.10(s, 3H), 2.4(m, 4H), 3.07(m, 4H), 3.72(m, 4H) |
| 202 | O | Ph | CH₂SMe | Cy[a] | (1,3-dithiane) | 666 (25)<br>126 (100)[b] | (CDCl₃) 0.9(m, 2H), 2.0(m, 2H), 2.1(br s, 3H), 3.12(dd, 1H), 3.25 (dd, 1H), 3.7(m, ca.4H), 3.81(d, 1H), 4.4(m, 1H), 4.53(m, 1H) |
| 203 | O | Cy[a] | CH₂SMe | Cy[a] | COOiPr | 648 (32)<br>126 (100)[b] | (CDCl₃) 1.25(d, 3H), 1.26(d, 3H), 2.18(s, 3H), 2.67(dd, 1H), 2.97 (dd, 1H), 3.33(d, 1H), 5.02(m, 1H), 5.08(t, 1H) |
| 204 | O | Cy[a] | CH₂SMe | Cy[a] | OH (m) | 640 (25)<br>126 (100)[b] | (CDCl₃) 0.90(d, 3H), 0.92(d, 3H), 2.12(s, 3H), 2.85(dd, 1H), 4.35 (m, 1H), 4.50(q, 1H), 4.90(t, 1H), 6.73(m, 2H) |
| 205 | NH | p-CH₃O—C₆H₄ | CH₂SMe | Cy[a] | OH (m) | 663 (20)<br>119 (100) | (CDCl₃) 0.93(d, 3H), 0.94(d, 3H), 2.09(s, 3H), 2.42(m, 4H), 3.56 (m, 4H), 3.79(s, 3H), 4.03(d, 1H), 4.22(m, 1H), 4.52(m, 1H) |
| 206 | NH | Ph | CH₂SMe | Cy[a] | CONHMe | | (DMSO-d₆) 2.07(s, 3H), 2.57(br, 3H), 3.54(m, 3H), 3.81(br, 1H), 4.12(br, 1H), 4.42(m, 2H) |
| 207 | NH | p-CH₃O—C₆H₄ | CH₂C=CH₂ | Cy[a] | COOiPr | 643 (40)<br>275 (100) | (CDCl₃) 1.26(d, 3H), 1.27(d, 3H), 2.94(dd, 1H), 3.13(dd, 1H), 3.77 (s, 3H), 4.08(dd, 1H), 5.6(m, 1H), 6.84(d, 2H), 7.12(d, 2H) |

-continued

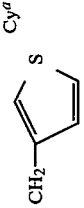

| Example | Z | R3 | R4 | R5 | R6 | FAB-MS M+ + H (%) | 1H NMR (Partial) |
|---|---|---|---|---|---|---|---|
| 208 | O | Ph | CH2SMe | Cy[a] | OH, m (isobutyl) | 634(50) | (CDCl3) 0.92(d, 3H) 0.94(d, 3H), 2.07(s, 3H), 2.61(dd, 1H), 3.72 (q, 1H), 4.32(m, 1H), 4.45(q, 1H), 5.10(dd, 1H), 7.3(m) |
| 209 | CH2 | Ph | CH2SMe | Cy[a] | OH, m (isobutyl) | 632 (45) 272 (100) | CDCl3 0.86(d, 3H), 0.91(d, 3H), 2.11(s, 3H), 3.61(t, 2H), 3.83(t, 2H), 4.33(m, 1H), 4.43(q, 1H), 6.7(d, 1H), 6.85(d, 1H) |
| 210 | CH2 | p-I—C6H4 | CH2SCH3 | Cy[a] | CO2iPr | 758 (40%) 397 (100%) | (CDCl3) 1.22(d, 6H), 1.85(d, 1H), 2.91(dd, 1H), 4.09(d, 1H), 4.33 (q, 1H), 4.50(m, 1H), 6.94(d, 2H), 7.62(d, 2H) |
| 211 | CH2 | 2-thienyl | CH2SCH3 | Cy[a] | CO2iPr | 638 (35%) 278 (100%) | (CDCl3) 0.90(m, 2H), 1.20(d, 6H), 1.82(m, 1H), 2.63(dd, 1H) 3.30(m, 1H), 4.30(m, 1H), 5.00(m, 1H), 6.80(d, 1H), 6.87(dd, 1H), 7.12(d, 1H) |
| 212 | NH | Ph | CH2 (3-thienylmethyl) | Cy[a] | CO2iPr | 669 (45%) 245 (100%) | (CDCl3) 1.22(d, 3H) 1.24(d, 3H), 1.81(d, 1H), 2.92(dd, 1H), 3.01 (dd, 1H), 3.18(dd, 1H), 3.27(dd, 1H), 4.07(dd, 1H), 4.53(m, 1H) |
| 213 | NH | Ph | CH2C≡CH | Cy | OH | 613 (45%) 245 (100%) | (CDCl3) 0.92(d, 3H), 0.94(d, 3H), 2.68(m, 1H), 2.91(dd, 1H), 3.17(m, 1H), 4.12(m, 1H), 4.28(m, 1H), 4.90(d, 1H), 5.12(m, 2H) |
| 214 | CH2 | 3-thienyl | CH2SCH3 | Cy | OH | 638 (27%) 278 (100%) | (CDCl3) 0.92(d, 3H), 0.93(d, 3H), 2.01(s, 3H), 3.43(t, 2H), 4.27(m, 1H), 4.50(m, 1H), 6.99(dd, 1H), 7.08(d, H), 7.31(dd, 1H) |
| 215 | CH2 | 2-thienyl | CH2SCH3 | Cy | OH | 638 (40%) 278 (100%) | (CDCl3) 2.12(s, 3H), 3.38(dd, 1H), 3.67(t, 2H), 4.32(m, 1H), 4.43(m, 1H), 6.76(dd, 1H), 6.82(dd, 1H), 6.93(dd, 1H) |

[a]Cy = cyclohexyl
[b]M+ by chemical ionization

According to the procedure described by Luly et al (J. Org. Chem. 53, 6109, (1988)) with the substitution of the appropriate Grignard reagent, the following compounds were prepared 2(1H)-pyrimidinone, and 24 mg of NaBH₄ was added. After stirring at 25° C. for 5 days, the mixture was diluted with ether, washed with water (3X), brine dried (MgSO₄) and concentrated. Purification by flash chro-

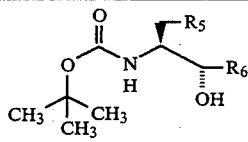

| Example | R₅ | R₆ | FAB-MS M⁺ + H (%) | ¹H NMR (Partial) |
|---|---|---|---|---|
| 216 | Cyclohexyl | | | (CDCl₃) 1.45(s, 9H), 2.22(m, 1H), 2.36(m, 1H), 3.37(m, 2H), 4.05(m, 1H), 4.30(d, 1H), 4.53(d, 1H), 5.01(m, 2H), 5.82(m, 1H) |
| 217 | Cyclohexyl | | 370 (15%) 270 (100%) | (CDCl₃) 1.44(s, 9H), 2.12(m, 1H), 3.21(m, 1H), 3.32(m, 1H), 4.05(m, 1H), 4.22(d, 1H), 4.57(d, 1H) |
| 218 | Cyclohexyl | | 356 (30%) 256 (100%) | (CDCl₃) 1.43(s, 9H), 2.01(d, 1H) 2.12(m, 2H), 3.33(m, 2H), 4.07(m, 1H), 4.32(d, 1H), 4.60(d, 1H), 5.00(m, 2H), 5.73(m, 1H) |
| 219 | 2-thienyl | | | (CDCl₃) 0.86(d, 3H), 0.91(d, 3H), 1.42(s, 9H), 1.89(m, 1H), 2.08(d, 1H), 3.09(d, 2H), 3.27(m, 1H), 3.34(m, 1H), 3.92(d, 1H), 4.17(m, 1H) |

Example 220

2S-(2 (S)-N-t-BOC-amino-3-cyclohexyl-1(R)-hydroxy)prop -1-yl-5(R)-methyltetrahydrofuran The compound of example 216 (870 mg) was dissolved in 14 mL of CH₂Cl₂ and 14 ml of saturated sodium bicarbonate. The solution was cooled to 0° C., and iodine (680 mg) was added in one portion. After stirring for 30 minutes, sodium bisulfite was added, and then 50 mL of ether. The organic layer was washed with saturated sodium bicarbonate, brine, dried (MgSO₄) and concentrated and purified by flash chromatography (Amicon matrix silica SI (trademark), 30 μM) to give 1.01 g of the primary iodide. This material (150 mg) was dissolved in 1.5 mL of 1,3-dimethyl-3,4,5,6-tetrahydromatography (Amicon matrix silica SI (trademark), 30 μM) provided 101 mg of the title compound. ¹H NMR (CDCl₃, 300 MHz, partial) δ 0.90 (m, 2H), 1.23 (d, 3H), 1.52 (s, 9H), 2.10 (m, 1H), 2.81 (d, 1H), 3.62 (m, 1H), 3.69 (m, 1H), 4.04 (m, 1H), 4.83 (d, 1H).

Example 221

2S-(2(S)-amino-3-cyclohexy-1(R)-hydroxy)prop-1-yl 5-(R)--methyltetrahydrofuran The product of the preceding Example (160 mg) was deprotected according to procedure D to yield 130 mg of the title compound.

According to Procedure D, the following analogues were prepared from the corresponding N-t-Boc derivatives.

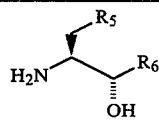

| Example | R₅ | R₆ | Salt Form | FAB-MS M⁺ + H (%) | ¹H NMR (Partial) |
|---|---|---|---|---|---|
| 222 | Cyclohexyl | | HCl | | (CD₃OD) 2.15(m, 2H), 2.32(m, 1H), 2.92(m, 1H) 3.17(dt, 1H), 3.22(dd, 1H), 3.55(m, 1H), 4.12(m, 1H), 5.00(m, 2H), 5.87(m, 1H) |
| 223 | Cyclohexyl | | HCl | 270 (100%) 126 (15%) | (D₂O) 3.47(m, 1H), 3.68(m, 1H), 3.97(m, 1H), 5.24(m, 1H) |
| 224 | Cyclohexyl | | HCl | 256 (100%) 126 (20%) | (CDCl₃) 0.93(m, 2H), 1.72(m, 6H), 2.11(m, 2H), 3.20 (t, 1H), 3.38(dd, 1H), 3.73(m, 1H), 5.00(m, 2H), 5.81(m, 1H) |

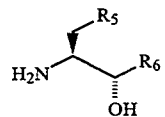

| Example | R₅ | R₆ | Salt Form | FAB-MS M⁺ + H (%) | ¹H NMR (Partial) |
|---|---|---|---|---|---|
| 225 | 2-thienyl | (structure: CH with isobutyl branch and OH) | HCl | | (D₂O) 0.86(d, 3H), 0.88(d, 3H), 1.20(m, 2H), 1.60(m, 1H), 3.13(dd, 1H), 3.23(m, 2H), 3,70(m, 1H), 7.00(d, 2H), 7.32(dd, 1H) |

Example 226

SMeCys-2(S)-amino-1-cyclohexyl-(3(R), 4(S))-dihydroxy-5-cyclopentylpentane a) BOC-SMeCys-2(S)-amino-1-cyclohexyl-(3(R), 4(S))-dihydroxy-5-cyclopentylpentane BOC-SMeCys (254 mg) and 2S-amino-1-cyclohexyl-(3R, 4S)-dihydroxy-5-cyclopentyl-pentane (300 mg) were coupled according to procedure C, and the product purified by crystallization from isopropyl ether/hexanes to give 254 mg of the title compound. ¹H NMR (CDCl₃, 300 MHz, partial) δ 1.44 (s, 9H), 2.03 (m, 1H), 2.15 (s, 3H), 2.25 (m, 1H), 2.82 (d, 2H), 3.25 (m, 2H), 4.09 (m, 1H), 4.23 (q, 1H), 4.39 (dt, 1H), 5.37 (d, 1H), 6.43 (d, 1H).

b) SMeCys-2(S)-amino-1-cyclohexyl-(3(R), 4(S))-dihydroxy-5-cyclopentylpentane

BOC-SMeCys-2S-amino-1-cyclohexyl-(3 (R), 4 (S)-dihydroxy-5-cyclopentyl-pentane (245 mg) was dissolved in 2 mL of CH₂Cl₂ and cooled to 0° C. Trifluoroacetic acid (2.5 mL) was added, and the reaction stirred at 0° C. for 1 h. The mixture was concentrated and the residue dissolved in ethyl acetate and extracted with 0.5N NaOH, brine, dried (Na₂SO₄) and concentrated to give 173 mg of the title compound.

Example 227

SMeCys-2(S)-amino-1-(2-thienyl)-3(R), 4(S)-dihydroxy-6-methylheptane 2S-amino-1-(2-thienyl)-(3(R), 4(S)-dihydroxy-6-methylheptane (163 mg) was coupled with BOC-SMeCys according to procedure C and deprotected according to the procedure of Example 226B to give the title compound (117 mg). ¹H NMR (CDCl₃, 300 MHz, partial) δ 0.86 (d, 3H), 0.93 (d, 3H), 1.99 (s, 3H), 2.42 (dd, 1H), 2.91 (dd, 1H), 3.40 (d, 1H), 3.57 (dd, 1H), 4.40 (m, 1H), 6.81 (d, 1H), 6.92 (dd, 1H), 7.18 (d, 1H), 7.70 (d, 1H).

Example 228

SMeCys-8 (S.)-amino-9-cyclohexyl-(6 (S), 7 (R))-dihydroxy-1-nonene

8(S)-amino-9-cyclohexyl-(6(S), 7(R))-dihydroxy-1-nonene (142 mg) was coupled with BOC-SMeCys according to Procedure C and the product deprotected according to the procedure of Example 226B to give the title compound (94 mg). ¹H NMR (CDCl₃, 300 MHz, partial) δ 1.00 (m, 2H), 2.73 (dd, 1H), 2.98 (dd, 1H), 3.18 (t, 1H), 3.26 (d, 1H), 3.62 (dd, 1H), 4.28 (dd, 1H), 4.60 (m, 1H), 5.01 (m, 2H), 5.82 (m, 1H), 7.50 (d, 1H). FAB MS 373 (MH+).

Example 229

4-(4-Piperidone)-2{R)-(2-thienylmethyl)succinate

2(R)-(2-thienylmethyl)-succinnic acid 1-monobenzyl ester was prepared by adapting the procedure described by Plattner et al. (J. Med. Chem. 31, 2277, (1988)) to 3-(2-thienyl) propionic acid, coupled with 4-piperidone monohydrate according to Procedure C, and the monoamide/mono-ester product hydrogenated according to the procedure of Example 125 to give the title compound. ¹H NMR (CDCl₃, 300 MHz, partial) 6 2.56 (dd, 1H), 2.79 (dd, 1H), 3.12 (dd, 1H), 3.91 (m, 1H), 6.82 (d, 1H), 6.90 (dd, 1H), 7.13 (d, 1H).

Example 230

4-(4-piperidone)-2(R)-(4-iodophenylmethyl)-succinate 2 (R)-(4-iodophenylmethyl)-succinnic acid 1-monobenzyl ester was prepared by adapting the procedure described by Plattner et al. (J. Med. Chem., 31, 2277, (1988)) to 3-(4-iodophenyl) propionic acid, coupled with 4-piperidone monohydrate according to Procedure C, and the product hydrogenated according to the procedure of Example 125 to give the title compound. ¹H-NMR (CDCl₃, 300 MHz, partial) δ 2.70 (m, 2H), 3.12 (22, 1H), 3.23 (m, 1H), 3.60 (m, 1H), 3.73 (m, 2H), 3.99 (m, 1H), 6.91 (d, 2H), 7.60 (d, 2H).

Example 231

4-(4-piperidone)-2R-(3-thienylmethyl)-succinate

2(R)-(3-thienylmethyl)-succinnic acid 1-monobenzyl ester was prepared by adapting the procedure described by Plattner et al. (J. Med. Chem., 31, 2277, (1988)) to 3-(3-thienyl) propionic acid, coupled with 4-piperidone monohydrate according to Procedure C, and then hydrogenated according to the procedure of Example 125 to give the title compound. ¹H NMR (CDCl₃, 300 MHz, partial) 67 2.73 (dd, 1H), 2.88 (dd, 1H), 3.16 (dd, 1H), 3.22 (m, 1H), 3.95 (m, 1H), 6.90 (dd, 1H), 6.99 (d, 1H), 7.27 (dd, 1H).

Example 232

4-(4-Trimethylamonio-1-piperidino)-2R-benzylsuccinate -SMeCVs-norCSta Isopropyl Ester Iodide 4-(4-Dimethylamino-1-piperidino)-2R-benzylsuccinate -SMeCys-norCSta Isopropyl Ester (420 mg) was converted to the title compound (320 mg) according to the procedure described in Example 38. ¹H NMR (CDCl₃, 300 MHz, partial) δ 1.23 (d, 6H), 2.10 (s, 1.5H), 2.12 (s, 1.5H), 3.07 (s, 4.5H), 3.09 (s, 4.5H), 3.60 (m, 1H), 4.67 (m, 1H), 5.00 (m, 1H). FAB MS 675 (MH+), 256.

Example 233

S-Methylcysteine t-Butyl ester hydrochloride

A mixture of 13.5 g S-methylcysteine, 120 mL dioxane, and 10 mL concentrated sulfuric acid was cooled to 0° C. and isobutylene (ca. 50 mL) was added. The vessel was sealed and the mixture shaken at 25° C. for 16 hours and poured into a mixture of ethyl acetate, ice, and 80 mL of 6N NaOH. The layers were separated and the aqueous layer extracted with ethyl acetate. The organic layers were washed with brine, dried, and concentrated giving 8.5 g of a yellow oil. Ether (110 mL) was added, followed by 9 mL of 4M HCl-dioxane. The resulting solid was filtered and washed with ether giving the title substance as a colorless solid. $^1$H NMR (D$_2$O, partial) δ 1.53 (s, 9H), 2.18 (s, 3H), 3.09 (dd, 1H), 3.16 (dd, 1H), 4.28 (dd, 1H).

was stirred at 25° C. for 1 hour. 2.27 g of 4-(1-piperidino)piperidine was added and the mixture was stirred 24 hours, diluted with ethyl acetate, the solution extracted with 1N NaOH and brine, dried and concentrated giving an oil which was chromatographed on silica eluting with an ethanoldichloromethane gradient containing triethylamine to give 3.69 g of the title substance as an oil. FAB-MS 450 (100%, M+ +H). $^1$H NMR (CDCl$_3$, partial) δ 3.10 (d, 2H), 3.90 (m, 2H), 4.83 (m, 2H), 5.10 (d, 1H), 5.17 (d, 1H), 7.2–7.4 (m, 10H).

Using the above procedure, the following Examples were also prepared from the appropriate amino acid ester or substituted lactic acid ester and the appropriate secondary amine. One or both of the amine components could also be in an acid addition salt form, in which case one equivalent of triethylamine per equivalent of acid addition salt was additionally employed.

| Example | X | Z | R$_3$ | R$_{10}$ | MS | $^1$H NMR (CDCl$_3$, partial), δ |
|---|---|---|---|---|---|---|
| 237 | O=⟨piperidinone⟩N– | NH | p-I—C$_6$H$_4$ | t-Bu | 473 (100) | 1.42(s, 9H), 2.45(m, 4H), 3.05(m, 2H), 3.65 (t, 4H), 4.68(m, 1H), 6.90(d, 2H), 7.58(d, 2H). |
| 238 | O=⟨piperidinone⟩N– | O | Cyclohexyl | CH$_3$ | 312 (100) | |
| 239 | O=⟨piperidinone⟩N– | NH | Cyclohexyl | CH$_2$Ph | 387 (100) | 2.47(t, 4H), 3.69(m, 4H), 4.61(m, 1H), 4.92 (d, 1H), 5.08(d, 1H), 5.22(d, 1H), 7.34(m, 5H). |

Example 234

4-(4-Dimethylaminopiperidino)-2(R)-benzylsuccinoyl-SMeCys t-Butyl ester 4-(4-Dimethylaminopiperidino)-2(R)-benzylsuccinic acid hydrochloride (5.97 g) and S-methylcysteine t-butyl ester hydrochloride were coupled and according to General Procedure C giving 2.97 g of the title substance as a clear oil. FAB-MS 492 (100%, M+ +H). $^1$H NMR 1.38 and 1.39 (s, 9H total), 2.05 (s, 3H), 2.19 and 2.20 (s, 6H total), 3.80 (m, 2H), 4.55 (m, 2–3H), 7.1–7.3 (m, 5H).

Example 235

4-(4-Dimethylaminopiperidino)-2(R)-benzylsuccinoyl-SMeCys Hydrochloride 2.67 Grams of 4-(4-dimethylaminopiperidino)-2(R)-benzylsuccinoyl-SMeCys t-butyl ester was converted to the title substance, (2.98 g) by General Procedure D. $^1$H NMR (D$_2$O, partial) δ 2.09 and 2.10 (s, 3H total), 2.84 (s, 6H total), 7.24–7.40 (m, 5H).

Example 236

4-(1-piperidino)piperidine-1-carbonyl-Phe Benzyl Ester

A solution of phenylalanine benzyl ester (10 mmol) in 15 ml dichloromethane was added dropwise to a 0° C. solution of 1.34 g imidazole and 1.75 g carbonyldiimidazole in dichloromethane (15 ml), and the mixture

Example 240

Hexahydrophenylalanine benzyl ester hydrochloride

A solution of Boc-hexahydrophenylalanine (10 g) and triethylamine in 85 ml dichloromethane (5.4 mL) was treated sequentially at <5° C. with benzyl chloroformate (5.5 mL) and dimethylaminopyridine (450 mg). After being stirred 30 minutes at 25° C. the mixture was diluted with 500 mL dichloromethane and the resulting solution extracted with aqueous NaHCO$_3$, 1N HCl, 1N NaOH, brine, dried, and concentrated giving 12.2 g of a colorless oil. This material was dissolved in 15 mL dichloromethane and treated at 25° C. with 95 mL 4.7M HCl-dioxane for 1 hour, concentrated, and the resulting solid washed with ether giving 9.25 g of the title substance as a colorless solid.

Example 241

4-Ketopiperidine-1-carbonyl-hexahydrophenylalanine

A solution of the benzyl ester of the title substance (4.45 g) in 40 mL methanol and 4 mL acetic acid was shaken with 450 mg 10% palladium on carbon under 50 p.s.i. hydrogen for 20 minutes. The catalyst was filtered, the filtrates concentrated, and the residue dissolved in ethyl acetate, This solution was washed with water (3×), dried, and concentrated giving the title substance (3.41 g) as a colorless foam. $^1$H NMR (CDCl$_3$, partial)

δ 2.50 (t, 4H), 3.71 (m, 4H), 4.45 (m, 1H), 5.19 (d, 1H), and 7.6 (br, 1H). FAB-MS 297 (100%, M+ +H).

Example 242

4-(1-Pyrrolidino) piperidine-1-carbonyl-hexahydro-L-phenylalanine

A solution of 4-(1-pyrrolidino) piperidine-1-carbonyl-L-Phe (1.5 g) in 20 mL aqueous 0.22M HCl was shaken with 1 g 10% rhodium on carbon under 50 p.s.i. hydrogen pressure for 3 hours. The catalyst was filtered, the filtrate concentrated, and the residue washed with ether and dried giving the title substance as a colorless solid (1.07 g), RP-HPLC 4.76 minutes (30/70, 100%). In analogous fashion the following compounds were also prepared.

Example 246

4-(1-Pyrrolidino)piperidine-1-carbonyl-phenylalanine Benzyl ester.

4-Ketopiperidine-1-carbonyl-L-phenylalanine benzyl ester (U.S. Pat. No. 4,314,342) was reductively aminated with pyrrolidine according to general procedure A (above) and purified by chromatography in an ethanol-dichloromethane gradient giving the title substance as a colorless solid (3.8 g). FAB-MS 410 (M+ +H, 100%), $^1$H NMR (CDCl$_3$, partial) δ 2.54 (m, 4H), 2.81 (dq, 2H), 3.09 (d, 2H), 3.82 (dm, 2H), 4.85 (m, 1H), 5.1 and 5.17, (d, 1H ea.), 6.98 (m, 2H), 7.15–7.4 (m, ca 10H).

In analogous fashion to Example 246, the following compounds were also prepared.

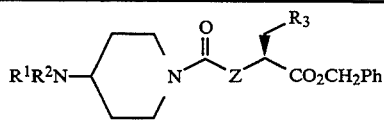

| Example | R$_1$R$_2$N | Z | R$_3$ | FAB-MS M$^+$ + H (%) | $^1$H NMR (CDCl$_3$, partial) δ |
|---|---|---|---|---|---|
| 247 | Me$_2$N | NH | Ph | 410 (100) | 2.25(s, 6H), 2.73(m, 2H), 3.09(d, 2H), 3.90(m, 2H), 4.83(t, 1H), 4.86(t, 1H), 5.09(d, 1H), 5.16(d, 1H), 7.15–7.4(m, 10H). |
| 248 | Et$_2$N | NH | Ph | 438 (100) | 1.01(t, 6H), 2.51(q, 9H), 3.09(m, 2H), 3.90(m, 2H), 4.85(m,2H), 5.099d, 1H), 5.17(d, 1H). |
| 249 | ⟨pyrrolidinyl⟩ | NH | Ph | 436 (100) | 2.82(dq, 2H), 2.99(d, 2H), 3.78 and 3.88(dt, 1H ea), 4.84(m, 2H) 5.09(d, 1H), 5.16(d, 1H), 6.99(m, 2H), 7.15–7.4(m, 10H). |
| 250 | Me$_2$N | NH | p-CH$_3$O—C$_6$H$_4$ | 440 (100) | 2.34(s, 6H), 3.03(d, 2H), 3.75(s, 3H), 3.93(m, 2H), 4.75(m, 1H), 4.87(d, 1H), 5.07 and 5.17(d, 1H ea), 6.73 and 6.88(d, 2H ea). |

[Structure: R$_1$R$_2$N-piperidine-N-C(=O)-NH-CH(cyclohexyl)-COOH]

| Example | R$_1$R$_2$N | FAB-MS | $^1$H nmr (D$_2$O, partial) |
|---|---|---|---|
| 243 | ⟨piperidinyl⟩ | 366 (100) | 0.95(m, 2H), 2.95(m, 2H), 4.1(m, 2H), 4.28 (m, 1H). |
| 244 | (CH$_3$)$_2$N | 326(100), 426 (t, 1H). | 2.84(s, 3H), 3.47(m, 1H), 4.13(d, 2H), |
| 245 | Et$_2$N | | 1.41(t, 6H), 2.18(d, 2H), 3.02(t, 3H), 3.2–3.5 (m, 4H), 3.7(m, 1H) 4.22(m, 2H), 4.4(t, 1H). |

Example 251

4-(1-Pyrrolidino)piperidine-1-carbonyl-L-phenylalanine 4-(1-Pyrrolidino)piperidine-1-carbonyl-L-phenylalanine benzyl ester (3.7 g) was dissolved in 15 mL water containing 1.1 equivalent 1N HCl and the resulting solution shaken with 375 mg 10% palladium on carbon for 1 hour. Filtration and concentration gave a residue which was washed with ether and dried giving the title substance as a colorless solid (2.79 g). FAB-MS 343 (M+ +H, 40%), 155 (60%), 11.9 (100%). $^1$H NMR (D$_2$O, partial) δ (DSS) 1.4 (m, 2H), 3.02 (dd, 1H), 3.25 (dd, 1H), 3.6 (m, 2H), 3.95 (t, 2H), 4.50 (dd, 1H), 7.25–7.4 (m, 5H). In analogous fashion, the following hydrochlorides were also prepared from the corresponding benzyl esters.

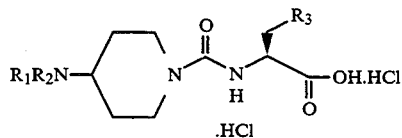

| Example | R₁R₂N | R₃ | FAB-MS Base, M+ + H (%) | ¹H NMR (CDCl₃, partial) δ |
|---|---|---|---|---|
| 252 | (piperidinyl) | Ph | 368 (10)<br>155 (100) | 2.99(dd, 1H), 3.25(dd, 1H) , 3.46(dd, 1H)<br>3.95(t, 2H), 4.54(dd, 1H), 7.25–7.4(m, 5H) |
| 253 | (CH₃)₂N | Ph | 320 (30)<br>119 (100) | 2.81(s, 6H), 3.02(dd, 1H), 3.27(dd, 1H)<br>4.0(t, 2H), 7.25–7.45(m, 5H). |
| 254 | Et₂N | Ph |  | 1.33(t, 6H), 1.95(d, 2H), 3.97(t, 2H),<br>4.56(dd, 1H), 7.3–7.5(m, 5H). |
| 255 | (pyrrolidinyl) | Ph | 346 (40)<br>119 (100) | 3.02(dd, 1H), 3.23(dd, 1H), 3.58(m, 2H)<br>3.95(m, 2H), 4.50(dd, 1H),<br>7.2–7.4(m, 5H). |

Example 256

1(S) and 1(R) 2(S)-Amino-3-cyclohexyl-1-(2-thiazolyl)-1-propanol

Using the procedure of Ryono and Weller (EP 337 295/EP 341481),2(S)-(Butoxycarbonylamin)o-3-cyclohexyl-1-propanal was condensed with 2-lithiothiazole and the product purified by chromatography on silica gel in ethyl acetate-hexane without separation of the isomers, giving the Boc analogs of the title substances in 66% yield. This mixture was deprotected with HCl-dioxane according to Procedure D and the product further converted to the free base (97%) by partitioning between 1N NaOH/ethyl acetate, and separation, drying, and concentration of the organic layer. 5.85 Grams of this mixture was chromatographed on 200 g silica gel packed in 1:1:200 concentrated NH₄OH/EtOH/CH₂Cl₂ and eluted with 1 L each of 1:1:200, 1:2:200, 1:4:200, 1:8:200 and 1:16:200 concentrated NH₄OH/EtOH/CH₂Cl₂.

The faster moving (less polar) isomer (3.2 g), and the slower moving/more polar isomer (0.57 g) and a mixture (1.75 g) were obtained. Less Polar isomer: ¹H NMR (CDCl₃, partial) δ 3.41 (m, 1H), 4.64 (d, 1H, J=3.4 Hz), 7.25 (d, 1H, J=3.2 Hz), 7.71 (d, 1H, J=3.2 Hz). More polar isomer: ¹H NMR (CDCl₃, partial) δ 3.28 (m, 1H), 4.87 (d, 1H, J=3.2 Hz), 7.25 (d, 1H, J=3.2 Hz), 7.71 (d, 1H, J=3.2 Hz). These substances were separately converted to their corresponding N-t-Boc derivatives the TLC behavior of which was compared: The less polar title substance gave the less polar Boc derivative and was thus assumed to have 2 (S), 1(R) stereochemistry since this the less polar Boc derivative is purported to have this stereochemistry (EP 337295).

By this procedure, the following compounds were also prepared.

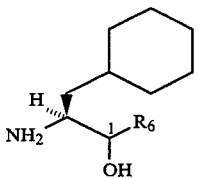

| Example | R₆ | Isomer at Position 1ᵃ | FAB-MS M+ + H (%) | ¹H NMR (CDCl₃, partial) |
|---|---|---|---|---|
| 257 | (2-methylthiazol-4-yl) | less polar | 255 (100) | 2.41(d, 3H), 3.31(dt, 1H), 4.55(d, 1H), 7.32(d, 1H). |
| 258 | | more polar | 255 (100) | 2.41(d, 3H), 3.22(m, 1H), 4.74(d, 1H), 7.32(d, 1H). |
| 259 | (2,5-dimethylthiazol-4-yl) | less polar | 269 (100) | 2.24(s, 3H), 2.29(s, 3H), 3.25(m, 1H), 4.52(d, 1H). |
| 260 | | more polar | 269 (100) | 2.23(s, 3H), 2.28(s, 3H), 3.23(m, 1H), 4.75(d, 1H). |

-continued

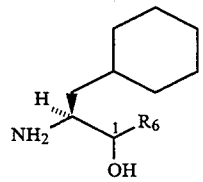

| Example | R₆ | Isomer at Position 1[a] | FAB-MS M⁺ + H (%) | ¹H NMR (CDCl₃, partial) |
|---|---|---|---|---|
| 261 | (benzothiazol-2-yl) | less polar | 291 (100) | 3.49(m, 1H), 4.74(d, 1H), 7.35(dt, 1H), 7.43(dt, 1H), 7.85(d, 1H), 7.94(d, 1H). |
| 262 | (4-methyl-5-vinylthiazol-2-yl) | less polar | 281 (100) | 2.36(s, 3H), 3.32(m, 1H), 4.52(d, 1H), 5.17(d, 1H), 5.39(d, 1H), 6.71(dd, 1H). |
| 263 | (4-methylthiazol-2-yl) | less polar | 255 (100) | 2.38(d, 3H), 3.32(dt, 1H), 4.58(d, 1H), 6.78(d, 1H). |
| 264 | | more polar | 255 (100) | 2.37(d, 3H), 3.23(m, 1H), 4.79(d, 1H), 6.77(d, 1H). |

[a] by TLC in 18/2/1 CHCl₃/EtOH/conc. NH₄OH. Less polar = faster moving isomer.

Example 265

2(S)-[4-(4-Dimethylaminopiperidino)-2(R)-benzylsuccinoyl-S-methylcysteinylamino]-3-cyclohexyl-1(R)-(2-imidazoyl)-1-propanol The compound of example 148 (119 mg) was shaken under 50 p.s.i. hydrogen pressure with 200 mg 20% Pd(OH)₂ on carbon catalyst in 10 ml water containing 0.34 mL 1N HCl for 24 hours. Filtration, concentration, and trituration with ether gave the title substance as the dihydrochloride (65 mg): FAB-MS 641 (M⁺+H, 20%), 309 (20), 155 (65), 119 (100).

Example 266

2 (S)-[4-(4-Dimethylaminopiperidino)-2(R)-benzylsuccinoyl-S-methylcysteinylamino]-3-cyclohexyl-1(S)-(2-imidazoyl)-1-propanol By the procedure of the preceding example the compound of Example 104 was converted to the title substance. FAB-MS 641 (M⁺+H, 100%). ¹H NMR (CDCl₃, partial) δ 2.04 and 2.06 (s, 3H total), 2.21 and 2.23 (s, 6H total), 3.62 (m, 2H), 4.35 (m, ca. 3H), 4.44 (m, 1H), 4.7 (d, 1H).

Example 267

4(S)-cyclohexylmethyl-5(R)-isopropoxycarbonyl oxazolidone

Nor-CSta isopropyl ester (30 g) was added in one portion to a stirred 25° C. solution of 30 g carbonyldiimidazole in 250 mL dichloromethane. After 1 hour the solution was washed twice with 300 mL portions of 2N HCl and twice with 300 mL portions of 2N NaOH, brine, dried, concentrated, and the residue chromatographed on silica (500 g) eluted with 1:3 ethyl acetate hexanes giving 23.6 g of the title substance. ¹H NMR (CDCl₃, partial) δ 1.26 and 1.27 (d, 3N ea), 3.90 (m, 1H), 4.49 (d, 1H), 5.11 (m, 1H), 5.61 (br, 1H).

Example 268

4(S)-cyclohexylmethyl-5(R)-formyl-2-oxazolidone

A solution of 28.1 g 4 (S)-cyclohexylmethyl-5(R)-isopropoxycarbonyl-2-oxazolidone in 500 mL anhydrous toluene was treated at −78° C. over 20 minutes with 250 mL of a 2.4M solution of disobutylaluminum hydride in hexane. After 15 minutes, 50 mL methanol was added dropwise at −78° C., followed by 500 ml of 50% aqueous Rochelle salts and 500 ml ether. The ether layer was separated at 25° C. and the aqueous layer extracted twice with 500 ml ether. The organic layers were combined, washed with brine, dried, and concentrated giving (13.9 g, TLC RF 0.23 in ethyl acetate/silica) a yellow foam which was used without further purification. The compound, which streaked on the TLC plate, was characterized as being the title substance by clean conversion to various expected products as described below, and to a single, well-behaved slightly less polar compound believed to be the corresponding alcohol on treatment with NaBH₄. The title substance gave the following spectrum: ¹³C NMR (CDCl₃, partial major peaks) δ 25.91, 25.97, 26.02, 26.06, 26.37, 32.72, 33.50, 33.55, 33.90, 33.96, 43.55, 43.91, 50.18, 51.55, 55.22, 55.49, 82.62, 83.36, 96.19, 97.04, 159.46, 159.67.

Example 269

4(S)-Cyclohexylmethyl-5(R)-(2-(1,3-dioxolanyl))-2-oxazolidone

The compound of the preceding Example (0.38 g) was heated at reflux in benzene (10 mL) with 23 mg p-toluenesulfonic acid and 0.2 ml ethylene glycol in an apparatus where the condensate was allowed to drip through 3 angstrom molecular selves before returning to the reaction vessel. After 18 hours, the mixture was cooled, diluted with ethyl acetate, and the resulting solution washed with 1N NaOH, dried, and the residue chromatographed on silica eluting with 1:1 ethyl acetate-hexanes giving the title substance as a colorless solid (290 mg). $^1$H NMR (CDCl$_3$, partial) δ 3.81 (dt, 1H), 3.9–4.15 (m, 4H), 5.00 (d, 1H), 5.82 (br, 1H). In like fashion the following substances were also prepared, substituting the appropriate dithiol or 1,3-dihydroxy propane for ethylene glycol.

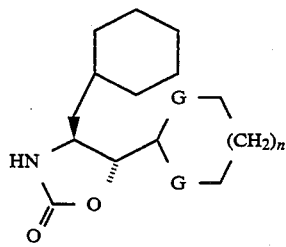

| Example | G | N | FAB-MS M$^+$ + H (%) | $^1$H NMR(CDCl$_3$, partial) δ |
|---|---|---|---|---|
| 270 | O | 1 | 270 (100) | 3.95(dt, 1H), 4.70(d, 1H) |
| 271 | S | 1 | 119 (100) 302 (15) | 3.90(m, 1H), 4.01(d, 1H), 4.40(t, 1H), 5.44(s, 1H) |
| 272 | S | 0 | 170 (100) 288 (25) | 3.24(d, 4H), 4.15(dd, 1H) 4.61(d, 1H), 5.68(br, 1H) |

Example 273

2(S)-Amino-3-cyclohexyl-1-(R)-(2-(1,3-dioxolanyl))-1-propanol

4(S)-Cyclohexylmethyl-5(R)-(2-(1,3-dioxolanyl) )-2-oxazolidone (168 mg) and barium hydroxide octahydrate (417 mg) were heated at reflux in 5 ml dioxane and 3 ml water for 2 hours. The mixture was filtered and the solids washed with dioxane. The filtrate was concentrated and the residue dissolved in 20 ml ethyl acetate. The resulting solution was washed with water, dried, and concentrated giving a solid which was triturated with hexane give 170 mg of the title substance. $^1$H NMR (CDCl$_3$, partial) δ 3.11 (m, 1H), 3.37 (t, 1H), 3.89 (m, 2H), 4.01 (m, 2H), 4.87 (d, 1H).

Example 274

2(S)-Amino-3-cyclohexyl-1(R)-(2-(1,3-dioxanyl))-1-propanol

By the procedure of the preceding Example, 840 mg of 4(S)-cyclohexylmethyl-5 (R)-2-(1,3-dioxanyl) )-2-oxazolidone gave 620 mg of the title substance. FAB-MS 244 (M$^+$+H, 100%). $^1$H NMR (CDCl$_3$, partial) δ 3.15 (m, 1H), 3.28 (dd, 1H), 3.7–3.8 (m, 2H), 4.10 (m, 2H), 4.57 (d, 1H).

Example 275

2(S)-Amino-3-cyclohexyl-1(R)-(2-(1,3-dithianyl))-1-propanol

A solution of 4 (S)-Cyclohexylmethyl-5 (R)-(2-(1,3-dithianyl) )-2-oxazolidone (480 mg) in 25 ml acetonitrile was treated at 25° C. with di-t-butyldicarbonate (450 mg) and 4-dimethylaminopyridine (19 mg). After 21 hours the mixture was diluted with 150 ml ethyl acetate and the resulting solution washed with 50 ml 1N NaOH, brine, dried and concentrated. The residue was chromatographed on silica eluting with ethyl acetate-hexane, giving N-t-Boc oxazolidone (FAB-MS 346 (M$^+$+H, 100%)). This substance was dissolved in 6 ml THF and treated with 1.8 ml of 2N NaOH and 3 ml water. After 24 hours the mixture was diluted with ethyl acetate and the resulting solution washed with brine, dried and concentrated. The residue was chromatographed on silica eluting with ethyl acetate-hexanes giving 2(S)-Boc amino-3-cyclohexyl-1(R)-(2-1,3-dithianyl))-1-propanol (300 mg, FAB-MS 376 (M$^+$+H, 25%). This substance was dissolved in 3 ml trifluoroacetic acid at 0° C. and the solution stirred at 25° C. for 30 minutes, evaporated, and the residue dissolved in dichloromethane. The resulting solution was washed with 1N NaOH, brine, dried, and concentrated giving 184 mg of the title substance as an off white solid. FAB-MS 276 (M$^+$+H, 100%). $^1$H NMR (CDCl$_3$, partial) δ 3.28 (m, 1H), 3.58 (dd, 1H), 4.11 (d, 1H).

Example 276

2(S)-Amino-3-cyclohexyl-1(R)-(2-1,3-dithiolanyl))-1-propanol

By the same sequence of the preceding Example, 4(S)-cyclohexylmethyl-5 (R)-(2-(1,3-dithiolanyl))-2-oxazolidone was converted via the N-t-Boc oxazolidone (FAB-MS 388 (M$^+$+H, 10%) and 332 (M$^+$+H-C$_4$H$_8$, 100%) ) and the N-t-Boc derivative of the title substance (FAB-MS 362 (M$^+$+H, 35%) to the title substance. $^1$H NMR (CDCl$_3$, partial) δ 4.63 (d, 1H, J=6.9 Hz). FAB-MS 262 (M$^+$+H, 100%).

Example 277

N-t-Butoxycarbonyl-4(S)-cyclohexylmethyl-2,2-dimethyl -5(R)-isopropoxycarbonyloxazolidine A solution of Boc-norCSta isopropyl ester (15.4 g) and 400 mg p-toluenesulfonic acid in 180 ml 2,2-dimethoxypropane was stirred at 40° C. for 72 hours and diluted with 900 ml of ether. The resulting solution was washed with saturated aqueous NaHCO$_3$, dried and concentrated. The residue was chromatographed on 900 g silica eluted with 5% ethyl acetate in hexane giving 13.5 g of the title substance. FAB-MS 384 (M$^+$+H, 10%), 284 ((M$^+$+H-C$_4$H$_8$CO$_2$, 100%). $^1$H NMR (CDCl$_3$, partial) δ 1.25 (d, 6H), 1.44 (S, 9H), 4.26 (m, 2H), 5.04 (m, 1H).

Example 278

N-t-Butoxycarbonyl-4(S)-cyclohexylmethyl-2,2-dimethyl -5(R)-pentafluoroethylcarbonyloxazolidine To 26 g of iodoperfluoropropane was introduced a −15° C. solution of the substance of the preceding example (2 g) in 25 ml ether. The resulting solution was cooled to −78° C. and treated over 15 min with 20 ml of 1.3 m methyllithiumlithium bromide complex. After 1 hour 6 ml of saturated aqueous NH$_4$Cl was added and the mixture extracted with ether. The organic layers were combined and washed successively with saturated aqueous NaHCO$_3$, 1N HCl, saturated aq. NaHCl$_3$, brine, dried, and concentrated and the residue chromatographed on silica in ethyl acetate-hexane (a gradient beginning with 1% ethyl acetate) giving 785 mg of the title substance. $^1$H NMR (DMSO-D$_6$, partial) δ 1.41 (s, 9H), 1.56 (s, 6H). $^{13}$C NMR (DMSO-D$_6$, partial) δ 93.57 (t, hydrated ketone carbonyl) 119.09 (qt,CF$_2$), 113.06 (tq, CF$_3$), 150 (S, CONH).

Example 279

N-t-Butoxycarbonyl-4(S)-cyclohexylmethyl-2,2-dimethyl-5(R)-1-(1,1,1,2,2-pentafluoro-1-hydroxypropyl)oxazolidine A solution of the compound of the preceding example (764 mg) in ethanol (9 ml) was treated at 25° C. with 65 mg sodium borohydride. After 2 hours the mixture was diluted with 50 ml ethyl acetate and the resulting solution stirred with 10 ml in HCl. The layers were separated and the organic layer washed with saturated aqueous $NaHCO_3$, brine, dried, and concentrated. The residue was chromatographed on silica eluted with an ethyl acetate-hexane gradient beginning with 1% ethyl acetate giving 521 mg of the major, faster moving component, a colorless solid. $^1H$ NMR ($CDCl_3$, partial) δ 1.46 (s, 9H), 1.52 (s, 3H), 1.62 (s, 3H), 3.07 (d, 1H), 4.14 (t, 1H). $^{13}C$ NMR ($CDCl_3$) δ 151.2 (s), ea. 120.8 (qt, $CF_3$), ca. 113.1 (tq, $CF_2$), 95 (s), 80.4 (s), 76.4 (s), 68.61 (t), 57.5 (d), 34.58 (s), 32.14 (s), 28.36 (s), 26.30 (s), 26.21 (s), 25.89 (s). FAB-MS 446 ($M^+ + H$, 15%), 390 ($M^+ + H - C_4H_8$, 100%) 346 ($M^+ + H - C_4H_8CO_2$, 75%).

Example 80

5(S)-Amino-6-cyclohexyl-4(R)-hydroxy-1,1,1,2,2-pentafluoro-3-hexanol

The product of the preceding Example (139 mg) was dissolved in 9 ml of 1:1:1 1N HCl-THF-acetic acid and the resulting solution was heated at 50° C. for 54 hours and stirred at 25° C. for 72 hours ether and water was added and the layers separated. The basic component was isolated by acid/base extraction using ethyl acetate giving 94 mg of residue which was chromatographed on silica eluted with a dichloromethane-ethanol gradient beginning with 1% of the latter. 70 mg of the title substance was thus obtained, TLC rf 0.13 in 18/2/1 $CHCl_3$/EtOH/HOAc.

Example 281

S-MeCys-nor-CSta N-methylamide Hydrochloride 685 mg Boc-S-methylcysteine and 729 mg nor-cSta N-methylamide were coupled according to General Procedure C and the product purified by chromatography on silica gel eluting with 1:4 ethyl acetate-hexanes, giving 850 mg of the protected dipeptide. This material was deprotected according to general procedure-D and the residue washed with ether giving 499 mg of the title substance. FAB-MS 332 (100%, $M^+ + H$), $^1H$ NMR (DMSO-$d_6$, partial) δ 2.12 (S, 3H), 2.57 (d, 3H), 2.62 (dd, 1H), 2.95 (dd, 1H), 3.85 (d, 1H), 3.96 (m, 1H), 4.09 (m, 1H). By the same general sequence, using the appropriate Boc-amino acid and amine, the following compounds were prepared. As individually noted, trifluoroacetic acid could be substituted for HCl-dioxane, and the free amine could be isolated by dissolution of the trifluoroacetic acid salt in ethyl acetate followed by extraction with aqueous base. Alternatively, the trifluoroacetic acid salt could be converted to the hydrochloride by dissolution in a slight excess of 9H dioxane-HCl at 0° C. and evaporation.

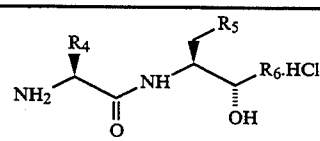

| Example | $R_4$ | $R_5$ | $R_6$ | FAB-MS Base, $M^+ + H$ | $^1H$ NMR (partial), δ |
|---|---|---|---|---|---|
| 282 | $CH_2SCH_3$ | Cy | (N/S heterocycle) | 358 (100) | ($D_2O$) 2.07(S, 3H), 2.65(dd, 1H) 2.85(dd, 1H), 4.09(dd, 1H), 4.53(m, 1H), 5.35(d, 1H), 7.85(d, 1H), 8.01(d, 1H). |
| 283[a] | $CH_2SCH_3$ | Cy | OH (branched alkyl) | | ($D_2O$) 0.87(d, 3H), 0.93(d, 3H), 2.19(s, 3H), 2.99(dd, 1H), 3.11 (dd, 1H), 3.38(m, 1H), 3.51(m, 1H), 4.19(dd, 1H), 4.32(m, 1H) |
| 284[b] | iPr | Ph | OH (branched alkyl) | 337 (100) | ($CDCl_3$) 0.33, 0.83, 0.85, and 0.92(d, 3H ea), 1.88(m, 1H), 2.18(m, 1H), 4.52(, 1H). |
| 285 | n-Pr | Cy | COOiPr | | |
| 286 | iPr | Ph | COOiPr | | |
| 287 | $CH_2SCH_3$ | Cy | (N/N-OCH$_2$Ph heterocycle) | 461 (100) | ($D_2O$) 2.15(S, 3H), 2.76 and 2.98(dd, 1H ea), 4.14(dd, 1H), 5.20(d, 1H), 5.73(m, 2H) |
| 288 | $CH_2C=CH_2$ | Cy | COOiPr | | (DMSO) 1.18(d, 6H), 3.83, 4.01, 4.23, and 4.84(m, 1H ea), 5.15(m, 2H), 5.6(d, 1H), 5.7(m, 1H) |

*[a] = Boc cleaved with TFA, and HCl-dioxane at 0° C.
*[b] = Boc cleaved with TFA, free base isolated.

We claim:
1. A compound of the formula

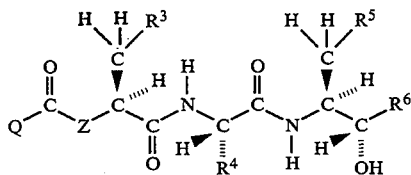

wherein Q is

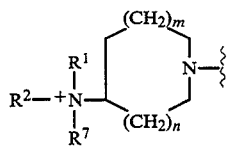

with the proviso that $R^7$ may be absent and that when $R^7$ is absent the nitrogen does not carry a positive charge and $X^-$ is absent; $X^-$ represents a pharmaceutically acceptable anion or shared anion; m and n are independently 0 to 1; $R^1$ and $R^2$ are independently selected from hydrogen, $C_1$ to $C_8$ alkyl, $C_1$ to $C_6$ alkoxy-$C_2$ to $C_8$ alkyl, $C_1$ to $C_6$ alkylamino-$C_2$ to $C_8$ alkyl or di($C_1$ to $C_8$ alkyl)amino-$C_2$ to $C_8$ alkyl, or $R^1$ and $R^2$ taken together with the nitrogen atom to which they are attached form a 4 to 8 membered ring containing 0, 1 or 2 atoms selected from the group consisting of oxygen and nitrogen, the remaining atoms in the ring being carbon, said ring optionally containing one or two substituents selected from hydroxy and $C_1$ to $C_6$ alkyl, the hydroxy substituent being attached to a carbon in the ring and the $C_1$ to $C_6$ alkyl substituents being attached to a carbon or nitrogen in the ring; $R^7$ is $C_1$ to $C_8$ alkyl; Z is $CH_2$, O or NH; $R^3$ is phenyl, $C_5$ to $C_7$ cycloalkyl, 1-naphthyl, 2-naphthyl, phenylmethyl, 2-thienyl, 3-thienyl, wherein said phenyl is optionally substituted with one or two groups selected from the group consisting of $C_1$ to $C_5$ alkoxy and halogen; $R^4$ is $C_1$ to $C_8$ alkyl, $C_1$ to $C_8$ substituted alkyl wherein the alkyl moiety is substituted with hydroxy, $C_1$ to $C_8$ alkylthio or $C_1$ to $C_8$ alkoxy; 4-imidazolymethyl, thienylmethyl, or $C_2$ to $C_8$ alkenyl-methyl; $R^5$ is $C_5$ to $C_7$ cycloalkyl or phenyl; and $R^6$ is COO-$C_1$ to $C_8$ alkyl; $CONR^{11}R^{12}$, wherein each of $R^{11}$ and $R^{12}$ is hydrogen or $C_1$-$C_8$ alkyl or $CONHR^8$ wherein $R^8$ is $C_1$ to $C_8$ alkyl substituted with 1 to 3 halogen atoms;
and the pharmaceutically acceptable salts thereof.

2. A compound according to claim 1, wherein Q is

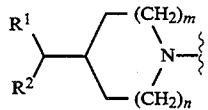

wherein $R^1$ and $R^2$ are as defined above and m and n are each 1.

3. A compound according to claim 22, wherein $R^3$ is phenyl, p-methoxyphenyl, benzyl, 1-naphthyl, cyclohexyl, 2-thienyl or 3-thienyl; $R^4$ is $C_1$ to $C_5$ alkyl, $C_1$ to $C_5$ alkylthio-$C_1$ to $C_3$ alkyl, $C_1$ to $C_5$ alkoxy-$C_1$ to $C_3$ alkyl, $C_2$ to $C_4$ alkenylmethyl or 4-imidazolymethyl; and $R_5$ is cyclohexyl.

4. A compound according to claim 3, wherein $R^6$ is —COO-$C_1$ to $C_8$ alkyl or $CONHR^8$ wherein $R^8$ is $C_1$ to $C_8$ alkyl or $C_1$ to $C_8$ alkyl substituted with 1 to 3 fluorine atoms.

5. A compound of claim 4, wherein $R^1$ and $R^2$ are independently selected from hydrogen, $C_1$ to $C_8$ alkyl and di($C_1$ to $C_3$ alkyl)amino-$C_2$ to $C_4$ alkyl, or $R^1$ and $R^2$ taken together with the nitrogen to which they are attached form a ring which is morpholine, 4-methylpiperazine, pyrrolidine, or piperidine.

6. A compound of claim 1, said compound being selected from those wherein:

a) $R^7$ is methyl, $R^1$ is methyl, $R^2$ is methyl, m and n are 1, Z is NH, $R^3$ is phenyl, $R^4$ is methylthiomethyl, $R^5$ is cyclohexyl, X is iodide and $R^6$ is COO-isopropyl; or b) $R^7$ is methyl, $R^1$ is methyl, $R^2$ is methyl, m and n are 1, Z is $CH_2$, $R^3$ is phenyl, $R^4$ is methylthiomethyl, $R^5$ is cyclohexyl, X is iodide and $R^6$ is COO-isopropyl; or c) $R^7$ is absent, $R^1$ is ethyl, $R^2$ is methyl, m and n are 1, Z is $CH_2$, $R^3$ is phenyl, $R^4$ is methylthiomethyl, $R^5$ is cyclohexyl, and $R^6$ is COO-isopropyl; or d) $R^7$ is absent, $R^1$ is methyl, $R^2$ is methyl, m and n are 1, Z is $CH_2$, $R^3$ is phenyl, $R^4$ is methylthiomethyl, $R^5$ is cyclohexyl, and $R^6$ is COO-(trans-2, trans-4-dimethylcylopent-1-yl); or e) $R^7$ is absent, $R^1$ is methyl, $R^2$ is methyl, m and n are 1, Z is $CH_2$, $R^3$ is phenyl, $R^4$ is methylthiomethyl, $R^5$ is cyclohexyl, and $R^6$ is COO-(trans-2, trans-5-dimethylcylopent-1-yl); or f) $R^7$ is absent, $R^1$ is methyl, $R^2$ is methyl, m and n are 1, Z is NH, $R^3$ is phenyl, $R^4$ is methylthiomethyl, $R^5$ is cyclohexyl, and $R^6$ is COO-isopropyl; or g) $R^7$ is absent, $R^1$ is methyl, $R^2$ is methyl, m and n are 1, Z is NH, $R^3$ is cyclohexyl, $R^4$ is methylthiomethyl, $R^5$ is cyclohexyl, and $R^6$ is COO-isopropyl; or h) $R^7$ is absent, $R^1$ is methyl, $R^2$ is methyl, m and n are 1, Z is NH, $R^3$ is phenyl, $R^4$ is methylthiomethyl, $R^5$ is cyclohexyl, and $R^6$ is COO-isopropyl; or i) $R^7$ is absent, $R^1$ and $R^2$ taken together form a 4-methylpiperazine ring, m and n are 1, Z is NH, $R^3$ is phenyl, $R^4$ is methylthiomethyl, $R^5$ is cyclohexyl, and $R^6$ is COO-isopropyl; or j) $R^7$ is absent, $R^1$ and $R^2$ taken together form a pyrrolidine ring, m and n are 1, Z is NH, $R^3$ is phenyl, $R^4$ is methylthiomethyl, $R^5$ is cyclohexyl, and $R^6$ is COO-isopropyl; or k) $R^7$ is absent, $R^1$ is methyl, $R^2$ is methyl, m and n are 1, Z is $CH_2$, $R^3$ is phenyl, $R^4$ is methylthiomethyl, $R^5$ is cyclohexyl, and $R^6$ is COO-isopropyl; or l) $R^7$ is absent, $R^1$ is methyl, $R^2$ is methyl, m and n are 1, Z is $CH_2$, $R^3$ is phenyl, $R^4$ is methylthiomethyl, $R^5$ is cyclohexyl, and $R^6$ is COO-isopropyl; or m) $R^7$ is absent, $R^1$ is methyl, $R^2$ is methyl, m and n are 1, Z is NH, $R^3$ is phenyl, $R^4$ is methylthiomethyl, $R^5$ is cyclohexyl, and $R^6$ is COO-(3-pentyl); or n) $R^7$ is absent, $R^1$ is methyl, $R^2$ is methyl, m and n are 1, Z is NH, $R^3$ is phenyl, $R^4$ is methylthiomethyl, $R^5$ is cyclohexyl, and $R^6$ is COO-(2,2-dimethylcylopentyl); or o) $R^7$ is absent, $R^1$ is methyl, $R^2$ is methyl, m and n are 1, Z is NH, $R^3$ is phenyl, $R^4$ is methylthiomethyl, $R^5$ is cyclohexyl, and $R^6$ is COO-(trans-2, trans-4-dimethylcylopentane); or p) $R^7$ is absent, $R^1$ is ethyl, $R^2$ is ethyl, m and n are 1, Z is $CH_2$, $R^3$ is phenyl, $R^4$ is methylthiomethyl, $R^5$ is cyclohexyl, and $R^6$ is COO-isopropyl; or q) $R^7$ is absent, $R^1$ is methyl, $R^2$ is methyl, m and n are 1, Z is $CH_2$, $R^3$ is 2-thienyl, $R^4$ is methylthiomethyl, $R^5$ is cyclohexyl, and $R^6$ is COO-isopropyl; or r) $R^7$ is absent, $R^1$ is hydrogen, $R^2$ is methyl, m and n are 1, Z is $CH_2$, $R^3$ is phenyl, $R^4$ is methylthiomethyl, $R^5$ is cyclohexyl, and $R^6$ is COO-isopropyl; or s) $R^7$ is absent, $R^1$ is methyl, $R^2$ is methyl, m and n are 1, Z is $CH_2$, $R^3$ is phenyl, $R^4$ is methylthiomethyl, $R^5$ is cyclohexyl, and $R^6$ is COO-(2,2-dimethylcylopentyl).

7. A compound according to claim 2, wherein $R^7$ is absent; $R^1$ and $R^2$ are independently selected from $C_1$ to $C_7$ alkyl; m and n are independently selected from 0 and 1; $R^3$ is phenyl optionally substituted with one or two groups selected from $C_1$ to $C_5$ alkoxy and halogen; $C_5$ to $C_7$ cycloalkyl; 1-naphthyl, 2-naphthyl and phenylmethyl; $R^4$ is $C_1$ to $C_8$ alkyl optionally substituted with hydroxy, $C_1$ to $C_8$ alkyloxy or $C_1$ to $C_8$ alkylthio; 4-imidazolymethyl or $C_2$ to $C_8$ alkenyl-methyl; $R^5$ is $C_5$ to $C_7$ cycloalkyl or phenyl; and $R^6$ is COO-$C_1$ to $C_8$ alkyl.

* * * * *